United States Patent
Dominguez et al.

(10) Patent No.: US 10,829,743 B2
(45) Date of Patent: *Nov. 10, 2020

(54) CATALYST AND USE THEREOF

(71) Applicant: JOHNSON MATTHEY PUBLIC LIMITED COMPANY, London (GB)

(72) Inventors: Beatriz Dominguez, Cambridgeshire (GB); Ursula Schell, Cambridgeshire (GB); Christian Kratzer, Oss (NL); Thomas Kalthoff, Cambridgeshire (GB)

(73) Assignee: Johnson Matthey Public Limited Company, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/501,495

(22) PCT Filed: Aug. 6, 2015

(86) PCT No.: PCT/GB2015/052286
§ 371 (c)(1),
(2) Date: Feb. 3, 2017

(87) PCT Pub. No.: WO2016/020695
PCT Pub. Date: Feb. 11, 2016

(65) Prior Publication Data
US 2017/0226485 A1 Aug. 10, 2017

(30) Foreign Application Priority Data
Aug. 6, 2014 (GB) .................................. 1413899.4

(51) Int. Cl.
C12P 7/40 (2006.01)
C12N 9/02 (2006.01)
C12N 9/80 (2006.01)
C12P 7/24 (2006.01)
C12P 7/42 (2006.01)

(52) U.S. Cl.
CPC ................ C12N 9/001 (2013.01); *C12P 7/24* (2013.01); *C12P 7/42* (2013.01); *C12Y 103/01031* (2013.01)

(58) Field of Classification Search
CPC .. C12P 7/24; C12P 7/26; C12P 41/002; C12N 9/0008; C12N 9/001; C12N 9/0036; C12N 15/70; C12Y 101/01
USPC ...................... 435/147, 254.11, 189
See application file for complete search history.

(56) References Cited

U.S. PATENT DOCUMENTS

| 9,328,372 B2 | 5/2016 | Omura et al. |
| 2010/0035315 A1 | 2/2010 | Stürmer et al. |
| 2011/0053986 A1 | 3/2011 | Finch et al. |
| 2013/0045513 A1 | 2/2013 | Maurer et al. |
| 2013/0203093 A1 | 8/2013 | Honda et al. |

FOREIGN PATENT DOCUMENTS

| WO | WO01/32906 A2 | 5/2001 |
| WO | 2007/011887 A2 | 1/2007 |
| WO | 2008/034648 A1 | 3/2008 |
| WO | WO2006/101239 A1 | 9/2008 |
| WO | 2008/143956 A1 | 11/2008 |
| WO | 2010/075574 A2 | 7/2010 |
| WO | 2010075574 A2 | 7/2010 |
| WO | 2011/092345 A1 | 8/2011 |
| WO | 2013/068901 A1 | 5/2013 |

OTHER PUBLICATIONS

Davos et al., Proteins: Structure, Function and Genetics, 2000, vol. 41: 98-107.*
Wristlock et al., Quarterly Reviews of Biophysics 2003, vol. 36 (3): 307-340.*
Kwiatkowski et al., Biochemistry 38:11643-11650, 1999.*
Kisselev L., Structure, 2002, vol. 10: 8-9.*
Hall et al. ( Ang chem Int ED 2007, 46, pp. 3934-3937.*
Breithaupt et al ( PNAC 2006, 103, pp. 14337-14342).*
Schaller et al. JBC 1997, 272, pp. 28066-28072.*
Stueckler, C. et al., "Stereo-Controlled Asymmetric Bioreduction of α,β-Dehydroamino Acid Derivatives," Adv. Synth. Catal., 353, 2011, pp. 1169-1173.
Hall, M. et al., "Asymmetric Bioreduction of C=C Bonds Using Enoate Reductases OPR1, OPR3 and YqjM: Enzyme-Based Sterocontrol," Adv. Synth. Catal, 350, 2008, pp. 411-418.
Kataoka, M. et al., "Cloning and Overexpression of the Old Yellow Enzyme Gene of Candida Macedoniensis, and its Application to the Production of a Chiral Compound," Journal of Biotechnology, vol. 114, 2004, pp. 1-9.
International Search Report issued in Application No. PCT/GB2015/052286, dated Oct. 21, 2015.
Great Britain Search Report issued in Application No. GB1513940.5, dated Aug. 4, 2016.
Great Britain Search Report issued in Application No. GB1513940.5, dated Aug. 8, 2016.
Great Britain Search and Examination Report issued in Application No. GB1620841.5, dated Feb. 15, 2017.
Stephen F. Altschul, Basic Local Alignment Search Tool, Journal of Molecular Biology, 1990, pp. 403-410, vol. 215.

(Continued)

*Primary Examiner* — Robert B Mondesi
*Assistant Examiner* — Mohammad Y Meah
(74) *Attorney, Agent, or Firm* — BakerHostetler

(57) ABSTRACT

Disclosed is a method that includes use of a catalyst in a method of reducing a substrate, the method including contacting a substrate with a catalyst, optionally in the presence of a co-substrate, thereby to generate a reduced substrate. The catalyst is a polypeptide including an amino acid sequence having at least 70% identity to SEQ ID NO: 1, SEQ ID NO: 7 or SEQ ID NO: 9. In the method the substrate concentration is at least 50 mM.

13 Claims, 12 Drawing Sheets

Specification includes a Sequence Listing.

(56) References Cited

OTHER PUBLICATIONS

James Lalonde, et al., Immobilization of Enzymes, Enzyme Catalysis in Organic Synthesis, 2002, pp. 163-184, Wiley-VCH Verlag GmbH, Weinheim, Germany.
Elisabetta Brenna, et al., Cascade Coupling of Ene Reductases with Alcohol Dehydrogenases: Enantioselective Reduction of Prochiral Unsaturated Aldehydes, 2012, ChemCatChem, pp. 653-659, vol. 4, Wiley-VCH Verlag GmbH & Co. KGaA, Weinheim, Germany.
Mélanie Hall, et al., Asymmetric Bioreduction of Activated C=C Bonds Using Zymomonas mobilis NCR Enoate Reductase and Old Yellow Enzymes OYE 1-3 from Yeasts, European Journal of Organic Chemistry, 2008, pp. 1511-1516, Wiley-VCH Verlag GmbH & Co. KGaA, Weinheim, Germany.
T.F. Smith, et al., Identification of Common Molecular Subsequences, Journal of Molecular Biology, 1981, pp. 195-197, vol. 147, Academic Press Inc. (London) Ltd.
William R. Pearson, et al., Improved tools for biological sequence comparison, Proceedings of the National Academy of Science USA, Apr. 1988, pp. 2444-2448, vol. 85.
Toshifumi Hirata, et al., Stereospecific hydrogenation of the C=C double bond of enones by *Escherichia coli* overexpressing an enone reductase of Nicotiana tabacum, Journal of Molecular Catalysis B: Enzymatic, 2009, pp. 158-162, vol. 59, Elsevier B.V.
Christoph K. Winkler, et al., Chemoenzymatic Asymmetric Synthesis of Pregabalin Precursors via Asymmetric Bioreduction of β-Cyanoacrylate Esters Using Ene-Reductases, The Journal of Organic Chemistry, 2013, pp. 1525-1533, vol. 78, ACS Publications.
David Mangan, et al., A Three-Enzyme System Involving an Ene-Reductase for Generating Valuable Chiral Building Blocks, Advanced Systhesis & Catalysis, 2012, pp. 2185-2190, vol. 354, Wiley-VCH Verlag GmbH & Co. KGaA, Weinheim, Germany.
David J. Mansell, et al., Biocatalytic Asymmetric Alkene Reduction: Crystal Structure and Characterization of a Double Bond Reductase from Nicotiana tabacum, ACS Catalysis, 2013, pp. 370-379, vol. 3, ACS Publications.
Saul B. Needleman, et al., A General Method Applicable to the Search for Similarities in the Amino Acid Sequence of Two Proteins, Journal of Molecular Biology, 1970, pp. 443-453, vol. 48.
Yanto Yanto, et al., Asymmetric Bioreduction of Alkenes Using Ene-Reductases YersER and KYE1 and Effects of Organic Solvents, Organic Letters, 2011, pp. 2540-2543, vol. 13, No. 10, American Chemical Society.
Jörg Pietruszka, et al., Ene Reductase-Catalysed Synthesis of (R)-Profen Derivatives, Advanced Synthesis & Catalysis, 2012, pp. 751-756, vol. 354, Wiley-VCH Verlag GmbH & Co. KGaA, Weinheim, Germany.
Naseem Iqbal, et al., Asymmetric bioreduction of activated carbonecarbon double bonds using Shewanella yellow enzyme (SYE-4) as novel enoate reductase, Tetrahedron, 2012, pp. 7619-7623, vol. 68, Elsevier Ltd.
Molecular Cloning: A Laboratory Manual, vol. 3, 3rd edition, Cold Spring Harbor Laboratory Press, Cold Spring Harbor, New York, 2001, Chapter 15, Expression of Cloned Genes in *Escherichia coli*, 15.1-15.13; Chapter 15, Protocol 1, Expression of Cloned Genes in *E. coli* Using IPTG-Inducible Promoters, 15.14-15.35; Chapter 15, Protocol 5, Purificatio of Fusoin Proteins by Affinity Chromatography on Glutathione Agarose, 15.36-15.65.
*Acidovorax avenae* subsp. avenae ATCC 19860, complete genome. Accession No. CP002521 Region: 67850..68978. GenBank (online), retrieved on Mar. 19, 2019, Jan. 9, 2014, retrieved from the Internet: www.ncbi.nlm.nih.gov/nuccore/cp002521.
Chromobacterium violaceum ATCC 12472, complete genome. Accession No. AE016825 Region: 3794884..3795978. GenBank (online), retrieved on Mar. 19, 2019, Jan. 31, 2014, retrieved from the Internet: www.ncbi.nlm.nih/gov/nuccore/AE016825.1.
"Bacillus infantis NRRL B-14911, complete genome. Accession No. CP006643 Region: 3211641..3212657". GenBank (online), retrieved on Mar. 19, 2019, Jan. 31, 2014, retrieved from the Internet: www.ncbi.nlm.nih.gov/nuccore/CP006643.
Database UniProt [Online] Dec. 15, 2003 (Dec. 15, 2003), "SubName: Full=Flavoprotein NADH-dependent oxidoreductase {RCO: 0000313|EMBL:AAQ61162.1};", XP002745354, retrieved from EBI accession No. UNIPROT: Q7NSC5 Database accession No. Q7NSC5.
Agarwal, S. et al., "Solvent free biocatalytic synthesis of isoniazid from isonicotinamide using whole cell of Bacillus smithii strain IITR6b2", Journal of Molecular Catalysis B: Enzymatic, vol. 97, Dec. 2013, pp. 67-73.
Banerjee, A. et al., "A rapid and sensitive fluorometric assay method for the determination of nitrilase activity," Biotechnology and Applied Biochemistry, vol. 37, Issue 3, Jun. 2003, pp. 289-293.
Botes, A. L. et al., "Biocatalytic resolution of 1,2-epoxyoctane using resting cells of different yeast strains with novel epoxide hydrolase activities," Biotechnology Letters, vol. 20, No. 4, Apr. 1998, pp. 421-426.
Lucas et al., "12-oxophytodienoate reductase [*Acidovorax avenae* subsp. Avenae ATCC 19860]", Jan. 2014 https://www.ncbi.nlm.nih.gov/protein/adx43981.
Zheng Ren-Chao, et al., "Enantioselective Synthesis of (S)-3-cyano-5-methylhexanoic Acid by a High DMSO Concentration Tolerable *Arthrobacter* sp. ZJB-09277", Biochemical Engineering Journal, vol. 83, 2014, pp. 97-103.
Sall, S.N. and Chotte, J.-L., "Phosphatase and Urease Activities in a Tropical Sandy Soil as Affected by Soil Water-Holding Capacity and Assay Conditions" Communications in Soil Science and Plant Analysis, vol. 33, Nos. 19 & 20, 2002, pp. 3745-3755.
Database UniProt [Online], SubName: Full=12-oxophytodJ enoate reductase {ECO:0000313|EMBL:ADX43981.1}; EC=1.3.1. 42 ( EC0: 0000313 I EMBL:ADX43981.1}; XP002745353, retrieved from EBI accession No. UNIPR0T: F0Q098. Database accession No. F0Q098 sequence.
Database UniProt [Online],"RecName: Full=NADPH dehydrogenase {ECO:0000256|HAMAP-Rule:MF 01614}; EC=1.6.99.1 {ECO:0000256|HAMAP-Rule:MF 01614};", XP002745355, retrieved from EBI accession No. UNIPR0T: Q2B6D5 Database accession No. Q2B6D5 sequence.
Database Geneseq [Online],"Nucleotide sequence SEQ ID 172725.", retrieved from EBI accession No. GSN: AWK99521 Database accession No. AWK99521 sequence.

* cited by examiner

*Figure 18*

```
ENE103     -MDTSLFSSYTVKDVTLKNRIVMAPMCMYSSRNEDGKVENWHLTHYTSPAVGQVGLIIVE
ENE101     -MSHTLFDFVQAGDLQLANRIAMAPLTRN---RSPNAVPKDITATYYAQ---RATAGLLITE
ENE102     MRADYLLTPLTMGAVALSNRVVMAPLTRLRNIEPGDVPGPLAKEYYRQ--PASAGLIVAE
                             . *  *  ***         *            **

ENE103     ATAVTAQGFISPQDLGIWSDDHIEGLQQLTGMMKENGTPAGIQLARAGRKAVIE------G
ENE101     APAISHQGQGYADVPGLYSTEQLDGWKKVTAAVHEPGGPIVTQLWHVGRISRNDLQPDGG
ENE102     GTRISPTAKGYAGAPCIYSEEQVRAWSEVTGAVRQDGGKIALQIWHTGRISRPSLQPNGD
            *              *  *              *    **  *  **

ENE103     EIIAPSAVAF--------------NEKMKSPKEMTKEEIKETIEAFKEGAVRA-KKAGF
ENE101     APVAPSAIAANSKTYLIDKATGQGHFAATSEPPALDAEELPGIVHDYAAAASNAVETAGF
ENE102     APVGPSAIQADSPTNIR--AADGSLVREQCDTPRALEIEEIEDIIEDYPPAADNA-RRAGF
             * ****                             *         *        ***

ENE103     EVIEIHAAHGYLINEPLSPLSNLREDEYGGIAENRYPFLREVIDSIQSVWDGPLF-VRVS
ENE101     DGVEIRGANGYLLDQFLKTGANRRTDDYGGSIENPARLLLEAFPAVVDAIGGGRVGIRLS
ENE102     DMVEIRGAHGYLIDQFLSPAANVPTDQYGGSVENKARPLLEVVDAVVAEWDADHVGIRIS
              ***  * ***  *  *      *   **  * *          *              *

ENE103     ASDY-------NENGLDVEDYVTFGPWMKEQGIDLIDVSSGALVPARI-----HAYPGYQVK
ENE101     PVTPANDIVDADPQPLFDYVI--RQLAPLGLAYVHVIEGSTGGPPELEDRPFDYEALKTA
ENE102     PLGIFNGVSNTDQLDMALYLA--EQLAKPELAFLHISEPDWAGGPTLDDG-FYAE-LPQR
                            *          *           *

ENE103     FAETIKNEADIPTGAVGLITSGLQAEELLQNDPADLIPIARELLRDPYFRKTAAKQLGTE
ENE101     YREAGGKCAWMVNN------AYDRALAMEAVASGPADIVAFGHAFISNPDLVERLRQDA--P
ENE102     Y------PGVIIGAG------GYSAEKAETLLKKGFIDAAAFGRSYIANPDIVERLYQNA--P

ENE103     IEPFK---QYDRG----W-----
ENE101     LNPWDSKTFYGGGERGYTDYPTLGESAKG
ENE102     LMPPKPDTFYGGGAEGYTDYPTL-----
```

CATALYST AND USE THEREOF

FIELD OF THE INVENTION

The invention relates to biocatalysts for use as such, methods for the reduction of a substrate using a biocatalyst and kits containing the biocatalyst.

BACKGROUND

The use of enzymes (biocatalysts) in organic synthesis offers a more ecologically sustainable alternative to the use of metal catalysts, as well as allowing a high degree of chemo-, regio- and/or enantio-selectivity in the reactions catalysed.

Processes for enzymatic reduction of alkene derivatives have been described using ene-reductase enzymes of the "Old Yellow Enzyme" family. For example, US 2010/0035315 describes the reduction of substrates in the presence of the enzyme YqjM from *Bacillus subtilis* and the enzymes OPR1 and OPR3 from the tomato plant, wherein the substrates are alkene derivatives at a concentration of 5 mM.

SUMMARY OF THE INVENTION

The present inventors have found that reduction reactions, particularly reduction of unsaturated carbon-carbon bonds, may be advantageously performed using a catalyst as described herein. Specifically, the present inventors have found that the catalyst as described herein is particularly useful for applications in industrial reactions, owing to its tolerance to high substrate concentrations.

In a general aspect, the present invention provides uses of the catalyst described herein as a catalyst, for example for catalysing reduction reactions, and processes for performing a reduction reaction which use the catalyst described herein.

In a first development, the invention provides the use of a catalyst described herein for catalysing a reduction reaction, wherein the substrate concentration is high. For example, the invention provides the use of a catalyst for catalysing a reduction reaction, wherein the substrate concentration is at least 50 mM, at least 100 mM, at least 200 mM, at least 300 mM or at least 500 mM.

In a first aspect of the invention there is provided the use of a catalyst for catalysing a reduction reaction, wherein the catalyst is a polypeptide comprising an amino acid sequence having at least 50% identity to SEQ ID NO: 1.

In one embodiment, there is provided the use of a catalyst for catalysing a reduction reaction, wherein the catalyst is a polypeptide comprising an amino acid sequence having at least 50% identity to SEQ ID NO: 1, and wherein the substrate concentration is at least 10 mM, for example at least 100 mM, such as at least 200 mM or at least 500 mM. The use may comprise contacting the substrate with the catalyst.

In one embodiment, there is provided the use of a catalyst for catalysing a reduction reaction, wherein the catalyst is a polypeptide comprising an amino acid sequence having at least 70% identity to SEQ ID NO: 1, and wherein the substrate concentration is at least 50 mM. The use may comprise contacting the substrate with the catalyst.

In one embodiment, there is provided the use of a catalyst for catalysing a reduction reaction, wherein the catalyst is a polypeptide comprising an amino acid sequence having at least 70% identity to SEQ ID NO: 7, and wherein the substrate concentration is at least 50 mM. The use may comprise contacting the substrate with the catalyst.

In one embodiment, there is provided the use of a catalyst for catalysing a reduction reaction, wherein the catalyst is a polypeptide comprising an amino acid sequence having at least 70% identity to SEQ ID NO: 9, and wherein the substrate concentration is at least 50 mM. The use may comprise contacting the substrate with the catalyst.

In a second development, the invention provides the use of a catalyst described herein in a method of reducing a substrate, wherein the substrate concentration is high. For example, the invention provides the use of a catalyst in a method of reducing a substrate, wherein the substrate concentration is at least 50 mM, at least 100 mM, at least 200 mM, at least 300 mM or at least 500 mM.

In a second aspect of the invention there is provided the use of a catalyst in a method of reducing a substrate, the method comprising contacting a substrate with a catalyst, wherein the catalyst is a polypeptide comprising an amino acid sequence having at least 50% identity to SEQ ID NO: 1. There is also provided a method for reducing a substrate, the method comprising contacting a substrate with a catalyst, wherein the catalyst is a polypeptide comprising an amino acid sequence having at least 50% identity to SEQ ID NO: 1. There is also provided the use of a catalyst in a method of reducing a substrate, the method comprising contacting a substrate with a catalyst, wherein the catalyst is a polypeptide comprising an amino acid sequence having at least 70% identity to SEQ ID NO: 1. There is also provided a method for reducing a substrate, the method comprising contacting a substrate with a catalyst, wherein the catalyst is a polypeptide comprising an amino acid sequence having at least 70% identity to SEQ ID NO: 1. The method may optionally comprise contacting a substrate with a catalyst in the presence of a co-substrate, In one embodiment, there is provided the use of a catalyst in a method of reducing a substrate, the method comprising contacting a substrate with a catalyst, wherein the catalyst is a polypeptide comprising an amino acid sequence having at least 70% identity to SEQ ID NO:1, and wherein in the method the substrate concentration is at least 50 mM.

In one embodiment, there is provided the use of a catalyst in a method of reducing a substrate, the method comprising contacting a substrate with a catalyst, wherein the catalyst is a polypeptide comprising an amino acid sequence having at least 70% identity to SEQ ID NO:7, and wherein in the method the substrate concentration is at least 50 mM.

In one embodiment, there is provided the use of a catalyst in a method of reducing a substrate, the method comprising contacting a substrate with a catalyst, wherein the catalyst is a polypeptide comprising an amino acid sequence having at least 70% identity to SEQ ID NO:9, and wherein in the method the substrate concentration is at least 50 mM.

In one embodiment, the substrate comprises an activated ethylene group, such as an ethylene group that is $\alpha,\beta$ to an acyl, carboxy, acyloxy, nitro, acylamino or nitrile group.

In one embodiment, the substrate comprises an activated ethylene group, such as an ethylene group that is $\alpha,\beta$ to an acyl, carboxy, acyloxy, nitro, or acylamino group.

The invention also provides the catalyst as described herein, nucleic acids encoding the catalyst, host cells containing a nucleic acid encoding the catalyst, host cells expressing the catalyst, processes for producing the catalyst as described herein, and catalyst preparations comprising the catalyst as described herein. The invention also provides a kit comprising the catalyst, optionally together with one or more further catalysts.

SUMMARY OF THE FIGURES

FIG. 18 shows a Clustal Omega (1.2.1) multiple sequence alignment of SEQ ID NO:s 1, 7 and 9.

SEQUENCES

Figure 1:
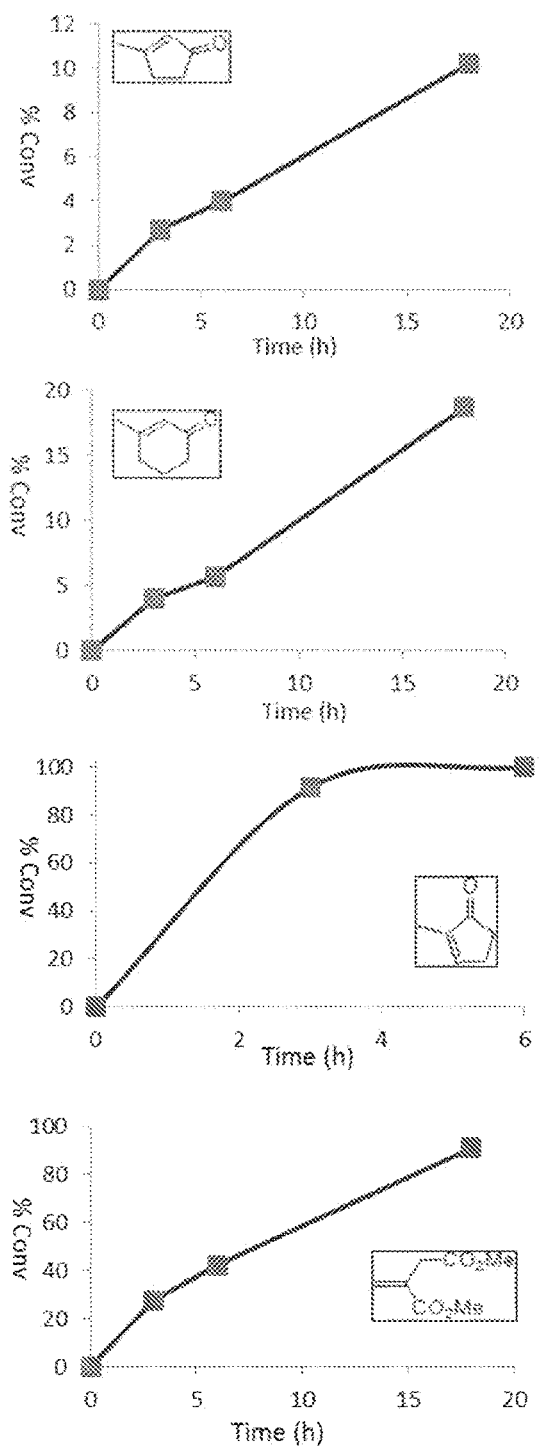
FIG. 1 shows the change in percentage conversion of a series of substrates (shown) to their reduced forms (not shown) over time (hours) using a catalyst according to an embodiment of the invention.

The catalysts for use in the present invention are described herein with reference to the sequence identification numbers listed below. The sequences are disclosed in the sequence listing.

SEQ ID NO:1 Catalyst amino acid sequence (ENE-101 amino acid sequence)

SEQ ID NO:2 Nucleic acid sequence encoding catalyst (encoding SEQ ID NO:1)

SEQ ID NO:3 Nucleic acid sequence, codon-optimised, encoding catalyst (encoding SEQ ID NO:1)

SEQ ID NO:4 Catalyst amino acid sequence, including T7 tag

SEQ ID NO:5 Catalyst amino acid sequence, including His tag and T7 tag

SEQ ID NO:6 Nucleic acid sequence encoding catalyst including His tag and T7 tag (encoding SEQ ID NO:5)

SEQ ID NO:7 Catalyst amino acid sequence (ENE-102 amino acid sequence)

SEQ ID NO:8 Nucleic acid sequence encoding catalyst (encoding SEQ ID NO:7)

SEQ ID NO:9 Catalyst amino acid sequence (ENE-103 amino acid sequence)

SEQ ID NO:10 Nucleic acid sequence encoding catalyst (encoding SEQ ID NO:9)

DETAILED DESCRIPTION OF THE INVENTION

The present invention provides the use of a catalyst in a substrate reaction. As described in further detail below, the catalyst is suitable for use in a reduction reaction, such as the reduction of an activated ethylene group. The catalyst allows for the production of a reaction product in high yields, for example greater than 90% conversion, and/or with high stereoselectivity, for example greater than 99% ee. The catalyst may be used at high substrate concentrations, for example at 50, 100 and 300 mM. Indeed, the inventors have established that the catalyst may be used at substrate concentrations as high as 750 and 1,500 mM.

The present invention provides the use of a catalyst for catalysing a reduction reaction, wherein the substrate concentration is high. The present invention provides the use of a catalyst for catalysing a reduction reaction wherein the substrate concentration is high, and wherein the catalyst is a polypeptide comprising an amino acid sequence having at least 70% identity to one of the amino acid sequences as set out in FIG. 18.

The present invention provides the use of a catalyst as a reduction catalyst, wherein the catalyst is a polypeptide comprising an amino acid sequence having at least 70% identity to SEQ ID NO:1. The present invention provides the use of a catalyst as a reduction catalyst, wherein the catalyst is a polypeptide comprising an amino acid sequence having at least 70% identity to SEQ ID NO:7. The present invention provides the use of a catalyst as a reduction catalyst, wherein the catalyst is a polypeptide comprising an amino acid sequence having at least 70% identity to SEQ ID NO:9. The use may be use as a hydrogenation catalyst.

The present invention provides the use of a catalyst as a reduction catalyst, wherein the catalyst is a polypeptide comprising an amino acid sequence having at least 95% identity to SEQ ID NO:1. The present invention provides the use of a catalyst as a reduction catalyst, wherein the catalyst is a polypeptide comprising an amino acid sequence having at least 95% identity to SEQ ID NO:7. The present invention provides the use of a catalyst as a reduction catalyst, wherein the catalyst is a polypeptide comprising an amino acid sequence having at least 95% identity to SEQ ID NO:9. The use may be use as a hydrogenation catalyst.

The present invention provides the use of a catalyst as a reduction catalyst wherein the catalyst is a polypeptide comprising or consisting of the amino acid sequence of SEQ ID NO:1. The present invention provides the use of a catalyst as a reduction catalyst wherein the catalyst is a polypeptide comprising or consisting of the amino acid sequence of SEQ ID NO:7. The present invention provides the use of a catalyst as a reduction catalyst wherein the catalyst is a polypeptide comprising or consisting of the amino acid sequence of SEQ ID NO:9. The use may be use as a hydrogenation catalyst.

The present inventors have shown that the catalysts described herein are capable of catalysing reactions in the presence of high substrate concentrations. Inhibition of enzyme activity by high substrate or product concentrations is the often a significant problem in the scale up of enzymatic processes. The catalysts, uses and methods disclosed herein are therefore advantageous for process scale up.

The present invention provides the use of a catalyst as described herein for catalysing a reduction reaction, wherein the substrate concentration is high. For example, the invention provides the use of a catalyst for catalysing a reduction reaction, wherein the substrate concentration is at least 10 mM, at least 20 mM, at least 50 mM, at least 100 mM, at least 200 mM, at least 300 mM, at least 500 mM or at least 1500 mM. The catalyst is a catalyst as described herein, for example the catalyst may be a polypeptide comprising an amino acid sequences having at least 70% sequence identity to any one of SEQ ID NO:s 1, 7 or 9. The catalyst may be a polypeptide comprising an amino acid sequence having at least 80%, at least 90%, at least 95%, at least 98%, at least 99% or 100% sequence identity to any one of SEQ ID NO:s 1, 7 or 9.

In one embodiment the invention provides the use of a catalyst for catalysing a reduction reaction, wherein the substrate concentration is at least 50 mM and wherein the catalyst is a polypeptide comprising an amino acid sequence having at least 95% sequence identity to any one of SEQ ID NO:s 1, 7 or 9.

In one embodiment the invention provides the use of a catalyst for catalysing a reduction reaction, wherein the substrate concentration is at least 100 mM and wherein the catalyst is a polypeptide comprising an amino acid sequence having at least 95% sequence identity to any one of SEQ ID NO:s 1, 7 or 9.

In one embodiment the invention provides the use of a catalyst for catalysing a reduction reaction, wherein the substrate concentration is at least 50 mM and wherein the catalyst is a polypeptide comprising or consisting of the amino acid sequence of SEQ ID NO:s 1, 7 or 9.

In one embodiment the invention provides the use of a catalyst for catalysing a reduction reaction, wherein the substrate concentration is at least 100 mM and wherein the catalyst is a polypeptide comprising or consisting of the amino acid sequence of SEQ ID NO:s 1, 7 or 9.

Catalyst—Structure

The catalyst is a polypeptide. Polypeptide catalysts are known as enzymes, and therefore the catalyst is an enzyme. Enzymes are also known as biocatalysts. More specifically, the catalyst is a reductase. In particular, the catalyst is a reductase capable of reducing a substrate having a 2-cyclohexen-1-one or 2-cyclopenten-1-one component. The catalyst is capable of using NADH as a cofactor. The catalyst is a flavin-dependent enzyme.

The catalyst may be an enzyme belonging to the group known as "Old Yellow Enzymes". Using the nomenclature of the Nomenclature Committee of the International Union of Biochemistry and Molecular Biology (NC-IUBMB) the catalyst is an enzyme belonging to class 1 (oxidoreductases). The catalyst may be an enzyme belonging to EC 1.3 (which group includes oxidoreductases that act on the CH—CH group of donors). The catalyst may be an enzyme belonging to EC 1.3.1 (which group uses NADH or NADPH as cofactor). The catalyst may be an enzyme belonging to EC 1.3.1.42 (which group includes 12-oxophytodienoate reductases).

The catalyst may be a recombinant polypeptide, that is, the catalyst may have been expressed from a recombinant nucleic acid sequence, as discussed in more detail below. The catalyst may have been expressed from a nucleic acid as provided herein. The catalyst may have been expressed from the nucleic acid sequence set out as SEQ ID NO:3.

Alternatively, the catalyst may be a naturally occurring polypeptide. The catalyst may be a reductase that is expressed by an endogenous (native) gene in a bacterium.

The catalyst may be an enzyme expressed by the phytobacterium *Acidovorax avenae*. The catalyst may be a reductase expressed by *A. avenae*. Specifically, the catalyst may be a reductase expressed by *A. avenae* deposited as ATCC 19860 (Lucas et al., 2011). The polypeptide identified by accession number F0Q098 (version 1 in UniProt database) is a reductase encoded by the *A. avenae* nucleic acid sequence identified by accession number ADX43981.1 (version 1, EMBL-EBI European Nucleotide Archive, Lucas et al., 2011).

The amino acid sequence set out as SEQ ID NO:1 is the amino acid sequence of F0Q098. The nucleic acid sequence set out as SEQ ID NO:2 is the nucleic acid sequence of ADX43981.1.

The catalyst may be an enzyme expressed by *Chromobacterium violaceum*. The catalyst may be a reductase expressed by *C. violaceum*. Specifically, the catalyst may be a reductase expressed by *C. violaceum* deposited as ATCC 12472, The polypeptide identified by accession number Q7NSC5 is a reductase encoded by *C. violaceum* (version 1, Uniprot, released 15 Dec. 2003).

The amino acid sequence set out as SEQ ID NO:7 is the amino acid sequence of Q7NSC5.

The catalyst may be an enzyme expressed by a *Bacillus* species. The catalyst may be a reductase expressed by a *Bacillus* species. Specifically, the catalyst may be a reductase expressed by *Bacillus* sp. NRRL B-14911. The polypeptide identified by accession number Q2B6D5 is a reductase encoded by *Bacillus* sp. NRRL B-14911 (version 1, Uniprot, released 4 Apr. 2006).

The amino acid sequence set out as SEQ ID NO:9 is the amino acid sequence of Q2B6D5.

FIG. 18 shows an alignment of SEQ ID NO:1, SEQ ID NO:7 and SEQ ID NO:9. In FIG. 18, and elsewhere in this application the amino acid sequence of SEQ ID NO:1 is termed ENE-101, the amino acid sequence of SEQ ID NO:7 is termed ENE-102 and the amino acid sequence of SEQ ID NO:9 is termed ENE-103.

The catalyst may be a polypeptide comprising an amino acid sequence having at least about 50% identity to SEQ ID NO:1. The catalyst may be a polypeptide comprising an amino acid sequence having at least about 60%, at least about 70%, at least about 80%, at least about 90%, at least about 95%, at least about 98%, or at least about 99% sequence identity to SEQ ID NO:1. The catalyst may be a polypeptide comprising an amino acid sequence having 100% identity to SEQ ID NO:1, that is, the catalyst may be a polypeptide comprising the amino acid sequence set out as SEQ ID NO:1.

The catalyst may be a polypeptide comprising an amino acid sequence having at least about 50% identity to SEQ ID NO:7. The catalyst may be a polypeptide comprising an amino acid sequence having at least about 60%, at least about 70%, at least about 80%, at least about 90%, at least about 95%, at least about 98%, or at least about 99% sequence identity to SEQ ID NO:7. The catalyst may be a polypeptide comprising an amino acid sequence having 100% identity to SEQ ID NO:7, that is, the catalyst may be a polypeptide comprising the amino acid sequence set out as SEQ ID NO:7.

The catalyst may be a polypeptide comprising an amino acid sequence having at least about 50% identity to SEQ ID NO:9. The catalyst may be a polypeptide comprising an amino acid sequence having at least about 60%, at least about 70%, at least about 80%, at least about 90%, at least about 95%, at least about 98%, or at least about 99% sequence identity to SEQ ID NO:9. The catalyst may be a polypeptide comprising an amino acid sequence having 100% identity to SEQ ID NO:9, that is, the catalyst may be a polypeptide comprising the amino acid sequence set out as SEQ ID NO:9.

The catalyst may be a polypeptide consisting essentially of an amino acid sequence having at least about 50% sequence identity to SEQ ID NO:1. The catalyst may be a polypeptide consisting essentially of an amino acid sequence having at least about 60%, at least about 70%, at least about 80%, at least about 90%, at least about 95%, at least about 98%, or at least about 99% sequence identity to SEQ ID NO:1. The catalyst may be a polypeptide consisting essentially of an amino acid sequence having 100% sequence identity to SEQ ID NO:1, that is, the catalyst may be a polypeptide consisting essentially of the amino acid sequence set out as SEQ ID NO:1.

The catalyst may be a polypeptide consisting essentially of an amino acid sequence having at least about 50% sequence identity to SEQ ID NO:7. The catalyst may be a polypeptide consisting essentially of an amino acid sequence having at least about 60%, at least about 70%, at least about 80%, at least about 90%, at least about 95%, at least about 98%, or at least about 99% sequence identity to SEQ ID NO:7. The catalyst may be a polypeptide consisting essentially of an amino acid sequence having 100% sequence identity to SEQ ID NO:7, that is, the catalyst may be a polypeptide consisting essentially of the amino acid sequence set out as SEQ ID NO:7.

The catalyst may be a polypeptide consisting essentially of an amino acid sequence having at least about 50% sequence identity to SEQ ID NO:9. The catalyst may be a polypeptide consisting essentially of an amino acid sequence having at least about 60%, at least about 70%, at least about 80%, at least about 90%, at least about 95%, at least about 98%, or at least about 99% sequence identity to SEQ ID NO:9. The catalyst may be a polypeptide consisting essentially of an amino acid sequence having 100% sequence identity to SEQ ID NO:9, that is, the catalyst may be a polypeptide consisting essentially of the amino acid sequence set out as SEQ ID NO:9.

The catalyst may be a polypeptide consisting of an amino acid sequence having at least about 50% sequence identity to SEQ ID NO:1. The catalyst may be a polypeptide consisting of an amino acid sequence having at least about 60%, at least about 70%, at least about 80%, at least about 90%, at least about 95%, at least about 98%, or at least about 99% sequence identity to SEQ ID NO:1. The catalyst may be a polypeptide consisting of an amino acid sequence having 100% sequence identity to SEQ ID NO:1, that is, the catalyst may be a polypeptide consisting of the amino acid sequence set out as SEQ ID NO:1.

The catalyst may be a polypeptide consisting of an amino acid sequence having at least about 50% sequence identity to SEQ ID NO:7. The catalyst may be a polypeptide consisting of an amino acid sequence having at least about 60%, at least about 70%, at least about 80%, at least about 90%, at least about 95%, at least about 98%, or at least about 99% sequence identity to SEQ ID NO:7. The catalyst may be a polypeptide consisting of an amino acid sequence having 100% sequence identity to SEQ ID NO:7, that is, the catalyst may be a polypeptide consisting of the amino acid sequence set out as SEQ ID NO:7.

The catalyst may be a polypeptide consisting of an amino acid sequence having at least about 50% sequence identity to SEQ ID NO:9. The catalyst may be a polypeptide consisting of an amino acid sequence having at least about 60%, at least about 70%, at least about 80%, at least about 90%, at least about 95%, at least about 98%, or at least about 99% sequence identity to SEQ ID NO:9. The catalyst may be a polypeptide consisting of an amino acid sequence having 100% sequence identity to SEQ ID NO:9, that is, the catalyst may be a polypeptide consisting of the amino acid sequence set out as SEQ ID NO:9.

The catalyst may be a polypeptide comprising an amino acid sequence having at least about 50% similarity to SEQ ID NO:1. Sequence similarity is also known as sequence homology. The catalyst may be a polypeptide comprising an amino acid sequence having at least about 60%, at least about 70%, at least about 80%, at least about 90%, at least about 95%, at least about 98%, or at least about 99% similarity to SEQ ID NO:1. The catalyst may be a polypeptide comprising an amino acid sequence having 100% similarity to SEQ ID NO:1.

The catalyst may be a polypeptide comprising an amino acid sequence having at least about 50% similarity to SEQ ID NO:7. Sequence similarity is also known as sequence homology. The catalyst may be a polypeptide comprising an amino acid sequence having at least about 60%, at least about 70%, at least about 80%, at least about 90%, at least about 95%, at least about 98%, or at least about 99% similarity to SEQ ID NO:7. The catalyst may be a polypeptide comprising an amino acid sequence having 100% similarity to SEQ ID NO:7.

The catalyst may be a polypeptide comprising an amino acid sequence having at least about 50% similarity to SEQ ID NO:9. Sequence similarity is also known as sequence homology. The catalyst may be a polypeptide comprising an amino acid sequence having at least about 60%, at least about 70%, at least about 80%, at least about 90%, at least about 95%, at least about 98%, or at least about 99% similarity to SEQ ID NO:9. The catalyst may be a polypeptide comprising an amino acid sequence having 100% similarity to SEQ ID NO:9.

The catalyst may be a polypeptide consisting essentially of an amino acid sequence having at least about 50% sequence similarity to SEQ ID NO:1. The catalyst may be a polypeptide consisting essentially of an amino acid sequence having at least about 60%, at least about 70%, at least about 80%, at least about 90%, at least about 95%, at least about 98%, or at least about 99% sequence similarity to SEQ ID NO:1. The catalyst may be a polypeptide consisting essentially of an amino acid sequence having 100% sequence similarity to SEQ ID NO:1.

The catalyst may be a polypeptide consisting essentially of an amino acid sequence having at least about 50% sequence similarity to SEQ ID NO:7. The catalyst may be a polypeptide consisting essentially of an amino acid sequence having at least about 60%, at least about 70%, at least about 80%, at least about 90%, at least about 95%, at least about 98%, or at least about 99% sequence similarity to SEQ ID NO:7. The catalyst may be a polypeptide consisting essentially of an amino acid sequence having 100% sequence similarity to SEQ ID NO:7.

The catalyst may be a polypeptide consisting essentially of an amino acid sequence having at least about 50% sequence similarity to SEQ ID NO:9. The catalyst may be a polypeptide consisting essentially of an amino acid sequence having at least about 60%, at least about 70%, at least about 80%, at least about 90%, at least about 95%, at least about 98%, or at least about 99% sequence similarity to SEQ ID NO:9. The catalyst may be a polypeptide consisting essentially of an amino acid sequence having 100% sequence similarity to SEQ ID NO:9.

The catalyst may be a polypeptide consisting of an amino acid sequence having at least about 50% sequence similarity to SEQ ID NO:1. The catalyst may be a polypeptide consisting of an amino acid sequence having at least about at least about 60%, at least about 70%, at least about 80%, at least about 90%, at least about 95%, at least about 98%, or at least about 99% sequence similarity to SEQ ID NO:1. The catalyst may be a polypeptide consisting of an amino acid sequence having 100% similarity to SEQ ID NO:1.

The catalyst may be a polypeptide consisting of an amino acid sequence having at least about 50% sequence similarity to SEQ ID NO:7. The catalyst may be a polypeptide consisting of an amino acid sequence having at least about at least about 60%, at least about 70%, at least about 80%, at least about 90%, at least about 95%, at least about 98%, or at least about 99% sequence similarity to SEQ ID NO:7. The catalyst may be a polypeptide consisting of an amino acid sequence having 100% similarity to SEQ ID NO:7.

The catalyst may be a polypeptide consisting of an amino acid sequence having at least about 50% sequence similarity to SEQ ID NO:9. The catalyst may be a polypeptide consisting of an amino acid sequence having at least about at least about 60%, at least about 70%, at least about 80%, at least about 90%, at least about 95%, at least about 98%, or at least about 99% sequence similarity to SEQ ID NO:9. The catalyst may be a polypeptide consisting of an amino acid sequence having 100% similarity to SEQ ID NO:9.

The catalyst may be a polypeptide comprising an amino acid sequence having a certain percentage sequence identity and/or similarity to SEQ ID NO:1, SEQ ID NO:7 or SEQ ID NO:9 as set out above. The polypeptide may comprise one or more additional amino acids. For example, the polypeptide may further comprise an affinity tag. The affinity tag may be useful for purifying the catalyst. Such affinity tags are well known in the art. For example the affinity tag may be a poly-histidine tag ("His tag"), for purifying the catalyst using a nickel column, it may be a T7 epitope tag (T7 tag) for purifying the protein using a column comprising an anti-T7 tag antibody, or it may be a glutathione-S-transferase tag ("GST tag"), for purifying the catalyst using a glutathione column. An affinity tag may be located at the N-terminus or at the C-terminus of the polypeptide. Alternatively or additionally, the polypeptide may further comprise a leader sequence at the N-terminus. The leader sequence may be useful for directing secretion and/or intracellular targeting of the polypeptide in a recombinant expression system. Leader sequences are also known as signal peptides and are well known in the art. Alternatively or additionally, the polypeptide may further comprise a label such as a fluorescent label.

The catalyst may be a polypeptide comprising an amino acid sequence having a certain percentage sequence identity and/or similarity to SEQ ID NO:1, SEQ ID NO:7, or SEQ ID NO:9 plus one or more additional amino acids, as set out above. The catalyst may be a polypeptide comprising an amino acid sequence consisting of the amino acid sequence set out as SEQ ID NO:1, SEQ ID NO:7, or SEQ ID NO:9. Specifically, the catalyst may be a polypeptide comprising an amino acid sequence consisting of the amino acid sequence set out as SEQ ID NO:1 plus an N-terminal T7 tag, such as the polypeptide set out as SEQ ID NO: 4. The catalyst may be a polypeptide comprising an amino acid sequence consisting of the amino acid sequence set out as SEQ ID NO:1 plus an N-terminal His tag and T7 tag, such as the polypeptide set out as SEQ ID NO: 5.

Catalyst—Function

The catalyst is a reductase. The catalyst is capable of catalysing the reduction of a substrate as defined herein. Specifically, the catalyst is capable of reducing an unsaturated carbon-carbon double bond. In particular, the catalyst may be capable of catalysing the reaction set out in the reaction scheme below:

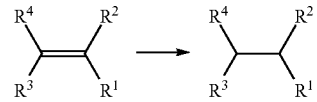

where each of —$R^1$ to —$R^4$ is as defined in further detail below, for example in the presence of a co-substrate.

In certain embodiments of the invention the catalyst may be capable of catalysing the reaction set out in the reaction scheme below:

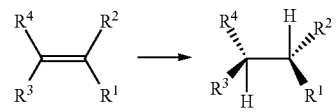

where each of —$R^1$ to —$R^4$ is as defined in further detail below, for example in the presence of a co-substrate.

The activity of the catalyst can be measured photometrically, for example by performing the reaction in the presence of NADH as cofactor and measuring the decrease in absorbance at 340 nM caused by the oxidation of NADH.

In one embodiment, the catalyst of the invention is an enzyme having activity in the reduction of the substrate in the presence of a NADH cofactor.

The amount of an enzyme can be expressed in terms of its activity using enzyme units. One enzyme unit (U) is the amount of enzyme that converts 1 μmol of substrate per minute. Typically, the number of enzyme units present in a catalyst preparation is assayed using a reference substrate, for example to provide U/mg of catalyst preparation. One U of the catalyst of the invention can be defined as the amount of catalyst that will catalyse 1 μmol of NADH to NAD per minute at pH 7 at 22° C., for example wherein the reference substrate is 1-octene-3-one. The reference substrate may be present at a concentration of 0.98 mM in the assay mixture. Reaction of NADH to NAD may be monitored using the change in absorbance at 340 nm, using techniques know to the person skilled in the art.

The activity of the catalyst in enzyme units can be used to express the amount of enzyme present in a catalyst preparation, which may provide the catalyst in a relatively crude form as described below.

(The katal expresses enzyme activity using SI base units, where one katal is the amount of enzyme that converts 1 mole of substrate per second, and therefore 1 U is equivalent to 1/60 microkatal.)

For example, the number of enzyme units present in a catalyst preparation may be determined according to the assay procedure set out below.

Two cuvettes containing 980 μL of solution A (1 mM solution of 1-octen-3-one in 0.1 M potassium phosphate buffer, pH 7.0) are incubated at 22° C. for at least 5 minutes, to provide a test cuvette and a blank cuvette. The reaction is initiated in the test cuvette by adding 10 μL of solution B (15 mM NADH in H$_2$O) and 10 μL of solution C (enzyme (e.g. lyophilised enzyme) solution in H$_2$O; 0.8 mg of catalyst preparation per mL H$_2$O) and mixing thoroughly. 10 μL of solution B and 10 μL of H$_2$O is added to the blank cuvette and mixed thoroughly. The decrease of absorbance over 1 minute at 340 nm at 22° C. is determined. (If the decrease is not linear, the enzyme solution (solution C) should be diluted with H$_2$O. ΔA340 min$^{-1}$ is determined using the maximum linear rate for both the test cuvette and the blank cuvette. Enzyme activity in U/mg of catalyst preparation is determined using the following formula:

$$(\Delta A340\ min^{-1}\ test - \Delta A340\ min^{-1}\ blank)/(6.2 \times 0.01 \times 0.8)$$

where $6.2 \times 10^3$ L mol$^{-1}$ cm$^{-1}$ is the molar extinction coefficient for NADH at 340 nm, 0.01 is the volume of enzyme solution in mL, and 0.8 is the mass of catalyst preparation in mg per mL (and can be adapted based on any dilution of Solution C).

Catalysts as disclosed herein are reductases. They may catalyse the reduction of 3-methylcyclohex-2-en-1-one (the substrate shown in entries 4 to 6 of Table 1) to generate a product having an ee value of 70% or more, 80% or more, 90% or more, 95% or more, 98%, or more, 99% or more, or 99.9% or more. Here, the catalyst may be used in the method set out in Experimental Procedure 1 or Experimental Procedure 2, as described herein.

Catalysts which are polypeptides comprising an amino acid sequence at least 50% identical to SEQ ID NO:1 and comprising one or more amino acid additions, substitutions and/or deletions relative to the amino acid sequence of SEQ ID NO:1 may catalyse the reduction of 3-methylcyclohex-2-en-1-one (the substrate shown in entries 4 to 6 of Table 1) to generate a product having an ee value of 70% or more, 80% or more, 90% or more, 95% or more, 98%, or more, 99% or more, or 99.9% or more. Here, the catalyst may be used in the method set out in Experimental Procedure 1 or Experimental Procedure 2, as described herein.

Catalysts which are polypeptides comprising an amino acid sequence at least 50% identical to SEQ ID NO:7 and comprising one or more amino acid additions, substitutions and/or deletions relative to the amino acid sequence of SEQ ID NO:7 may catalyse the reduction of 3-methylcyclohex-2-en-1-one (the substrate shown in entries 4 to 6 of Table 1) to generate a product having an ee value of 70% or more, 80% or more, 90% or more, 95% or more, 98%, or more, 99% or more, or 99.9% or more. Here, the catalyst may be used in the method set out in Experimental Procedure 1 or Experimental Procedure 2, as described herein.

Catalysts as disclosed herein are reductases. They may catalyse the reduction of 2-methylcyclopent-2-en-1-one (the substrate shown in entries 7 to 9 of Table 1) to give a product with a conversion rate of 70% or more, 80% or more, 90% or more, 95% or more, 98% or more, 99% or more, or 99.9% or more. Here, the catalyst may be used in the method set out in Experimental Procedure 1 or Experimental Procedure 2, as described in the Experimental section.

Catalysts which are polypeptides comprising an amino acid sequence at least 50% identical to SEQ ID NO:1 and comprising one or more amino acid additions, substitutions and/or deletions relative to the amino acid sequence of SEQ ID NO:1 may catalyse the reduction of 2-methylcyclopent-2-en-1-one (the substrate shown in entries 7 to 9 of Table 1) to give a product with a conversion rate of 70% or more, 80% or more, 90% or more, 95% or more, 98% or more, 99% or more, or 99.9% or more. Here, the catalyst may be used in the method set out in Experimental Procedure 1 or 2, as described in the Experimental section.

Catalysts which are polypeptides comprising an amino acid sequence at least 50% identical to SEQ ID NO:7 and comprising one or more amino acid additions, substitutions and/or deletions relative to the amino acid sequence of SEQ ID NO:7 may catalyse the reduction of 2-methylcyclopent-2-en-1-one (the substrate shown in entries 7 to 9 of Table 1) to give a product with a conversion rate of 70% or more, 80% or more, 90% or more, 95% or more, 98% or more, 99% or more, or 99.9% or more. Here, the catalyst may be used in the method set out in Experimental Procedure 1 or Experimental Procedure 2, as described in the Experimental section.

Catalysts which are polypeptides comprising an amino acid sequence at least 50% identical to SEQ ID NO:9 and comprising one or more amino acid additions, substitutions and/or deletions relative to the amino acid sequence of SEQ ID NO:9 may catalyse the reduction of 2-methylcyclopent-2-en-1-one (the substrate shown in entries 7 to 9 of Table 1) to give a product with a conversion rate of 70% or more, 80% or more, 90% or more, 95% or more, 98% or more, 99% or more, or 99.9% or more. Here, the catalyst may be used in the method set out in Experimental Procedure 1 or Experimental Procedure 2, as described in the Experimental section.

Catalysts as described herein are reductases having high substrate tolerance. They may catalyse the reduction of 2-methylcyclopent-2-en-1-one (the substrate shown in entries 7 to 9 of Table 1) when the substrate concentration is 50 mM to give a product with a conversion rate of 70% or more, 80% or more, 90% or more, 95% or more, 98% or more, 99% or more, or 99.9% or more. Here, the catalyst may be used in the method set out in Experimental Procedure 1 or Experimental Procedure 2, as described in the Experimental section. The reaction time may be 18 hours. The catalyst may be capable of giving a product with a conversion rate of 70% or more, 80% or more, 90% or more, 95% or more, 98% or more, 99% or more, or 99.9% or more in the "test reaction conditions" set out below.

Catalysts as described herein are reductases having high substrate tolerance. They may catalyse the reduction of 2-methylcyclopent-2-en-1-one (the substrate shown in entries 7 to 9 of Table 1) when the substrate concentration is 100 mM to give a product with a conversion rate of 70% or more, 80% or more, 90% or more, 95% or more, 98% or more, 99% or more, or 99.9% or more. Here, the catalyst may be used in the method set out in Experimental Procedure 1 or Experimental Procedure 2, as described in the Experimental section. The reaction time may be 18 hours. The catalyst may be capable of giving a product with a conversion rate of 70% or more, 80% or more, 90% or more, 95% or more, 98% or more, 99% or more, or 99.9% or more in the "test reaction conditions" set out below.

Catalysts as described herein are reductases having high substrate tolerance. They may catalyse the reduction of 2-methylcyclopent-2-en-1-one (the substrate shown in entries 7 to 9 of Table 1) when the substrate concentration is 300 mM to give a product with a conversion rate of 70% or more, 80% or more, 90% or more, 95% or more, 98% or more, 99% or more, or 99.9% or more. Here, the catalyst may be used in the method set out in Experimental Procedure 1 or Experimental Procedure 2, as described in the Experimental section. The reaction time may be 18 hours. The catalyst may be capable of giving a product with a conversion rate of 70% or more, 80% or more, 90% or more, 95% or more, 98% or more, 99% or more, or 99.9% or more in the "test reaction conditions" set out below.

The "test reaction conditions" may be 250 mM phosphate buffer pH 7, 1.1 mM NAD+, 30 mM D-glucose, 10 U/mL GDH, at 35° C. The reaction time may be 3, 6, or 18 hours.

The skilled person is able to distinguish catalysts of the present disclosure, which have high substrate tolerance and are therefore suitable for the uses and methods described herein, from catalysts that do not have high substrate tolerance. A catalyst with high substrate tolerance has the functional capabilities set out above. By contrast, a catalyst that does not have high substrate tolerance does not have those functional capabilities. A catalyst that does not have high substrate tolerance may catalyse the reduction of 2-methylcyclopent-2-en-1-one (the substrate shown in entries 7 to 9 of Table 1) when the substrate concentration is 50 mM to give a product with a conversion rate of 20% or less, 10% or less, 5% or less or 2% or less. A catalyst that does not have high substrate tolerance may catalyse the reduction of 2-methylcyclopent-2-en-1-one when the substrate concentration is 20 mM or less to give a product with a conversion rate of 30% or more, 40% or more, 50% or more, 60% or more, 70% or more, 80% or more, 90% or more, 95% or more, 98% or more, 99% or more, or 99.9% or more, and when the substrate concentration is 50 mM or more to give a product with a conversion rate of 30% or less, 20% or less, 10% or less, 5% or less or 2% or less. A catalyst that does not have high substrate tolerance may catalyse the reduction of 2-methylcyclopent-2-en-1-one when the substrate concentration is 20 mM or less to give a product with a conversion rate of 30% or more, 40% or more, 50% or more, 60% or more, 70% or more, 80% or more, 90% or more, 95% or more, 98% or more, 99% or more, or 99.9% or more, and when the substrate concentration is 300 mM or more to give a product with a conversion rate of 30% or less, 20% or less, 10% or less, 5% or less or 2% or less. Here the catalyst may be used in the method set out in Experimental Procedure 1 or 2, as described in the Experimental section, or in the "test conditions" described ablve. The reaction time may be 18 hours.

Nucleic Acids

Provided herein are nucleic acid sequences encoding the catalyst. The nucleic acid may be DNA or RNA. The nucleic acid may be single stranded or double stranded. The catalyst may be encoded by a nucleic acid sequence as set out in SEQ ID NO:2, which is a nucleic acid sequence from the *A. avenae* genome (Lucas et al., 2011). The nucleic acid sequence of SEQ ID NO:2 encodes the amino acid sequence of SEQ ID NO:1. Because the genetic code is degenerate (more than one codon may encode an amino acid), the nucleic acid sequence of SEQ ID NO:2 may be altered to provide further nucleic acid sequences that also encode the amino acid sequence of SEQ ID NO:1.

The catalyst may be encoded by a nucleic acid sequence as set out in SEQ ID NO:8. The nucleic acid sequence of SEQ ID NO:8 encodes the amino acid sequence of SEQ ID NO:7. Because the genetic code is degenerate (more than one codon may encode an amino acid), the nucleic acid sequence of SEQ ID NO:8 may be altered to provide further nucleic acid sequences that also encode the amino acid sequence of SEQ ID NO:7.

The catalyst may be encoded by a nucleic acid sequence as set out in SEQ ID NO:10. The nucleic acid sequence of SEQ ID NO:10 encodes the amino acid sequence of SEQ ID NO:9. Because the genetic code is degenerate (more than one codon may encode an amino acid), the nucleic acid sequence of SEQ ID NO:10 may be altered to provide further nucleic acid sequences that also encode the amino acid sequence of SEQ ID NO:9.

A nucleic acid sequence encoding the catalyst may be introduced into a host cell, to provide a recombinant host cell expressing the catalyst. The catalyst may be provided in a cell by providing a host cell expressing the catalyst. The catalyst may be provided in an isolated form by providing a host cell expressing the catalyst, expressing the catalyst in the host cell and isolating the catalyst. A host cell may be a prokaryotic cell such as *Escherichia coli, Bacillus subtilis* or a *Pseudomonas* species. A host cell may be a eukaryotic cell, for example a yeast cell such as *Saccharomyces cerevisiae* or a mammalian cell such as a HeLa cell or a CHO cell.

A nucleic acid sequence encoding the catalyst may be optimised for expression in a recombinant host cell. Because the genetic code may vary between organisms (codon preference may vary between organisms), expression of a desired polypeptide in a specific host cell may be improved by altering the nucleic acid encoding the polypeptide in accordance with the codon preference of the host cell. The *A. avenae* nucleic acid sequence SEQ ID NO:2 was altered to provide SEQ ID NO:3, for improved expression of the catalyst in a host cell, such as *E. coli*. Because the genetic code is degenerate, the nucleic acid sequence of SEQ ID NO: 3 may be altered to provide further nucleic acid sequences that also encode the catalyst in a host cell such as *E. coli*. Because codon usage may vary between organisms, the nucleic acid sequences of SEQ ID NO:2 and/or SEQ ID NO:3 may be altered to provide further nucleic acids suitable for expressing the catalyst in other host cells. Because the catalyst may be a variant of the amino acid sequence of SEQ ID NO:1, a nucleic acid sequence encoding an variant of SEQ ID NO:1 may be suitable for expressing the catalyst in a host cell. Similarly, the nucleic acid sequences of SEQ ID NO:8 and SEQ ID NO:10 may be altered to provide further nucleic acids suitable for expressing catalysts in other host cells, and because the catalyst may be a variant of the amino acid sequence of SEQ ID NO:7 and SEQ ID NO:9, a nucleic acid sequence encoding a variant of SEQ ID NO:7 or SEQ ID NO:9 may be suitable for expressing the catalyst in a host cell.

A nucleic acid sequence encoding the catalyst may comprise a nucleic acid sequence having at least 50% identity to SEQ ID NO:3. A nucleic acid sequence encoding the catalyst may comprise a nucleic acid sequence having at least about 60%, at least about 70%, at least about 80%, at least about 90%, at least about 95%, at least about 98%, or at least about 99% identity to SEQ ID NO:3. A nucleic acid sequence encoding the catalyst may comprise a nucleic acid sequence having 100% identity to SEQ ID NO:3. A nucleic acid sequence encoding the catalyst may comprise a nucleic acid sequence as set out in SEQ ID NO:3.

A nucleic acid sequence encoding the catalyst may comprise a nucleic acid sequence having at least 50% identity to SEQ ID NO:8. A nucleic acid sequence encoding the catalyst may comprise a nucleic acid sequence having at least about 60%, at least about 70%, at least about 80%, at least about 90%, at least about 95%, at least about 98%, or at least about 99% identity to SEQ ID NO:8. A nucleic acid sequence encoding the catalyst may comprise a nucleic acid sequence having 100% identity to SEQ ID NO:8. A nucleic acid sequence encoding the catalyst may comprise a nucleic acid sequence as set out in SEQ ID NO:8.

A nucleic acid sequence encoding the catalyst may comprise a nucleic acid sequence having at least 50% identity to SEQ ID NO:10. A nucleic acid sequence encoding the catalyst may comprise a nucleic acid sequence having at least about 60%, at least about 70%, at least about 80%, at least about 90%, at least about 95%, at least about 98%, or at least about 99% identity to SEQ ID NO:10. A nucleic acid sequence encoding the catalyst may comprise a nucleic acid sequence having 100% identity to SEQ ID NO:10. A nucleic acid sequence encoding the catalyst may comprise a nucleic acid sequence as set out in SEQ ID NO:10.

The nucleic acid encoding the catalyst may be in isolated and/or purified form, or free or substantially free of material with which it is naturally associated, such as free or substantially free of nucleic acid sequences that flank SEQ ID NO:2 in the *A. avenae* genome. The nucleic acid encoding the catalyst may be in isolated and/or purified form, or free or substantially free of material with which it is naturally associated, such as free or substantially free of nucleic acid sequences that flank SEQ ID NO:8 in the *C. violaceum* genome. The nucleic acid encoding the catalyst may be in isolated and/or purified form, or free or substantially free of material with which it is naturally associated, such as free or substantially free of nucleic acid sequences that flank SEQ ID NO:10 in the *Bacillus* sp. genome.

Generally, nucleic acids encoding the catalyst may be obtained by modification of SEQ ID NO:2 or SEQ ID NO:3. Recombinant techniques such as site-directed mutagenesis may be used to modify SEQ ID NO:2 or SEQ ID NO:3 to provide further nucleic acid sequences that encode the catalyst. Such further nucleic acid sequences may encode variants of SEQ ID NO:1. Nucleic acids encoding the catalyst may be obtained by modification of SEQ ID NO:8. Recombinant techniques such as site-directed mutagenesis may be used to modify SEQ ID NO:8 to provide further nucleic acid sequences that encode the catalyst. Such further nucleic acid sequences may encode variants of SEQ ID NO:7. Nucleic acids encoding the catalyst may be obtained by modification of SEQ ID NO:10. Recombinant techniques such as site-directed mutagenesis may be used to modify SEQ ID NO:10 to provide further nucleic acid sequences that encode the catalyst. Such further nucleic acid sequences may encode variants of SEQ ID NO:9.

The present invention provides a nucleic acid having comprising the nucleic acid sequence set out as SEQ ID NO:3. The present invention also provides a nucleic acid comprising a nucleic acid sequence having at least 80%, at least 90%, at least 95%, at least 98%, or at least 99% identity to SEQ ID NO:3, wherein the nucleic acid encodes the catalyst. The present invention provides a nucleic acid comprising a nucleic acid sequence having at least 80%, at least 90%, at least 95%, at least 98%, or at least 99% identity to SEQ ID NO:3, wherein the nucleic acid encodes a polypeptide comprising an amino acid sequence having at least 50% identity to SEQ ID NO:1, which polypeptide is a reductase.

The present invention provides a nucleic acid comprising the nucleic acid sequence set out as SEQ ID NO:8. The present invention also provides a nucleic acid comprising a nucleic acid sequence having at least 80%, at least 90%, at least 95%, at least 98%, or at least 99% identity to SEQ ID NO:8, wherein the nucleic acid encodes the catalyst. The present invention provides a nucleic acid comprising a nucleic acid sequence having at least 80%, at least 90%, at least 95%, at least 98%, or at least 99% identity to SEQ ID NO:8, wherein the nucleic acid encodes a polypeptide comprising an amino acid sequence having at least 50% identity to SEQ ID NO:7, which polypeptide is a reductase.

The present invention provides a nucleic acid having comprising the nucleic acid sequence set out as SEQ ID NO:10. The present invention also provides a nucleic acid comprising a nucleic acid sequence having at least 80%, at least 90%, at least 95%, at least 98%, or at least 99% identity to SEQ ID NO:10, wherein the nucleic acid encodes the catalyst. The present invention provides a nucleic acid comprising a nucleic acid sequence having at least 80%, at least 90%, at least 95%, at least 98%, or at least 99% identity to SEQ ID NO:10, wherein the nucleic acid encodes a polypeptide comprising an amino acid sequence having at least 50% identity to SEQ ID NO:9, which polypeptide is a reductase.

Vectors, Host Cells and Methods for the Production of the Catalyst

A nucleic acid encoding the catalyst may be incorporated into a replicable vector. The vector may be used to replicate the nucleic acid in a compatible host cell. Thus a nucleic acid encoding a catalyst can be produced by introducing a nucleic acid encoding a catalyst into a replicable vector, introducing the vector into a compatible host cell, and growing the host cell under conditions which bring about replication of the vector.

The nucleic acid encoding the catalyst may be operably linked to a control sequence which is capable of providing for the expression of the catalyst by the host cell. For example, the nucleic acid encoding the catalyst may be in an expression vector. For example, the nucleic acid encoding the catalyst may be in a plasmid or a chromosome. The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences.

Optionally, the N terminal ttg codon in SEQ ID NO:2 may be replaced with a start codon such as atg.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage phagemid or baculoviral, cosmids, YACs, BACs, or PACs as appropriate. Vectors include gene therapy vectors, for example vectors based on adenovirus, adeno-associated virus, retrovirus (such as HIV or MLV) or alpha virus vectors.

The vectors may be provided with an origin of replication, optionally a promoter for the expression of the catalyst and optionally a regulator of the promoter. The vector may be a low copy plasmid, a medium copy plasmid or a high copy plasmid. The vectors may contain one or more selectable marker genes, for example an ampicillin resistance gene in the case of a bacterial plasmid or a neomycin resistance gene for a mammalian vector. Vectors may be used in vitro, for example for the production of RNA or used to transfect or transform a host cell. Systems for cloning and expression of a polypeptide in a variety of different host cells are well known.

The vectors may include other sequences such as promoters or enhancers to drive the expression of the inserted nucleic acid. A promoter may be an inducible promoter, such that expression of the catalyst may be commenced or enhanced by adding an inducer to the host cell growth medium. For example the promoter may be based on the lac operon, for which IPTG (isopropyl-beta-D-thio-galactoside) is an inducer. Alternatively, a promoter may be a constitutively active promoter. A promoter may be a strong promoter.

The vectors may include other nucleic acid sequences so that the catalyst is produced as a fusion protein (for example a fusion protein comprising the catalyst and an affinity tag), and/or nucleic acid sequences encoding a leader sequence so that the polypeptide produced in the host cell is secreted from the cell.

Provided herein are host cells, such as those mentioned above, which may be cultured under conditions to bring about expression of the catalyst. The catalyst may be provided within a host cell. In this way the catalyst may be used in vivo in a reduction reaction, that is, the catalyst may be used in an intracellular reduction reaction. Alternatively, expression of the catalyst may be followed by isolation of the catalyst from the host cell. The catalyst may be isolated using electrophoretic and/or chromatographic techniques. The catalyst may be isolated for example by expressing the catalyst as a fusion protein including an affinity tag and using an agent that binds the affinity tag to recover the fusion protein. The agent may be attached to a sepharose column, for example. An affinity tag may be cleaved from the protein after it has been isolated.

Catalyst Preparation

The catalyst may be provided in a pure, or substantially pure, form. The catalyst in a pure, or substantially pure, form is separated from other molecules or cellular components which naturally accompany a protein (e.g. ribosomes, cell membrane components).

The catalyst may be provided in a relatively crude form as a catalyst preparation, for example the catalyst preparation may be a lysate or clarified lysate of recombinant cells that express the catalyst. The catalyst preparation may be a homogenate or paste of recombinant cells that express the catalyst.

The catalyst may be comprised in a host cell. The catalyst may be provided in a free form or in an immobilised form. In immobilised from the catalyst may be attached to an inert carrier such as a cellulose powder or synthetic polymer such as polyethene (Lalonde and Margolin, 2002).

Provided herein are methods of producing the catalyst, which methods include expressing a nucleic acid encoding the catalyst in a host cell, and isolating the catalyst from the host cell. The method may include lysing the host cell to provide a cell lysate, and may further include removing host cell debris (e.g. by centrifugation) to provide a clarified cell lysate. The step of lysing the host cell may use a lysis buffer that comprises flavin mononucleotide (FMN), for example the lysis buffer may comprise about 1-50 µM FMN, or about 5-25 µM FMN, or about 20 µM FMN. Additionally or alternatively, the step of lysing the host cell may use a lysis buffer that contains $MgSO_4$, for example the lysis buffer may comprise about 1-50 mM $MgSO_4$, about 1-5 mM $MgSO_4$, or about 5 mM $MgSO_4$. The lysis buffer may comprise FMN and $MgSO_4$.

Water may be removed from the catalyst or catalyst preparation to provide the catalyst in a lyophilised form. The catalyst may be provided as a lyophilisate. The catalyst or catalyst preparation may be frozen.

The amount of catalyst in the catalyst preparation can be expressed as units of enzyme (U) per mg of catalyst preparation, for example as units of enzyme per mg of lyophilisate.

The amount of catalyst in the catalyst preparation may be at least about 0.25 U per mg of catalyst preparation, at least about 1 U per mg of catalyst preparation or at least about 3 U per mg of catalyst preparation (e.g. determined using the assay method described above). The amount of catalyst in the catalyst preparation may be at most about 5 U per mg of catalyst preparation, at most about 10 U per mg of catalyst preparation, at most about 20 U per mg of catalyst preparation or at most about 50 U per mg of catalyst preparation (e.g. determined using the assay method described above). The catalyst preparation may be a lyophilisate comprising at least about 0.25 U per mg of lyophilisate, at least about 1 U per mg of lyophilisate or at least about 3 U per mg of lyophilisate (e.g. determined using the assay method described above). The amount of catalyst in the lyophilisate may be at most about 5 U per mg of lyophilisate, at most about 10 U per mg of lyophilisate, at most about 20 U per mg of lyophilisate or at most about 50 U per mg of lyophilisate (e.g. determined using the assay method described above).

The amount of catalyst in the preparation may be in a range selected from the upper and lower amounts given above, for example in the range 1-20 U per mg of catalyst preparation.

The present invention provides a catalyst preparation, comprising the catalyst as defined herein. The catalyst preparation may comprise at least a certain amount of catalyst (defined in terms of U of catalyst per mg of catalyst preparation) as defined above. For example, the catalyst preparation may comprise a catalyst which is a polypeptide comprising an amino acid having at least about 70% sequence identity to SEQ ID NO:1 wherein the amount of catalyst in the catalyst preparation is at least 0.25 U per mg of catalyst preparation. For example, the catalyst preparation may comprise a catalyst which is a polypeptide comprising an amino acid having at least about 70% sequence identity to SEQ ID NO:7 wherein the amount of catalyst in the catalyst preparation is at least 0.25 U per mg of catalyst preparation. For example, the catalyst preparation may comprise a catalyst which is a polypeptide comprising an amino acid having at least about 70% sequence identity to SEQ ID NO:9 wherein the amount of catalyst in the catalyst preparation is at least 0.25 U per mg of catalyst preparation.

Similarity and Sequence Identity

Amino acid sequence identity and similarity and nucleic acid sequence identity may be measured using standard bioinformatics software tools, such as the freely available EMBOSS, or BLAST, software tools. Default parameters are generally used. For example EMBOSS Needle pairwise sequence alignment can be used to determine amino acid sequence identity. EMBOSS Needle pairwise sequence alignment, which uses the Needleman-Wunsch algorithm (J. Mol. Biol. (48): 444-453 (1970)), can be used to determine amino acid sequence similarity, for example using default parameters and using a BLOSUM scoring matrix such as the BLOSUM62 scoring matrix. Default parameters may be used with a gap creation penalty=12 and gap extension penalty=4. Use of GAP may be preferred but other algorithms may be used, e.g. BLAST or TBLASTN (which use the method of Altschul et al. (1990) *J. Mol. Biol.* 215: 405-410), FASTA (which uses the method of Pearson and Lipman (1988) *PNAS USA* 85: 2444-2448), or the Smith-Waterman algorithm (Smith and Waterman (1981) *J. Mol Biol.* 147: 195-197), generally employing default parameters.

As discussed above, the catalyst is a polypeptide having at least 50% amino acid sequence identity to SEQ ID NO:1, and which is capable of catalysing the reduction of a substrate. Catalysts having less than 50% amino acid sequence identity to SEQ ID NO:1 are capable of catalysing the reduction of a substrate and therefore many polypeptides having at least 50% amino acid sequence identity are also capable of catalysing the reduction of a substrate. For example the enzyme known as YqjM from *Bacillus subtilis* (EC 1.6.99.1, UniProt entry P54550) has about 30% sequence identity to SEQ ID NO:1 and is capable of reducing certain alkene derivatives, the enzyme encoded by the tomato OYPR1 gene (EC 1.3.1.42, Uniprot Q9XG54) has about 42% sequence identity to SEQ ID NO:1 and is capable of reducing certain alkene derivatives, and the enzyme encoded by the tomato OYPR3 gene (EC 1.3.1.42, Uniprot Q9FEW9) has about 42% sequence identity to SEQ ID NO:1 and is capable of reducing certain alkene derivatives (see US 2010/0035315, which is hereby incorporated by reference in its entirety).

Catalysts which are polypeptides comprising an amino acid sequence at least 50% identical to SEQ ID NO:1 may comprise one or more amino acid additions, substitutions and/or deletions relative to the amino acid sequence of SEQ ID NO:1. Catalysts may comprise one or several amino acid additions, substitutions and/or deletions relative to the amino acid sequence of SEQ ID NO:1. Catalysts may comprise 1-150, 1-100, 1-50, 1-20 or 1-10 amino acid additions, substitutions and/or deletions relative to the amino acid sequence of SEQ ID NO:1.

Catalysts which are polypeptides comprising an amino acid sequence at least 50% identical to SEQ ID NO:7 may comprise one or more amino acid additions, substitutions and/or deletions relative to the amino acid sequence of SEQ ID NO:7. Catalysts may comprise one or several amino acid additions, substitutions and/or deletions relative to the amino acid sequence of SEQ ID NO:7. Catalysts may comprise 1-150, 1-100, 1-50, 1-20 or 1-10 amino acid additions, substitutions and/or deletions relative to the amino acid sequence of SEQ ID NO:7.

Catalysts which are polypeptides comprising an amino acid sequence at least 50% identical to SEQ ID NO:9 may comprise one or more amino acid additions, substitutions and/or deletions relative to the amino acid sequence of SEQ ID NO:9. Catalysts may comprise one or several amino acid additions, substitutions and/or deletions relative to the amino acid sequence of SEQ ID NO:9. Catalysts may comprise 1-150, 1-100, 1-50, 1-20 or 1-10 amino acid additions, substitutions and/or deletions relative to the amino acid sequence of SEQ ID NO:9.

Catalysts of the invention may be variants of the polypeptides shown in any one of SEQ ID NO:s 1, 7 and 9. Variants may differ from the sequences shown in SEQ ID NO:s 1, 7 and 9 by insertion, addition, substitution or deletion of 1 amino acid, 2, 3, 4, 5-10, 10-20, 20-30, 30-50, 50-100, or more than 150 amino acids. Variants may be made using routine molecular cloning methods.

The skilled person is aware of how to make such variants and is aware of factors likely to affect the functional capability of the catalyst. For example the skilled person understands that a variant with relatively few amino acid insertions, additions, deletions and substitutions is relatively more likely to retain the functionality of the catalysts shown in SEQ ID NO:s 1, 7 and 9 than a variant having relatively many amino acid substitutions. The skilled person also understands that a variant having one or more conservative amino acid substitutions is more likely to retain functionality than a variant having one or more non-conservative substitutions.

An alignment of SEQ ID NO:s 1, 7 and 9 is shown in FIG. 18. The information regarding conserved amino acids (shown by *) strongly similar amino acids (shown by :) and weakly similar amino acids (shown by .) between SEQ ID NO:s 1, 7 and 9 as presented in FIG. 18 suggests amino acid positions at which the avoidance of substitutions may be desirable. Amino acid positions that are not conserved, or that are not similar or are only weakly similar, may be more amenable to substitution whilst retaining functionality. Thus the skilled person is able to generate variants of the polypeptides shown in SEQ ID NO:s. The skilled person is able to determine whether a variant polypeptide is suitable for use as a catalyst in accordance with the present invention using for example the methods described herein. Amino acid substitutions may be conservative amino acid substitutions, in which an amino acid of SEQ ID NO:1, SEQ ID NO: 7 or SEQ ID NO:9 is substituted by an amino acid having similar characteristics. For example a hydrophobic amino acid (e.g. Leu) is substituted by another hydrophobic amino acid (e.g. Ile). Amino acids and conservative substitutions are shown in the table below.

| Amino acid | Conservative substitution |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |

| Amino acid | Conservative substitution |
|---|---|
| Ser | Thr |
| Thr | Ser |
| Trp | Tyr |
| Tyr | Trp; Phe |
| Val | Ile; Leu |

Use

The catalyst of the invention may be used as such, for example as a catalyst in an ex vivo, such as in vitro, reaction. An in vitro reaction in this context refers to an extracellular or cell-free reaction.

The catalyst of the invention has been found to have use as a catalyst in a reduction reaction. In one embodiment, the reduction reaction is the reduction of an unsaturated bond, such as an unsaturated carbon-carbon bond, such as an ethylene bond. The catalyst may be said to have hydrogenation activity, or transfer hydrogenation activity. Thus, the catalyst of the invention is generally useful in the reduction of alkenyl-containing compounds, for example to yield the corresponding reduced product.

In one embodiment, the catalyst of the invention finds use as a catalyst in the reduction of a substrate as described herein, such as a compound of formula (I). The catalyst of the invention may be referred to as a reductase. Thus, the catalyst generally finds use in reduction reactions and more specifically hydrogenation reactions. Thus, the catalyst may catalyse a reduction reaction that formally results in the addition of hydrogen across a carbon-carbon double bond (C=C). Typically the source of hydride in the reductions reactions described herein is provided by a cofactor, such as NADH.

In one embodiment, the catalyst of the invention is provided within a cell, for intracellular reaction, as noted above.

In one aspect there is provided the use of the catalyst of SEQ ID NO. 1 as a catalyst, optionally together with a cofactor. In another aspect there is provided the use of the catalyst of SEQ ID NO:7 as a catalyst, optionally together with a cofactor. In a further aspect there is provided the use of the catalyst of SEQ ID NO:9 as a catalyst, optionally together with a cofactor.

In one embodiment, the catalyst has reduction activity, such as hydrogenation activity, such as hydrogenation of a carbon-carbon double bond (C=C).

In one embodiment, the catalyst has ene reductase activity.

In one embodiment, the catalyst of the invention finds use in a method as described herein.

Methods

In one aspect the present invention provides a method of synthesis, the method comprising the step of reacting a substrate in the presence of the catalyst of the invention thereby to provide a product. The method may comprise contacting the substrate with the catalyst.

The method may be a reduction, and therefore the substrate is reduced in the presence of a catalyst and a reducing agent.

In one embodiment, the reaction is a stereospecific reaction.

Optionally, the method further comprises the step of isolating the product, such as isolating the product from the catalyst and any remaining substrate. The isolation step may include the isolation of the product from by-products, such as those products that are stereoisomers, including enantiomers, of the product. The isolating step may also include the step of isolating the product from the reaction medium.

In one embodiment, the method comprises the step of isolating the catalyst. The catalyst may be subsequently reused in a further method of the invention, as required.

The catalyst of the invention may allow the preparation of a product, such as a reduced product, in high yield. The worked examples show that the catalyst may be used in a reduction reaction to afford a product with a yield of 50% or more, such as 60% or more.

The methods of the invention may be conducted in water, typically with another solvent ("co-solvent") present. The reaction medium may be monophasic or biphasic.

In one embodiment, the co-solvent is present in an amount of at most 10 vol %, at most 15 vol % or at most 25 vol %.

In one embodiment, the co-solvent is present in an amount of at least 0.5 vol %, at least 1 vol % or at least 2 vol %.

In one embodiment, the co-solvent is present in an amount of around 5 vol %.

The co-solvent may be selected from the group consisting of toluene, xylene, ethanol, isopropanol, diethyl ether, tetrahydrofuran, 2-methyl tetrahydrofuran, ethyl acetate, isopropyl acetate, acetonitrile, methyl tert-butyl ether (MTBE), isopropanol, dimethylformamide (DMF), and dimethyl sulfoxide (DMSO).

In one embodiment, the co-solvent is toluene.

The reaction may be performed in a reaction medium where water is present at very low quantities, such as 5 v/v % or less with respect to the total volume of solvent. This is less preferred.

The reaction may be performed at ambient temperature or at an elevated temperature.

The reaction may be performed at a temperature that is at most 35° C., at most 40° C., at most 45° C. at most 50° C., or at most 55° C. As expected, very high and sustained temperatures are associated with loss of enzymatic activity.

The reaction may be performed at a temperature that is at least 30° C., at least 25° C., at least 20° C., at least 15° C., or at least 0° C.

The inventors have found that optimal results are obtained when the catalyst is used at a temperature that is in a range selected from the upper and lower amounts given above, for example in the range 20 to 45° C. or in the range 20 to 35° C.

A reaction in an aqueous medium may be performed at a pH within a limited range.

In one embodiment, the pH of the reaction medium is at most 8, at most 9 or at most 10.

In one embodiment, the pH of the reaction medium is at least 5, at least 6, at least 6.5 or at least 7.

The inventors have found that optimal results are obtained when the catalyst is used at a pH that is in a range selected from the upper and lower amounts given above, for example in the range pH 6.5 to 8.

The pH of the reaction medium may refer to the pH of the reaction medium at the start of the reaction. Additionally or alternatively, the pH may refer to the pH of the reaction end point of the reaction.

A buffer may be provided in the reaction medium to maintain the pH of the reaction medium with a range selected from the upper and lower values given above.

The present inventors have established that the catalyst of the invention may be used at high substrate concentrations. The worked examples demonstrate the use of the catalyst at substrate concentrations of 300 mM, 750 mM and 1,500 mM. In contrast, the work in US 2010/0035315 demonstrates the use of a biocatalyst only at substrate concentrations of 5 mM at most.

In one embodiment, the substrate is present at a concentration of at least 0.1 mM, at least 0.5 mM, at least 1 mM, at least 5 mM, at least 10 mM, at least 50 mM, at least 100 mM, at least 200 mM, at least 300 mM, at least 400 mM, at least 500 mM, at least 750 mM, at least 1,000 mM, at least 1,500 mM, at least 2,000 mM, at least 2,500 mM, or at least 3,000 mM.

In one embodiment, the substrate is present at a concentration of at most 50 mM, at most 100 mM, at most 200 mM, at most 300 mM, at most 500 mM, at most 1,000 mM, at most 1,500 mM, at most 2,000 mM, at most 2,500 mM, at most 3,000 mM, at most 3,500 mM, at most 4,000 mM, at most 4,500 mM, or at most 5,000 mM.

The inventors have found that optimal results are obtained when the substrate is used at a concentration that is in a range selected from the upper and lower amounts given above, for example in the range 5 mM to 1,500 mM.

The substrate concentration may be in the range 50 mM to 5,000 mM, 50 mM to 3,000 mM, 50 mM to 1,500 mM, 50 mM to 1,000 mM, 50 mM to 500 mM, 100 mM to 5,000 mM, 100 mM to 3,000 mM, 100 mM to 1,500 mM, 100 mM to 1,000 mM, 500 mM to 5,000 mM, 500 mM to 3,000 mM, 500 mM to 1,500 mM, or 500 mM to 1,000 mM In one embodiment, the substrate is present at a concentration of at least 10 mg/L, at least 50 mg/L, at least 100 mg/L, at least 500 mg/L, at least 1,000 mg/L, at least 5 g/L, at least 10 g/L, at least 20 g/L, at least 30 g/L, at least 40 g/L, at least 50 g/L, at least 75 g/L at least 100 g/L, at least 150 g/L, at least 200 g/L, at least 250 g/L, or at least 300 g/L.

In one embodiment, the substrate is present at a concentration of at most 5 g/L, at most 10 g/L, at most 20 g/L, at most 30 g/L, at most 50 g/L, at most 100 g/L, at most 150 g/L, at most 200 g/L, at most 250 g/L, at most 300 g/L, at most 350 g/L, at most 400 g/L, at most 450 g/L, or at most 500 g/L.

The amount of catalyst preparation required in a reaction may be small in relation to the amount of substrate present and low in terms of its concentration in the reaction medium. For example, 0.4 g/L of catalyst preparation may be used.

In one embodiment, the catalyst preparation may be present at a concentration of at most 5 g/L, at most 10 g/L at most 50 g/L, at most 100 g/L.

In one embodiment, the catalyst preparation may be present at a concentration of at least 0.05 g/L, at least 0.10 g/L, at least 0.25 g/L, at least 0.5 g/L, or at least 1.0 g/L.

In one embodiment, the catalyst preparation is present at around 0.4 g/L.

In one embodiment, the catalyst preparation is present at around 0.4 g/L.

As discussed above, the amount of an enzyme can be expressed in terms of its activity using enzyme units, U. U may be determined using the assay described above. Similarly, the concentration of an enzyme may be expressed as U/mL.

In one embodiment, the enzyme may be present at a concentration of at most 500 U/mL, at most 300 U/mL, at most 200 U/mL, or at most 150 U/mL. In some embodiments, the enzyme may be present at a concentration of at most 50 U/mL.

In one embodiment, the enzyme may be present at a concentration of at least 1 U/mL, at least 5 U/mL, at least 10 U/mL, or at least 20 Um/L. In some embodiments, the enzyme mat be present at a concentration of at least 50 U/mL.

The inventors have found that optimal results are obtained when the enzyme is used in an amount that is in a range selected from the upper and lower amounts given above.

The amount of enzyme required in a reaction may be small in relation to the amount of substrate present. For example, approximately 70 U of enzyme may be present per mmol of substrate, or approximately 140 U of enzyme may be present per mmol of substrate. For example, 1250 U of enzyme may be present per mmol of substrate.

In one embodiment, the enzyme is present in an amount of at most 5000 U per mmol of substrate, at most 2500 U per mmol of substrate, at most 2000 U per mmol of substrate, or at most 1500 U per mmol of substrate. In some embodiments, the enzyme is present in an amount of at most 500 U per mmol of substrate, at most 300 U per mmol of substrate, or at most 200 U per mmol of substrate.

In one embodiment, the enzyme is present in an amount of at least 1 U per mmol of substrate, at least 10 U per mmol of substrate, at least 20 U per mmol of substrate, at least 40 U per mmol of substrate, or at least 60 U per mmol of substrate.

The inventors have found that optimal results are obtained when the enzyme is used in an amount that is in a range selected from the upper and lower amounts given above.

The reaction may be conducted for sufficient time to allow for the generation of a desirable quantity of material. Subsequently, the reaction mixture may be worked up to isolate the product material.

In one embodiment, the reaction time is at least 1 hour, at least 2 hours, or at least 3 hours.

In one embodiment, the reaction time is at most 18 hours, at most 24 hours, at most 36 hours, at most 48 hours, at most 72 hours, at most 96 hours, or at most 120 hours.

The end of the reaction may be the point at which the catalyst and the product are separated.

The reaction may be deemed complete when the yield of the desired product does not increase substantially over time.

In one embodiment, the reaction is performed in vitro.

The reaction may be performed continuously or discontinuously.

Substrate

The catalyst of the invention may be used as such in the reaction of a substrate. The substrate reacts in the presence of the catalysts to yield a product. The substrate may react with a co-substrate to yield the product.

In one embodiment, the substrate is a compound having functionality that may be reduced. The product of the reaction is therefore a reduced product.

In one embodiment, the substrate has an ethylene bond (C=C). The product of the reaction may be substrate having a reduced ethylene bond, for example —CH—CH—.

In one embodiment the ethylene bond is an activated ethylene bond. Thus, the ethylene bond may be $\alpha,\beta$ to an activating group. Examples of activating groups include acyl, carboxy, acyloxy, nitro, acylamino and nitrile groups. The substrate may therefore have an $\alpha,\beta$-unsaturated acyl, acyloxy, nitro, acylamino or nitrile group.

In one embodiment the ethylene bond is an activated ethylene bond. Thus, the ethylene bond may be $\alpha,\beta$ to an activating group. Examples of activating groups include acyl, carboxy, acyloxy, nitro, or acylamino groups. The substrate may therefore have an $\alpha,\beta$-unsaturated acyl, acyloxy, nitro, or acylamino group.

In one embodiment, the substrate is a compound of formula (I):

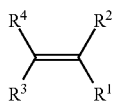

where:
- —R¹ is independently selected from acyl, carboxy, acyloxy, nitro, acylamino, and nitrile;
- —R² is independently selected from hydrogen, alkyl, alkenyl, alkynyl, cycloalkyl, heterocyclyl, aryl, amino, hydroxyl and oxy, and —R² is optionally further selected from amido or nitrile;
- —R³ is hydrogen, alkyl, alkenyl, alkynyl, cycloalkyl, heterocyclyl, aryl, amino, hydroxyl, oxy, carboxy, acyloxy, nitrile and acylamino,
- or where —R¹ is acyl, acyloxy or acylamino, —R¹ and —R² may form a ring containing the acyl, acyloxy or acylamino group or —R¹ and —R³ may form a ring containing the acyl, acyloxy or acylamino group; and
- —R⁴ is hydrogen, alkyl, alkenyl, alkynyl, cycloalkyl, heterocyclyl, aryl, amino, hydroxyl, oxy, carboxy, acyloxy, nitrile and acylamino, and each alkyl, alkenyl, alkynyl, cycloalkyl, heterocyclyl, and aryl group is optionally substituted;
- or —R² and —R⁴ may together form an unsubstituted or substituted ring.

In one embodiment, R¹ is independently selected from the group consisting of acyl, carboxy, acyloxy, nitro and acylamino.

In one embodiment, —R¹ is acyl or acyloxy. The inventors have established that substrates having such groups present at —R¹ are reduced in good yield and/or with high enantiomeric excess in the presence of the catalyst of the invention.

In one embodiment, —R¹ is acylamino.

In one embodiment —R² is hydrogen. In this embodiment, —R³ and —R⁴ may differ. Where this is the case, the inventors have found that the reduction reaction provides a product having a particularly high enantiomeric excess.

In one embodiment —R² is unsubstituted or substituted alkyl, for example unsubstituted alkyl.

In one embodiment, —R² together with —R⁴ and the carbon atoms to which they are attached form an unsubstituted or substituted carbocyclic ring, such as an unsubstituted or substituted carbocyclic ring. For example, the ring may be a cyclopentene or cyclohexene ring, such as an unsubstituted or substituted cyclohexene ring. The ring may optionally include a heteroatom.

In one embodiment, —R² is amido, for example where —R¹ is acyloxy.

In one embodiment, where —R¹ is acyl, acyloxy or acylamino group, —R¹ and —R² may form a ring containing the acyl, acyloxy or acylamino group. In this embodiment, the carbon-carbon double bond is exo to the ring. The ring may have 4-7 ring atoms, such as 5 or 6 ring atoms.

Where —R¹ is acyloxy one ring atom is an oxygen atom, and where —R¹ is acylamino, one ring atom is a nitrogen atom.

In one embodiment, —R¹ and —R², together with the carbon atom to which they are attached (the α carbon), form a cyclopentenone or cyclohexenone ring. Here, —R¹ is acyl.

Where —R¹ and —R² form a ring, that ring is optionally substituted.

In one embodiment, —R³ is selected from hydrogen, and unsubstituted or substituted alkyl, cycloalkyl, alkenyl, and alkynyl.

In one embodiment, —R³ is hydrogen.

In one embodiment, —R³ is selected from unsubstituted or substituted alkyl, cycloalkyl, alkenyl, and alkynyl.

In one embodiment, —R³ is selected from unsubstituted or substituted alkyl.

In one embodiment, where —R¹ is acyl, acyloxy or acylamino group, —R³ and —R¹ form an unsubstituted or substituted ring containing the acyl, acyloxy or acylamino group. The ring may have 4-7 ring atoms, such as 5 or 6 ring atoms. For example, the ring may be a cyclopentenone or cyclohexenone ring.

The ring may optionally include a heteroatom. The ring may be provided with an oxo (═O) substituent to a ring carbon atom. An oxo-substituted carbon ring atom may join with an acylamino group to form a cyclic imide (—C(O)—NR—C(O)—). Such structures are shown to be active substrates in the present of SYE-4 enzyme (see Iqbal et al.), for example. In one embodiment, —R³ and —R¹ form an unsubstituted or substituted ring when —R¹ contains an acyl group.

Where an alkenyl or alkynyl group is present in any of —R², —R³ and —R⁴ it is preferably not conjugated with the unsaturated bond that is α,β to the group —R¹.

In one embodiment, —R⁴ is selected from hydrogen and unsubstituted or substituted alkyl, cycloalkyl, alkenyl, and alkynyl. In one embodiment, —R⁴ is hydrogen.

In one embodiment, one of —R², —R³ and —R⁴ is not hydrogen.

In one embodiment, one of —R², —R³ and —R⁴ is hydrogen. For example, —R² is hydrogen or —R³ is hydrogen.

In one embodiment, R³ and —R⁴ are hydrogen.

In one embodiment, the substrate is not 12-oxo-cis-10, 15-phytodienoate.

The inventors have found that ENE-103 has little activity for the substrates 3-methyl-2-cyclopentenone and 3-methyl-2-cyclohexenone. However, this little activity is believed to be associated with these specific substrates, and ENE-103 exhibits catalyst activity with other structurally related substrates, as shown in the worked examples of the present case.

In one embodiment, the substrate is not 3-methyl-2-cyclopentenone or 3-methyl-2-cyclohexenone, for example where the catalyst is a polypeptide comprising an amino acid sequence having at least 70% identity to SEQ ID NO: 9, such as where the polypeptide comprises an amino acid sequence of SEQ ID NO: 9.

In one embodiment, —R⁴ is hydrogen. In one embodiment, —R² is independently selected from alkyl, alkenyl, alkynyl, cycloalkyl, heterocyclyl, aryl, amino, hydroxyl and oxy. These embodiments may apply where —R¹ is acyl, and —R¹ and —R³ together form a ring containing the acyl group, such as a cyclopentenone ring.

In one embodiment, the substrate does not contain a nitrile (—CN) group. For example, each of —R¹, —R³ and —R⁴ is not nitrile. Accordingly, the group —R¹ may be independently selected from acyl, carboxy, acyloxy, nitro, and acylamino. The group —R³ may be independently selected from hydrogen, alkyl, alkenyl, alkynyl, cycloalkyl, heterocyclyl, aryl, amino, hydroxyl, oxy, carboxy, acyloxy, and acylamino, The group —R⁴ may be independently selected hydrogen, alkyl, alkenyl, alkynyl, cycloalkyl, heterocyclyl, aryl, amino, hydroxyl, oxy, carboxy, acyloxy, and acylamino.

An alkyl group may refer to a $C_{1-20}$ saturated alkyl group, which is linear or branched. The alkyl group may be a $C_{1-4}$, $C_{1-6}$ or a $C_{1-10}$ alkyl group. Examples of alkyl groups include methyl, ethyl, propyl and 1-methylethyl (iso-propyl).

An alkenyl group may refer to a $C_{2-20}$ alkenyl group, which is linear or branched. The alkenyl group may be a $C_{2-4}$, $C_{2-6}$ or a $C_{2-10}$ alkenyl group. Examples of alkenyl groups include ethenyl and propenyl. Where the alkenyl group is provided with a substituent, an ethylene of the group may be provided $\alpha,\beta$ to the substituent. An alkenyl group may possess one or more unsaturated bonds.

An alkynyl group may refer $C_{2-20}$ alkynyl group, which is linear or branched. The alkynyl group may be a $C_{2-4}$, $C_{2-6}$ or a $C_{2-10}$ alkynyl group. Examples of alkynyl groups include ethynyl and propynyl. An alkynyl group may possess one or more unsaturated bonds.

A cycloalkyl group may refer to a $C_{6-10}$ cycloalkyl group. Examples of alkyl groups include cyclohexyl and cyclopentyl.

In one embodiment, the cycloalkyl group is optionally unsaturated.

The cycloalkyl group may be part of a fused ring system. In a fused system the cycloalkyl group has a ring system comprising two or more fused rings, wherein one ring of the fused ring system may be an aromatic ring (including a hetero aromatic ring), and the group is attached to the rest of the molecule by a non-aromatic ring atom (i.e., a ring atom that is part of a non-aromatic ring that is part of the ring system). Thus, the fused ring system is connected via a ring atom of the cycloalkyl ring. Examples of fused systems include tetralinyl and indanyl. The fused ring system may be optionally substituted at any available ring atom.

A heterocyclyl group may refer to a $C_{5-10}$ heterocyclyl group. The heterocyclyl group may be a $C_{5-7}$, $C_{5-6}$ or a $C_6$ heterocyclyl group. The heterocycle group contains one or more, such as one or two heteroatoms selected from N, O and S. The heterocyclyl group may be connected via a ring carbon atom or a ring nitrogen atom, where present. A nitrogen ring atom may be a group NH, or the nitrogen ring atom may be substituted. A sulfur ring atom may be a group —S—, —S(O)— or —S(O)$_2$—.

Examples of heterocyclyl groups include tetrahydrofuran, tetrahydrothiophene, pyrrolidine, 1,4-dioxane, morpholine, thiomorpholine, piperazine, piperidine and 1,4-diazepine.

The heterocyclyl group may be part of a fused ring system. In a fused system the heterocyclyl group has a ring system comprising two or more fused rings, wherein one ring of the fused ring system may be an aromatic ring (including a hetero aromatic ring), and the group is attached to the rest of the molecule by a non-aromatic ring atom (i.e., a ring atom that is part of a non-aromatic ring that is part of the ring system). Thus, the fused ring system is connected via a ring atom of the heterocyclyl ring. Examples include indolinyl, indolyl, dihydrobenzofurnayl, chromanyl, and 2,3-dihydro-1,4-benzodioxinyl. The fused ring system may be optionally substituted at any available ring atom.

An aryl group may refer to a $C_{5-14}$ carboaryl or heteroaryl group.

A carboaryl group may be a $C_{6-14}$ or a $C_{6-10}$ carboaryl group.

Examples of carboaryl groups include phenyl and naphthyl.

The carboaryl group may be part of a fused ring system. In a fused system the carboaryl group has a ring system comprising two or more fused rings, wherein at least one ring of the fused ring system is an aromatic ring (including a hetero aromatic ring), and the group is attached to the rest of the molecule by an aromatic ring atom (i.e., a ring atom that is part of an aromatic ring that is part of the ring system). Thus, the fused ring system is connected via a ring atom of the aromatic ring. Examples include napthyl, indolinyl, indolyl, and dihydrobenzofurnayl, chromanyl, and 2,3-dihydro-1,4-benzodioxinyl. The fused ring system may be optionally substituted at any available ring atom.

A heteroaryl group may be a $C_{5-14}$, $C_{5-10}$, or $C_{5-6}$ heteroaryl group.

Examples of heteroaryl groups include furanyl, pyrrolyl, imidazolyl, oxazolyl, thiazolyl, pyridonyl, pyrazinyl, quinolinyl, and iso-quinolinyl.

The heteroaryl group may be part of a fused ring system. In a fused system the heteroaryl group has a ring system comprising two or more fused rings, wherein at least one ring of the fused ring system is a heteroaromatic ring, and the group is attached to the rest of the molecule by an ring atom in the heteroaromatic ring (i.e., a ring atom that is part of an aromatic ring that is part of the ring system). Thus, the fused ring system is connected via a ring atom of the aromatic ring. The heteroaryl group may be connected via a ring carbon atom or a ring nitrogen atom, where present. Examples include indolyl, benzolfuranyl, isobenzofuanryl, benzoxazoyl, purinyl, quinolinyl, and iso-quinolinyl.

The alkyl, alkenyl, alkynyl cycloalkyl, heterocyclyl, and aryl, groups are optionally substituted. A group may be mono-, di- or tri-substituted.

Where a group is said to be substituted it may be substituted with a substituent independently selected from the group consisting of halo, hydroxyl (—OH), nitro (—NO$_2$), alkyl, alkenyl, alkynyl, cycloalkyl, heterocyclyl, aryl, oxy, thio, amino, acyl, carboxy, acyloxy, oxyacyl, amido, and acylamino. These groups are discussed below.

Where a nitrogen ring atom is present in a heterocycle group that ring atom may be unsubstituted (NH) or optionally substituted with alkyl, alkenyl, alkynyl cycloalkyl, heterocyclyl, aryl, acyl, and acyloxy, such as described herein.

A halo, hydroxyl (—OH), nitro (—NO$_2$), alkyl, alkenyl, alkynyl, cycloalkyl, heterocyclyl, aryl, oxy, thio, amino, acyl, carboxy, acyloxy, oxyacyl, amido, and acylamino group may be a group as described below.

An acyl group is a group —C(O)H or —C(O)R, where —R is selected from substituted or unsubstituted alkyl, alkenyl, alkynyl, cycloalkyl, heterocyclyl, and aryl.

In one embodiment, an acyl group is —C(O)R.

Where an acyl group is a substituent to a nitrogen ring atom, the acyl group together with the nitrogen ring atom form an amido group.

In one embodiment, where —$R^1$ is an acyl group, —R is selected from substituted or unsubstituted alkyl.

In one embodiment, where —$R^1$ is an acyl group that group may be part of a ring formed together with the group —$R^3$. For example, —$R^1$ and —$R^3$, together with the carbon atoms to which they are attached, may form a cyclohex-2-ene-1-one or cyclopent-2-en-1-one ring.

A carboxy group is —C(O)OH or the carboxylate form of this group.

An acyloxy group is a group —C(O)OR, where —R is selected from substituted or unsubstituted alkyl, alkenyl, alkynyl, cycloalkyl, heterocyclyl, and or aryl.

Where an acyl group is a substituent to a nitrogen ring atom, the acyloxy group together with the nitrogen ring atom form a carbamate group.

The group —$R^1$ may be an acyloxy group. In one embodiment, —R may together with —$R^3$ form a ring. In one embodiment, —$R^6$ and —$R^3$ and the atoms to which they are attached form an unsubstituted or substituted ring, where the ring has 4-8, such as 5-7, ring atoms. The ring may be a cyclohexene or a cyclopentene ring, for example. The ring is optionally substituted.

In one embodiment, where —$R^1$ is an acyloxy group, —R is selected from substituted or unsubstituted alkyl.

A halo group is independently selected from —F, —Cl, —I and —Br.

An oxy group is a group —OR, where R is independently selected from alkyl, alkenyl, alkynyl, cycloalkyl, heterocyclyl, and aryl.

A thio group is a group —SH or SR, where R is independently selected from alkyl, alkenyl, alkynyl, cycloalkyl, heterocyclyl, and aryl.

An amino group is a group selected from —$NH_2$, —NHR, and —$N(R)_2$, where each R is independently selected from alkyl, alkenyl, alkynyl, cycloalkyl, heterocyclyl, and aryl, such as alkyl, cycloalkyl, and aryl.

An oxyacyl group is a group —OC(O)R, where —R is independently selected from substituted or unsubstituted alkyl, alkenyl, alkynyl, cycloalkyl, heterocyclyl, and aryl.

An amido group is a group —NHC(O)R, —NRC(O)R where —R is independently selected from substituted or unsubstituted alkyl, alkenyl, alkynyl, cycloalkyl, heterocyclyl, and aryl, such as substituted or unsubstituted alkyl.

An acylamino group is a group —C(O)$NH_2$, —C(O)NHR or —C(O)$N(R)_2$, where —R is independently selected from substituted or unsubstituted alkyl, alkenyl, alkynyl, cycloalkyl, heterocyclyl, and aryl, or two R groups may together with the nitrogen atom to which they are attached from a substituted or unsubstituted nitrogen heterocycle, optionally containing one further ring heteroatom. The heterocycle is optionally substituted with alkyl, alkenyl, alkynyl, cycloalkyl, heterocyclyl, and aryl.

Described above is the group —R, which is selected from substituted or unsubstituted alkyl, alkenyl, alkynyl, cycloalkyl, heterocyclyl, and aryl.

In one embodiment, —R, where present, is selected from substituted or unsubstituted alkyl, alkenyl, alkynyl and cycloalkyl.

In one embodiment, —R, where present, is selected from substituted or unsubstituted alkyl and cycloalkyl, such as alkyl.

In one embodiment, —R, where present, is selected from substituted or unsubstituted alkyl, alkenyl and aryl.

In one embodiment, —R, where present, is substituted or unsubstituted aryl.

An alkyl, alkenyl, or alkynyl group is not substituted with an alkyl, alkenyl, or alkynyl group.

Each substituent may be optionally further substituted.

In one embodiment, —$R^3$ and —$R^4$ are not the same. In one embodiment, —$R^2$, —$R^3$ and —$R^4$ are not the same.

In one embodiment, —$R^2$, —$R^3$ and —$R^4$ do not contain an ethylene group that is $\alpha,\beta$ to an activating group, such as $\alpha,\beta$ to an acyl, carboxy, acyloxy, or nitro group. Here, the substrate has only one activated ethylene group and that is the ethylene group that is $\alpha,\beta$ to —$R^1$.

In one embodiment, the substrate is a compound having a molecular weight of at most 500, at most, 750, or at most 1,000.

In one embodiment, the substrate is achiral.

Co-Substrate

In the methods of the invention the substrate may react together with a co-substrate to yield a product. In a reduction reaction, the co-substrate may be regarded as the reducing agent. The reducing agent may formally provide hydrogen for the reduction. The reducing agent is typically a co-factor.

Cofactor

The catalyst may use NAD(P)H as a cofactor to provide reducing equivalents for the reduction reaction. For example in catalysing the reduction of unsaturated carbon-carbon double bonds the catalyst may use reducing equivalents from NAD(P)H, thereby oxidising it to NAD(P)$^+$. The ratio of reduced cofactor to oxidised cofactor, for example the ratio of NAD(P)H to NAD(P)$^+$, should be relatively high in order to favour cofactor oxidation and concomitant reduction of substrate.

Cofactors are also known as coenzymes, and may also be known as cosubstrates The term "NAD(P)H" is used to indicate NADH and/or NADPH, and the term and "NAD(P)$^+$" is used to indicate NAD$^+$ and/or NADP$^+$. For example a catalyst that uses "NAD(P)H" as a cofactor may use NADH as a cofactor and may additionally or alternatively use NADPH as a cofactor.

In in vitro reactions, the reduced cofactor may be present in a stoichiometric amount with the substrate. Alternatively, the reduced cofactor may be present in significantly less than a stoichiometric amount with the substrate. The reduced cofactor may be regenerated using a reduced cofactor regenerating system, which reduces the cofactor oxidised during the reaction and thereby allows the cofactor to be present in significantly less than a stoichiometric amount with the substrate. Reduced cofactor regeneration systems are known in the art. Such systems may comprise a reducing agent optionally together with an enzyme capable of transferring reducing equivalents from the reducing agent to the oxidised cofactor. Reducing agents include sugars, in particular hexoses such as glucose, mannose, fructose, reducing agents also include oxidisable alcohols such as ethanol, propanol, and isopropanol, and reducing agents also include formate, phosphite and molecular hydrogen. Such systems may comprise a sugar as a reducing agent optionally with a compatible sugar dehydrogenase to catalyse the transfer of reducing equivalents from the sugar to the oxidised cofactor. For NADH as cofactor, a reduced cofactor regenerating system may comprise glucose and glucose dehydrogenase (GDH), as shown in Scheme 1. For NADH as cofactor, a reduced cofactor regenerating system may comprise formate and formate dehydrogenase. For NADPH as cofactor, a cofactor regeneration system may include glucose-6-phosphate and glucose-6-phosphatase.

In in vivo reactions, when the catalyst is provided in a cell, reduced NAD(P)H is regenerated by intracellular enzymes. Such enzymes may be endogenous or recombinant. For example intracellular enzymes involved in glycolysis such as glyceraldehyde phosphate dehydrogenase may reduce NAD$^+$ to NADH.

The catalyst may be a flavin-dependent enzyme. That is, the catalyst may accept reducing equivalents from a cofactor to reduce an unsaturated carbon-carbon double bond via a flavin mononucleotide (FMN) prosthetic group.

Stereoselective Reaction

The catalyst of the invention may be used to generate products where one or more, such as two, carbon atoms in the product has a specific stereochemistry. Thus, the catalyst of the invention may be used advantageously to prepare chiral compounds.

The catalyst of the invention may be used to generate a product having an ee value of 70% or more, 80% or more, 95% or more, 99% or more.

Accordingly the catalyst of the invention may be used to prepare products that are predominantly of one stereoisomer, with a low quantity of another stereoisomer, such as an enantiomer.

The catalyst of the invention may be used together with a substrate that is achiral. Thus, the substrate may not possess atoms having stereogenic centres. The methods described herein allow for the generation of one or two stereogenic centres in the product. Thus, the catalyst of the invention may be used to impart chirality from an achiral starting material.

It is noted that the reaction methods described herein are not limited to stereoselective methods of synthesis. As shown in the worked examples, the catalyst of the invention may be used to generate high yields of reduced substrate. The stereoselective reduction of a substrate may occur with or without high yields of product.

Where the substrate contains an ethylene bond, the reduction of that bond, using the catalyst, is understood to occur with the formal addition of hydrogen on opposite faces (anti) of the bond. In the compound of formula (I), the ethylene bond is shown with the group —$R^1$ located at the bottom right. As drawn, reduction of this bond in the presence of the catalyst may occur with the addition of a hydrogen atom from the top face (above the plane of the paper) at the carbon bonded to —$R^3$ and —$R^4$, and the addition of a hydrogen atom from the bottom face (below the plane of the paper) at the carbon bonded to —$R^1$ and —$R^2$.

Thus, the in one embodiment, the reduction of the compound of formula (I) occurs thus:

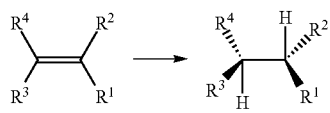

The amount of an enantiomer or ratio of enantiomers in a product may be determined by standard spectroscopic techniques, such as HPLC using a chiral stationary phase. As described herein the ee value for a product of a reduction reaction was determined by GC analysis of a product mixture.

The inventors have found that high enantiomeric excesses may be obtained where the carbon atom to which —$R^3$ and —$R^4$ are attached is a pro-chiral carbon atom (a carbon atom which becomes a chiral carbon atom upon reduction). In contrast, where the carbon atom to which —$R^1$ and —$R^2$ are attached (the α carbon) is a pro-chiral carbon atom, in some cases high enantiomeric excesses are not achieved. This is believed to be due to the higher relative lability of the hydrogen atom attached to the α carbon following reduction, which can lead to racemization reactions were the α carbon is a chiral carbon atom (e.g. via the enolate form where —$R^1$ is acyl). Accordingly, where a high enantiomeric excess is desired, it may be preferred that the carbon atom to which —$R^3$ and —$R^4$ are attached is a pro-chiral carbon atom. It may be preferred that the carbon atom to which —$R^1$ and —$R^2$ are attached is not a pro-chiral carbon atom.

In particular, the inventors have found that high enantiomeric excesses may be obtained for those compounds where —$R^2$ is hydrogen and —$R^3$ and —$R^4$ are each not hydrogen and are not the same. Here, the carbon to which —$R^3$ and —$R^4$ are attached may be regarded as a pro-chiral centre, as it will become a chiral carbon atom upon reduction. In contrast, the α carbon that is to —$R^1$ will not yield a quaternary stereogenic centre upon reduction, as the reaction will result in this carbon atom bearing two hydrogen atoms.

The skilled person will readily understand the term chiral carbon atom as used herein. It includes a carbon atom having four different groups attached thereto, one of which may be a hydrogen atom.

Kits

In one aspect the present invention provides the catalyst of the invention in a kit.

The kit may comprise one or more further catalysts. A further catalyst may be for use in a reduction reaction, such as the reduction of an ethylene group as described herein.

Additionally or alternatively, a further catalyst may be for use in a reaction that is not a reduction reaction, or is not the reduction of an ethylene group.

In one embodiment the further catalysts are biocatalysts. Thus, each catalyst has enzymatic activity.

A catalyst may be spatially separated from other catalysts or other components of the kit. Thus, a catalyst may be provided in a well of a well plate, or in a separate vial or other container.

A kit of the present invention may be a kit having a reduction catalyst together with one or more other catalysts, wherein the reduction catalyst is a polypeptide comprising an amino acid sequence having at least 70% identity to SEQ ID NO: 1. It may be a kit having a reduction catalyst together with one or more other catalysts, wherein the reduction catalyst is a polypeptide comprising an amino acid sequence having at least 70% identity to SEQ ID NO: 7. It may be a kit having a reduction catalyst together with one or more other catalysts, wherein the reduction catalyst is a polypeptide comprising an amino acid sequence having at least 70% identity to SEQ ID NO: 9.

The kit may be provided with instructions for use of the kit. Optionally the kit may be provided with additional reagents for use with a catalyst. For example, co-factors, buffers, solvents, and so on may be provided. A buffer may be provided in concentrated form, for later rehydration.

One or all of the further catalysts may be an enzyme catalyst.

In one embodiment, the kit further comprises one or more catalysts having an activity selected from the group consisting of transferase activity, hydrolase activity, lyase activity, isomerase activity, and ligase activity.

In one embodiment, the kit further comprises one or more catalysts having an activity selected from the group consisting of lipase activity, esterase activity, amidase activity (including peptidase activity), glycosidase activity, glycoltransferase activity, epoxidase activity, nitrilase activity (including nitrile hydratase activity), hydroxylation activity, dehydrogenase activity (including alcohol dehydrogenase activity), dihydroxylation activity, Baeyer-Villiger oxidation activity, aldolase activity, oxynitrilase activity, amino-transferase activity and cofactor regenerating activity.

Additionally or alternatively, the kit comprises a catalyst having an activity that is an ene reductase activity.

In one embodiment, the kit is provided with a substrate for one or each of the catalyst in the kit. The substrate may be provided as a reference substrate, for example to establish the activity of the catalysts within the kit.

In one embodiment, the kit is provided with instructions for the use of each catalyst.

Other Embodiments

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXPERIMENTAL

Catalyst

ENE-101 was expressed in *E. coli* using standard expression techniques. The nucleic acid sequence optimised for expression of ENE-101 in *E. coli* (SEQ ID NO:3) was cloned into a standard expression vector for IPTG-inducible expression.

In some experiments nucleic acid sequences (non-codon optimised) encoding ENE-101 having one or more N-terminal tags (SEQ ID NO: 5 and SEQ ID NO: 7) were expressed and confirmed to have catalytic activity.

ENE-101 preparations were produced by harvesting cells, recovering biomass and resuspending the biomass in buffer (0.1 M potassium phosphate, pH 7.0), lysing the suspension and removing the cell debris to provide a clarified cell lysate. In some experiments the lysis buffer contained 20 μm FMN (flavin mononucleotide) and 5 mM $MgSO_4$. The inclusion of 20 μm FMN and 5 mM $MgSO_4$ in the lysis buffer resulted in a 10% increase in ENE-101 activity. The clarified cell lysate was filtered first through filters of 0.5 μm and 0.2 μm pore size, and then further concentrated by ultrafiltration to provide an ENE-101 preparation. Such ENE-101 preparations may be used directly or lyophilised for subsequent reconstitution and use. The ENE-101 preparations typically comprise about 5 U $mg^{-1}$ of catalyst, determined by the assay described above, using 1-octene-3-one as the reference substrate.

For activity studies, ENE-101 preparations were made using a vector expressing SEQ ID NO:3.

Described below is the use of a catalyst of SEQ ID NO:1. This is referred to as ENE-101.

Experimental Procedure 1

50 μL of a solution of lyophilised ENE-101 preparation in water (100 mg/mL; 5 mg enzyme per test) was added to reaction vials containing 900 μL of aqueous media at pH 7 (250 mM potassium phosphate buffer pH 7, 1.1 mM NAD+, 30 mM D-glucose, 10 U/mL GDH) and 50 μL of substrate solution in toluene (400 mM, final concentration of substrate 20 mM). The vials were shaken at 35° C. for 3, 6 and 18 hours. After adding 1 mL of EtOAc the reaction vials were vortexed and centrifuged. Samples of the organic phase were analysed by GC to measure conversion and ee.

The results are shown in Table 1.

The conversion values in some experiments were found to be relatively low under the specific reaction conditions employed. However, no side products were observed, and unreacted substrate was the main component remaining. Assuming that the substrate may be recovered and reused in subsequent reactions, the yield of the product may be regarded as relatively high.

TABLE 1

Reaction Time, Conversion and ee for Substrates in Experimental Procedure 1

| Entry | Substrate | Time (h) | % Conv [a] | % ee | Stereo. [c] |
|---|---|---|---|---|---|
| 1 | 3-methylcyclopent-2-enone | 3 | 2.7 | >99.9 | S |
| 2 | 3-methylcyclopent-2-enone | 6 | 4.0 | >99.9 | S |
| 3 | 3-methylcyclopent-2-enone | 18 | 10.2 | >99.9 | S |
| 4 | 3-methylcyclohex-2-enone | 3 | 4.0 | >99.9 | S |
| 5 | 3-methylcyclohex-2-enone | 6 | 5.7 | >99.9 | S |
| 6 | 3-methylcyclohex-2-enone | 18 | 18.7 | >99.9 | S |
| 7 | 2-methylcyclopent-2-enone | 3 | 91.4 | 51.4 [b] | |
| 8 | 2-methylcyclopent-2-enone | 6 | 100 | 34.6 [b] | |
| 9 | 2-methylcyclopent-2-enone | 18 | 100 | 8.0 [b] | |
| 10 | dimethyl itaconate ($CO_2Me$ / $CO_2Me$) | 3 | 27.6 | >99.9 | |
| 11 | dimethyl itaconate | 6 | 42.2 | >99.9 | |
| 12 | dimethyl itaconate | 18 | 91.1 | >99.9 | |
| 13 | 1-nitrocyclohexene ($NO_2$) | 3 | 97.7 | n.a. | |

TABLE 1-continued

Reaction Time, Conversion and ee for Substrates in Experimental Procedure 1

| Entry | Substrate | Time (h) | % Conv [a] | % ee | Stereo. [e] |
|---|---|---|---|---|---|
| 14 | (1-acetyl-cyclohexene) | 3 | 80.2 | n.a. | |
| 15 | (citral, CHO) | 3 | 72.7 | n.d. [c] | |
| 16 | (β-nitrostyrene) | 18 | 100 | n.a. | |
| 17 | (α-methyl-β-nitrostyrene) | 18 | 91.6 | n.d. [c] | |

[a] Integration of the product peak in the GC (uncorrected GC area).

[b] Erosion of the product ee in the reaction media has been observed; this erosion is not enzymatically-catalysed.

[c] ee has not been determined.

[e] Stereo. refers to the assigned stereochemistry of the product.

Reduction of 3-methyl-2-cyclopentenone (entries 1, 2, and 3) and 3-methyl-2-cyclohexenone (entries 4, 5 and 6) proved slow and only partial conversion was obtained in both cases. Enantioselectivity was excellent for both substrates.

2-Methyl-2-cyclopentenone, on the other hand, proved very active and reacted fast. Note that the corresponding product, 2-methylcyclopentanone, racemises under the reaction conditions.

FIG. 1 shows the changes in % conversion with the change in reaction time (h.) for four of the substrates listed in Table 1.

Concentration Study

Those substrates that proved more active with ENE-101 were subsequently tested at three different concentrations: 50, 100 and 300 mM. Experimental Procedure 1 was followed for these tests. The amount of glucose, ENE-101, GDH and NAD were scaled up according to substrate concentration so the number of equivalents remained constant. As described in the experimental procedure above, a 250 mM phosphate buffer pH 7.0 was used for the reactions. No attempt was made to regulate pH as the reactions took place. This means that at high substrate concentrations the gluconic acid produced may not be fully neutralised, therefore making the pH of the media too acidic for the ENE-101 to work.

The results are shown in Table 2.

TABLE 2

Reaction Time, Conversion and ee for Substrates with Change in Concentration

| Entry | Substrate | Time (h) | Cc (mM) | % Conv [a] | % ee |
|---|---|---|---|---|---|
| 1 | 2-methyl-2-cyclopentenone | 3 | 50 | 50.79 | 65.8 [b] |
| 2 | | 3 | 100 | 59.18 | 68.1 [b] |
| 3 | | 3 | 300 | 33.84 | 61.3 [b] |
| 4 | | 18 | 50 | 70.08 | 14.9 [b] |
| 5 | | 18 | 100 | 67.16 | 26.8 [b] |
| 6 | | 18 | 300 | 36.37 | 16.0 [b] |
| 7 | dimethyl itaconate | 3 | 50 | 15.8 | >99.9 |
| 8 | | 3 | 100 | 14.9 | >99.9 |
| 9 | | 3 | 300 | 12.7 | >99.9 |
| 10 | | 18 | 100 | 46.3 | >99.9 |
| 11 | | 18 | 300 | 17.6 | >99.9 |
| 12 | nitrocyclohexene | 3 | 50 | 60.3 | n.a. |
| 13 | | 3 | 100 | 60.4 | n.a. |
| 14 | | 3 | 300 | 43.1 | n.a. |
| 15 | | 18 | 50 | 52.8 | n.a. |
| 16 | | 18 | 100 | 68.5 | n.a. |
| 17 | | 18 | 300 | 39.4 | n.a. |

TABLE 2-continued

Reaction Time, Conversion and ee
for Substrates with Change in Concentration

| Entry | Substrate | Time (h) | Cc (mM) | % Conv[a] | % ee |
|---|---|---|---|---|---|
| 18 | (cyclohexenyl methyl ketone) | 3 | 50 | 6.5 | n.a. |
| 19 | | 3 | 100 | 18.5 | n.a. |
| 20 | | 3 | 300 | 24.1 | n.a. |
| 21 | | 18 | 50 | 7.3 | n.a. |
| 22 | | 18 | 100 | 49.9 | n.a. |
| 23 | | 18 | 300 | 23 | n.a. |
| 24 | (citral, CHO) | 3 | 50 | 60.8 | n.d.[c] |
| 25 | | 3 | 100 | 76.6 | n.d.[c] |
| 26 | | 3 | 300 | 43.6 | n.d.[c] |
| 27 | | 18 | 50 | 92.4 | n.d.[c] |
| 28 | | 18 | 100 | 81.2 | n.d.[c] |
| 29 | | 18 | 300 | 52.3 | n.d.[c] |

[a] Integration of the product peak in the GC (uncorrected GC area).
[b] Erosion of the product ee in the reaction media has been observed; this erosion is not enzymatically-catalysed.
[c] ee was not determined.

Figure 2:
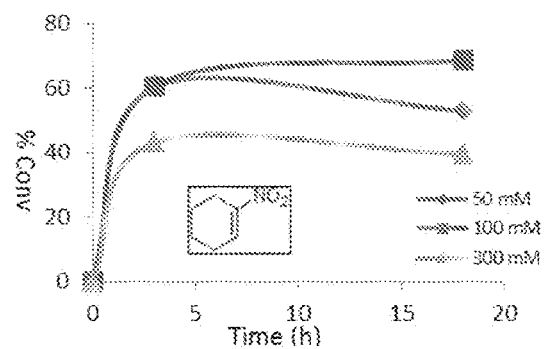
FIG. 2 shows the change in percentage conversion of a series of substrates (shown) to their reduced forms (not shown) over time (hours) at different substrate concentration, using a catalyst according to an embodiment of the invention. Each substrate was used at 50 mM (diamonds), 100 mM (squares) and 300 mM (triangles).
Figure 2:
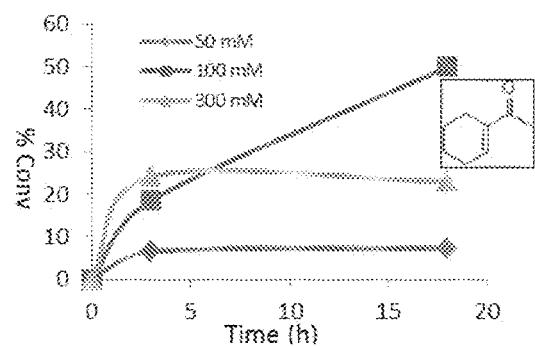
Figure 2:
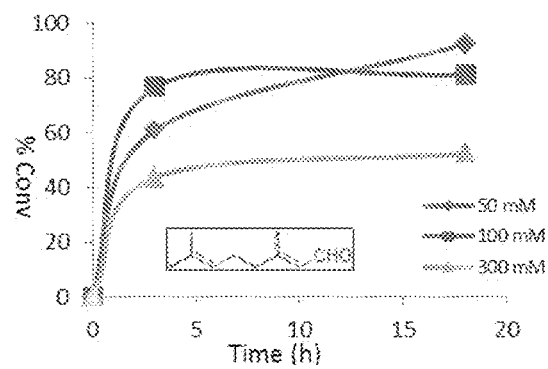

FIG. 2 shows the changes in % conversion with the change in reaction time (h.) and change in substrate concentration for three of the substrates listed in Table 1.

For most of the substrates tested it is noted that conversion did not improve significantly when the reaction time was increased from 3 to 18 hours. This was particularly remarkable at high substrate concentrations and indicates that the pH of the reaction media turned too acidic for the enzyme to work, causing conversion to stop. This was proven by measuring the pH of the reaction vials after 3 and 18 hours.

In none of the examples tested was there evidence of product or substrate inhibition even at concentrations as high as 300 mM. This indicates that running these reductions at concentrations up to 300 mM (maybe even higher) should be possible, and ideally together with control of reaction media pH.

pH Study

Figure 3:
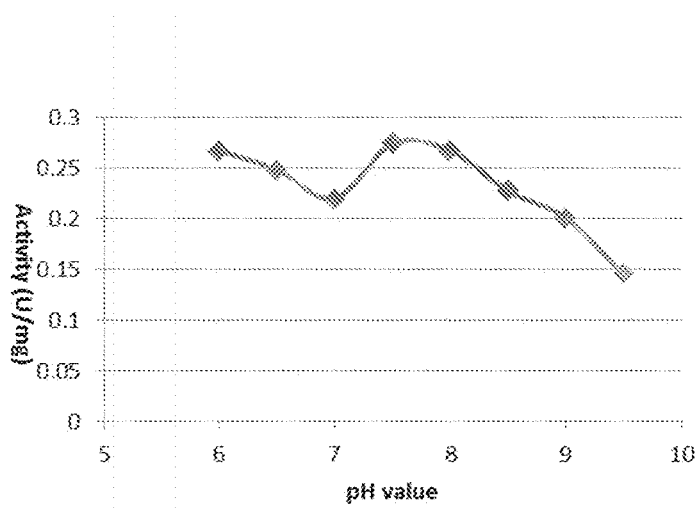
FIG. 3 shows the change in catalyst activity (U/mg) with change in the pH of the reaction medium using a catalyst according to an embodiment of the invention. The substrate citral was used.

In the pH study citral (3,7-dimethyl-2,6-octadienal) was chosen as test substrate for further studies. The effect of the pH of the buffer was then studied and the results are shown in FIG. 3.

The pH of the reaction mixture was assumed to remain substantially constant throughout the reaction procedure in view of the short reaction time (typically around 1 minute).

The reactivity was determined by photometric assay—the decrease in absorbance at 340 nm caused by the oxidation of NADH is a measure of the catalytic activity of ENE-101. Assay concentrations: in 1 mL reaction mix, the final concentrations are 0.1 M potassium phosphate pH 7.4, 10 mM substrate, 15 mM NADH and 0.4 mg of ENE-101.

The background activity (decrease of NADH absorbance in the absence of substrate) was measured for each pH value. It was found to be higher for pH 6 to 6.5 and for pH 8 to 9. ENE-101 was found to be stable and more active between pH 6.5 to 8.

Temperature Profile and Stability

Figure 4:
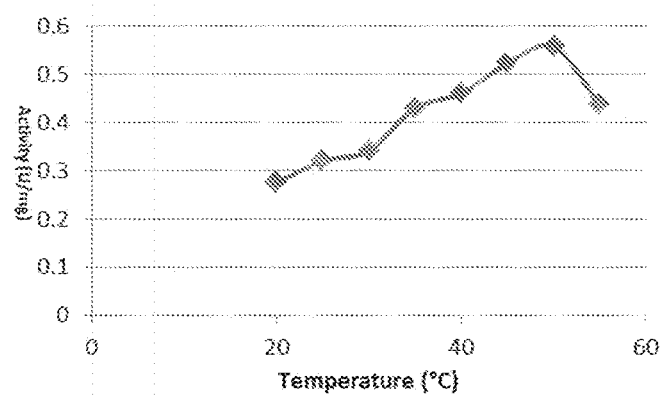
FIG. 4 shows the change in catalyst activity (U/mg) with change in the reaction temperature (° C.) using a catalyst according to an embodiment of the invention. The substrate citral was used.

The temperature profile of ENE-101 was also studied and the background activity was measured for each temperature and subtracted from the enzymatic measured activity. The results are shown in FIG. 4.

The reactivity was determined by photometric assay as described above in relation to the pH study. The substrate was citral.

Figure 5:
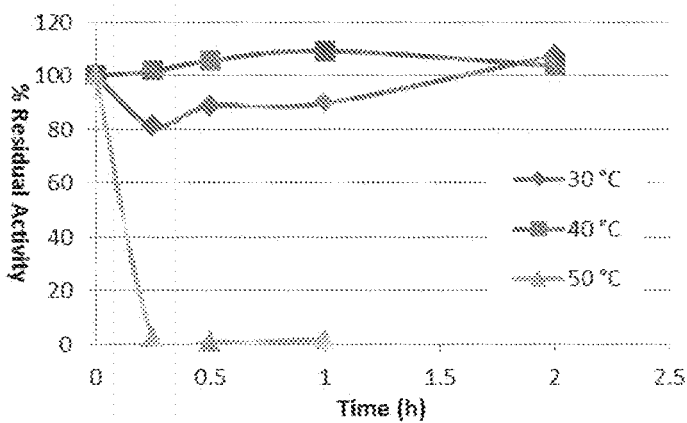
FIG. 5 shows the change in residual activity (U/mg) with time (hours) at different reaction temperatures using a catalyst according to an embodiment of the invention. The reaction was performed at 30° C. (diamonds), 40° C. (squares) and 50° C. (triangles).

The stability of ENE-101 was studied at three different temperatures (30, 40 and 50° C.). As before, the background activity was measured and removed. Results of residual activity are shown in FIG. 5. Again, the reactivity was determined by photometric assay and the substrate was citral.

The results in FIG. 5 indicate that ENE-101 is reasonably stable at temperatures below 40° C. but rapidly losses activity at 50° C.

Solvent and Additive Effect

Figure 6:
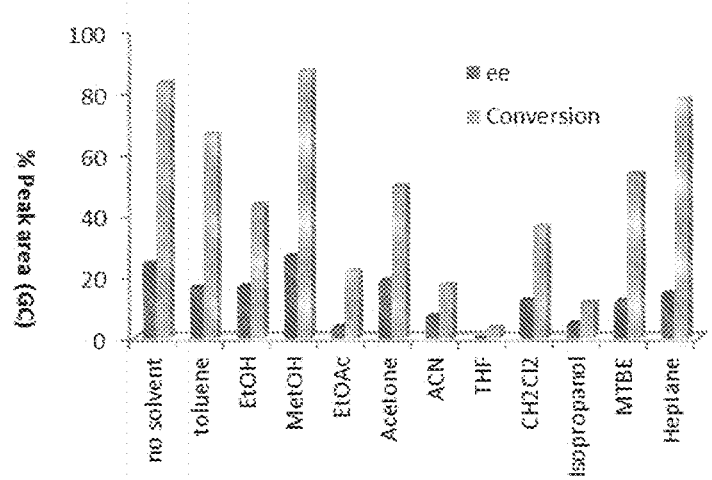
FIG. 6 shows the change in percentage conversion of a substrate (% peak area as determined by GC; light shading) and the change in ee of the reduced product (dark shading) with changes in the reaction medium co-solvent using a catalyst according to an embodiment of the invention. Each co-solvent was used at 5 vol %.

The solvent and additive effects were studied using the relatively reactive substrate, 2-methyl-2-cyclopentenone. Different co-solvents were compared at 5 vol % following Experimental Procedure 1. The results from this comparison in relation to yield and ee of the product are shown in FIG. 6.

As mentioned before, the product of the reduction, 2-methylcyclopentanone, racemises under the reaction conditions. Among the co-solvents tested none of them seem to improve conversion or prevent racemization to a significant degree.

Figure 7:
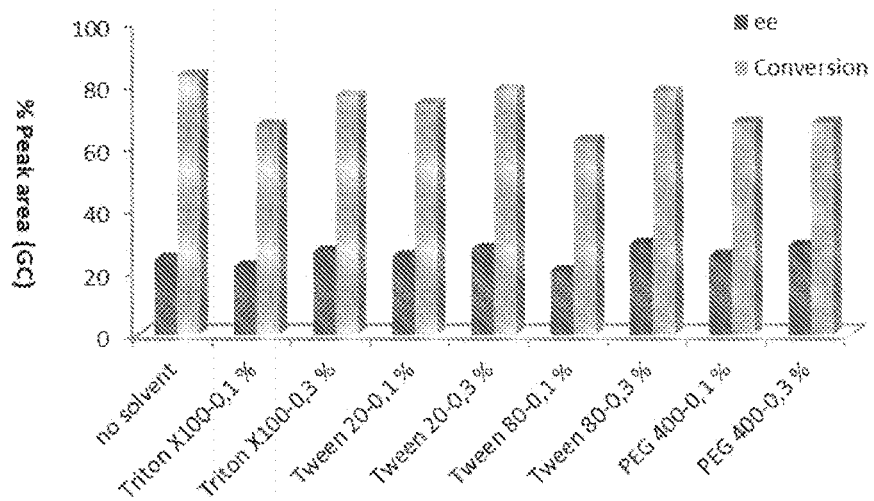
FIG. 7 is shows the change in percentage conversion of a substrate (% peak area as determined by GC; light shading) and the change in ee of the reduced product (dark shading) with changes in the additive to the reaction medium co-solvent using a catalyst according to an embodiment of the invention. Each surfactant was used at 0.1 or 0.3 vol %.

Under identical conditions, the effect surfactant addition (at 0.1 and 0.3 vol %) to the reaction mixture was evaluated. The results are shown in FIG. 7.

Among the co-solvents tested at the indicated volumes, none of them seem to improve conversion or prevent racemization to a significant degree.

Scale-Up Experiments

The catalysis reactions were subsequently performed on a larger scale to show the utility of the catalyst at an industrially useful level.

A scale up reaction looked at the reduction, as shown in Scheme 1 below.

Scheme 1

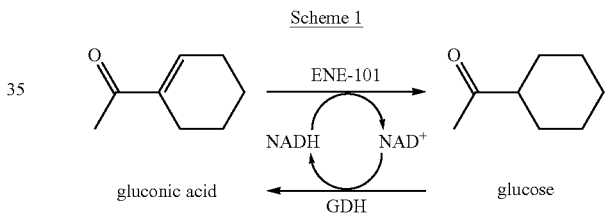

Procedure 1—Reagents and Method

| | MW | Weight (g) | Mmol | Cc. (M) | Comment |
|---|---|---|---|---|---|
| D-glucose•H$_2$O | 198.17 | 8.2 | 41.4 | 0.826 | 10% excess |
| NaCl | 58.44 | 1.68 | 28.7 | 0.575 | |
| NAD$^+$ | 663.43 | 0.17 | 0.25 | 0.005 | |
| 1-Acetyl-cyclohexene | 124.18 | 4.67 | 37.6 | 0.752 | Substrate not fully dissolved |
| ENE-101 | | 1.0 | | | 21% weight of substrate |
| GDH | | 0.1 | | | |
| KH$_2$PO$_4$ | 136.09 | 0.03 | 0.2 | 0.004 | |
| K$_2$HPO$_4$ | 174.18 | 0.6 | 3.4 | 0.0685 | |
| NaOH | 40 | | 37.6 | 0.752 | |

In a magnetically stirred (600 rpm, egg-shaped stirring bar) 50 mL round bottom flask, temperature controlled (40° C.) and equipped with a pH controlled dosing pump, were introduced de-ionised water (36.3 mL), K$_2$HPO$_4$ (597 mg) and KH$_2$PO$_4$ (27 mg). This resulted in a 0.1 M phosphate buffer solution pH 8.0. D-glucose monohydrate (8.2 g) was then added, causing the pH of the solution to drop to 7.1. After the temperature stabilised, NaCl (1.68 g) was added followed by ENE-101 (1.0 g), GDH (103 mg; 4.88 U/mg; 500 U), NAD (166 mg) and 1-acetylcyclohexene (4.67 g; 37.6 mmol).

The reaction was stirred at 40° C. until full conversion was observed by GC analysis. In order to maintain a constant pH 7.0 the reaction was dosed with a 45% NaOH solution.

Figure 8:
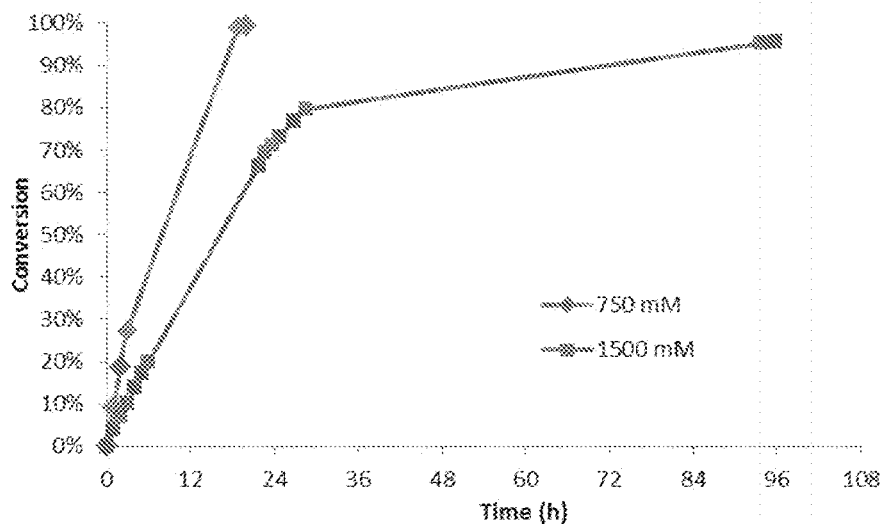
FIG. 8 shows the change in percentage conversion of a substrate over time (hours) at different substrate concentrations. The substrate was used at 750 mM (diamonds) and 1,500 mM (squares).
Figure 9:
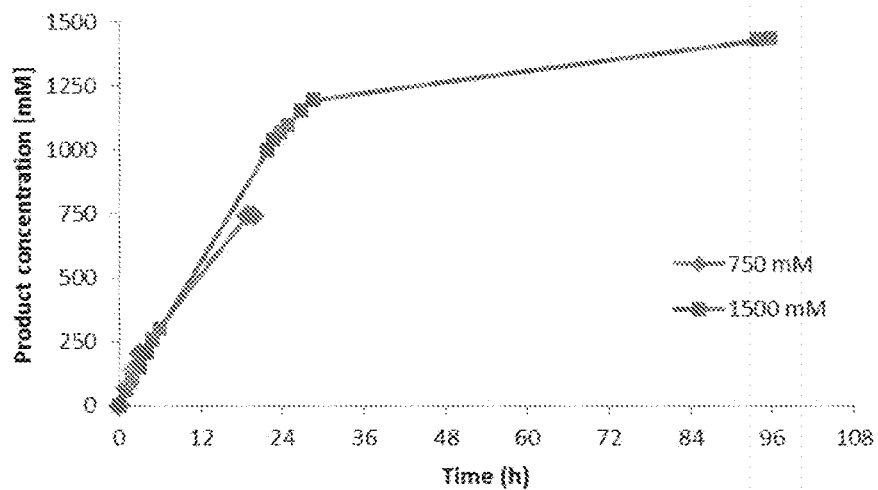
FIG. 9 shows the change in product concentration (mM) over time (hours) at different substrate concentrations. The substrate was used at 750 mM (diamonds) and 1,500 mM (squares).

To monitor conversion samples (50 μL) were taken from the reaction at regular intervals. They were treated with DCM (1.5 mL), vortexed, centrifuged to eliminate insoluble materials and analysed by GC to measure conversion. After 20 hours 99.3% conversion to product was observed by GC. The reaction profile can be found in FIGS. 8 and 9.

Procedure 2—Reagents and Method

|  | MW | Weight (g) | Mmol | Cc. (M) | Comment |
|---|---|---|---|---|---|
| D-glucose•H$_2$O | 198.17 | 15.4 | 77.7 | 1.554 |  |
| NaCl | 58.44 | 1.68 | 28.7 | 0.575 |  |
| NAD$^+$ | 663.43 | 0.3 | 0.47 | 0.0095 |  |
| 1-Acetyl-cyclohexene | 124.18 | 9.34 | 75.2 | 1.504 | Substrate not fully dissolved |
| ENE-101 |  | 1.0 |  |  | 21% weight of substrate |
| GDH |  | 0.1 |  |  |  |
| KH$_2$PO$_4$ | 136.09 | 0.02 | 0.14 | 0.0028 |  |
| K$_2$HPO$_4$ | 174.18 | 0.4 | 2.3 | 0.047 |  |
| NaOH | 40 |  | 75.2 | 1.504 |  |

The reaction was repeated at double substrate concentration following an identical procedure as described before. On this occasion a solution of D-glucose monohydrate (15.4 g; 77.7 mmol), sodium chloride (1.68 g), NAD (316 mg; 0.47 mmol), GDH (103 mg; 4.88 U/mg; 500 U) and ENE-101 (1.0 g) in phosphate buffer 0.1 M pH 8.0 (24.8 mL) was placed in a magnetically stirred round bottom flask at 40° C. before being treated with 1-acetylcyclohexene (9.34 g; 75.2 mmol). The reaction was stirred at 40° C. for 96 hours. In order to maintain a constant pH 7.0 the reaction was dosed with a 45% NaOH solution.

Samples (25 μL) were taken from the reaction at regular intervals to monitor conversion. They were treated with DCM (1.5 mL), vortexed, centrifuged to eliminate insoluble materials and analysed by GC to measure conversion. After 26 hours 75% conversion to product was observed by GC (1.125 M product concentration). The reaction slowed down and was stopped at 95% conversion. A profile of the reaction can be found in FIGS. 8 and 9.

A further scale up reaction looked at the reduction as shown in Scheme 2 below.

Scheme 2

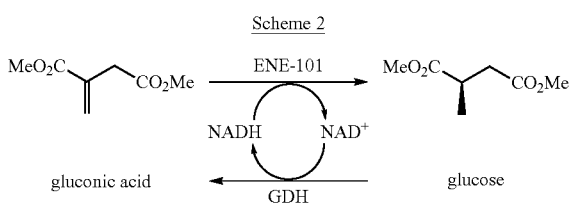

Procedure 3—Reagents and Method

|  | MW | Weight (g) | Mmol | Cc. (M) | Comment |
|---|---|---|---|---|---|
| D-glucose•H$_2$O | 198.17 | 8.2 | 41.4 | 0.826 | 10% excess |
| NaCl | 58.44 | 1.68 | 28.7 | 0.575 |  |

-continued

|  | MW | Weight (g) | Mmol | Cc. (M) | Comment |
|---|---|---|---|---|---|
| NAD$^+$ | 663.43 | 0.17 | 0.25 | 0.005 |  |
| Dimethyl Itaconate | 158.15 | 5.9 | 37.3 | 0.731 | Substrate not fully dissolved |
| ENE-101 |  | 1.0 |  |  | 21% weight of substrate |
| GDH |  | 0.1 |  |  |  |
| KH$_2$PO$_4$ | 136.09 | 0.03 | 0.2 | 0.004 |  |
| K$_2$HPO$_4$ | 174.18 | 0.6 | 3.4 | 0.0685 |  |
| NaOH | 40 |  | 37.6 | 0.752 |  |

In a magnetically stirred (600 rpm, egg-shaped stirring bar) 50 mL round bottom flask, temperature controlled (40° C.) and equipped with a pH controlled dosing pump, were introduced de-ionised water (36.8 mL), K$_2$HPO$_4$ (597 mg) and KH$_2$PO$_4$ (27 mg). This resulted in a 0.1 M phosphate buffer solution pH 8.0. D-glucose monohydrate (8.2 g) was then added, causing the pH of the solution to drop to 7.1. After the temperature stabilized, NaCl (1.68 g) was added followed by ENE-101 (1.0 g), GDH (103 mg; 4.88 U/mg; 500 U), NAD (166 mg) and dimethyl itaconate (5.9 g; 37.3 mmol). The reaction was stirred at 40° C. until full conversion was observed by GC analysis. In order to maintain a constant pH 7.0 the reaction was dosed with a 45% NaOH solution.

Figure 10:
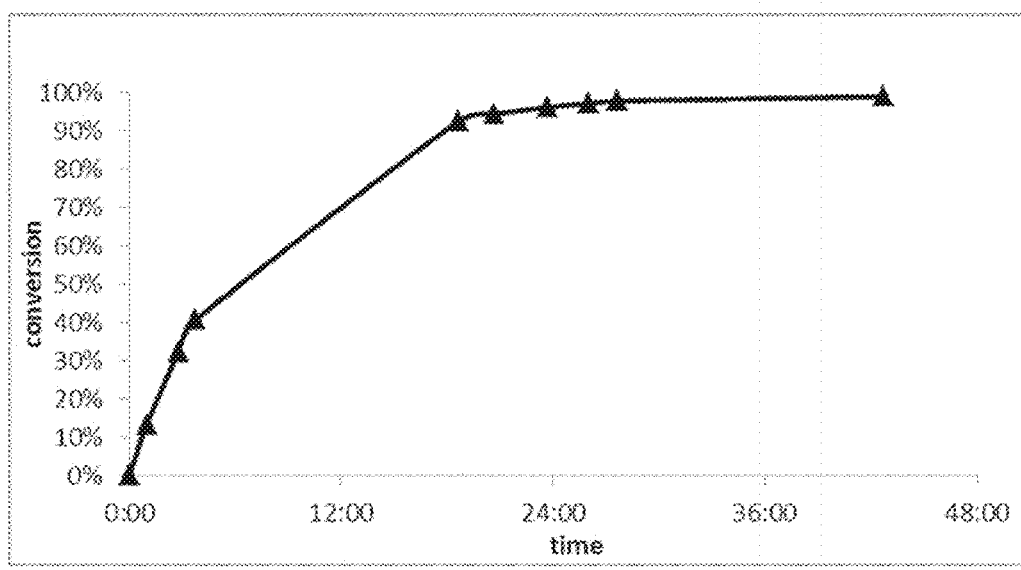
FIG. 10 shows the change in percentage conversion of a substrate over time (hours). The substrate was used at 730 mM.
Figure 11:
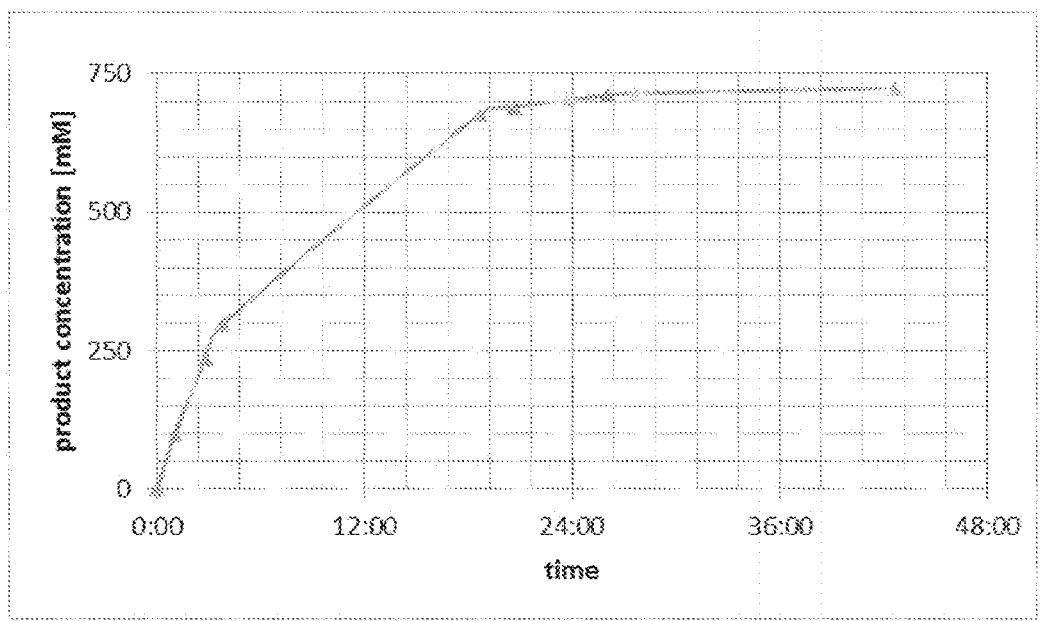
FIG. 11 shows the change in product concentration (mM) over time (hours). The substrate was used at 730 mM.

To monitor conversion samples (50 μL) were taken from the reaction at regular intervals. They were treated with DCM (1.5 mL), vortexed, centrifuged to eliminate insoluble materials and analysed by GC to measure conversion. After 43 hours 99% conversion to product (>99.9% ee, R enantiomer) was observed by GC. The reaction profile can be seen in FIGS. 10 and 11.

Further Experimental Data

Catalyst

ENE-102 and ENE-103 were produced either with a tag (for example, with an N-terminal T7 and His tag) or without tag.

ENE-102 and ENE-103 were produced in a similar way to ENE-101 as described above. The ENE-102 and ENE-103 preparations typically comprise about 1-2 U mg$^{-1}$ of catalyst preparation using NADPH as the cofactor, as generally described by the assay described above, using 1-octene-3-one as the reference substrate.

These further experimental data include data already presented above, for ease of comparison.

To define the substrate scope of enzymes ENE-101, ENE-102 and ENE-103 they were tested against a number of substrates (activated C=C bonds). Reactions were run under identical conditions (as described in "Experimental procedure 2"); samples were taken after 3, 6 and 18 hours and analysed by GC to measure conversion and enantiomeric excess. Results from these reactions are described in Table 3.

Experimental Procedure 2

50 μL of a solution of lyophilised enzyme ENE-101, ENE-102 or ENE-103 preparation in water (100 mg/mL; 5 mg enzyme per test) was added to reaction vials containing 900 μL of aqueous media at pH 7 (250 mM potassium phosphate buffer pH 7, 1.1 mM NAD$^+$, 30 mM D-glucose, 10 U/mL GDH) and 50 μL of substrate solution in toluene (400 mM, final concentration of substrate 20 mM). The vials were shaken at 35° C. for 3, 6 and 18 hours. After adding 1 mL of EtOAc the reaction vials were vortexed and centrifuged. Samples of the organic phase were analysed by GC to measure conversion and ee.

TABLE 3
| Entry | ENE- | Substrate | Time (h) | % Conv [a] | % ee | Stereo |
|---|---|---|---|---|---|---|
| 1 | 101 |  | 3 | 2.7 | >99.9 | S |
| 2 | 101 | | 6 | 4.0 | >99.9 | S |
| 3 | 101 | | 18 | 10.2 | >99.9 | S |
| 4 | 102 |  | 3 | 13.7 | >99.9 | S |
| 5 | 102 | | 6 | 16.4 | >99.9 | S |
| 6 | 102 | | 18 | 37.3 | >99.9 | S |
| 7 | 101 |  | 3 | 4.0 | >99.9 | S |
| 8 | 101 | | 6 | 5.7 | >99.9 | S |
| 9 | 101 | | 18 | 18.7 | >99.9 | S |
| 10 | 102 |  | 3 | 17.0 | >99.9 | S |
| 11 | 102 | | 6 | 25.8 | >99.9 | S |
| 12 | 102 | | 18 | 41.6 | >99.9 | S |
| 13 | 101 |  | 3 | 91.4 | 51.4 [b] | |
| 14 | 101 | | 6 | 100 | 34.6 [b] | |
| 15 | 102 |  | 3 | 100 | 49.2 [b] | |
| 16 | 103 |  | 3 | 94.8 | 71.1 [b] | |
| 17 | 103 | | 6 | 100 | 75.4 [b] | |
| 18 | 101 |  | 3 | 27.6 | >99.9 | R |
| 19 | 101 | | 6 | 42.2 | >99.9 | R |
| 20 | 101 | | 18 | 91.1 | >99.9 | R |
| 21 | 102 |  | 3 | 100 | >99.9 | R |
| 22 | 103 |  | 3 | 60 | >99.9 | R |
| 23 | 103 | | 6 | 76.3 | >99.9 | R |
| 24 | 103 | | 18 | 85.2 | >99.9 | R |
| 25 | 101 |  | 18 | 97.7 | n.a. | |
| 26 | 102 | | 18 | 100 | n.a. | |
| 27 | 103 | | 18 | 100 | n.a. | |
| 28 | 101 |  | 18 | 80.2 | n.a. | |
| 29 | 102 | | 18 | 97.6 | n.a. | |
| 30 | 103 | | 18 | 100 | n.a. | |
| 31 | 101 |  | 18 | 72.7 | n.d. [c] | |
| 32 | 102 | | 18 | 88.8 | n.d. [c] | |
| 33 | 103 | | 18 | 35.9 | n.d. [c] | |

TABLE 3-continued

| Entry | ENE- | Substrate | Time (h) | % Conv [a] | % ee | Stereo |
|---|---|---|---|---|---|---|
| 34 | 101 | Ph-CH=CH-NO₂ | 18 | 100 | n.a. | |
| 35 | 102 | | 18 | 100 | n.a. | |
| 36 | 103 | | 18 | 97.4 | n.a. | |
| 37 | 101 | Ph-CH=C(CH₃)-NO₂ | 18 | 91.6 | n.d. [c] | |
| 38 | 102 | | 18 | 80.5 | n.d. [c] | |
| 39 | 103 | | 18 | 80.9 | n.d. [c] | |
| 40 | 101 | CH₂=C(NHAc)CO₂Me | 18 | 33.0 | n.d. [c] | |
| 41 | 102 | | 18 | 97.7 | n.d. [c] | |
| 42 | 103 | | 18 | 40.1 | n.d. [c] | |

[a] Integration of the product peak in the GC (uncorrected GC area).
[b] Erosion of the product ee in the reaction media has been observed; this erosion is not enzymatically-catalysed.
[c] ee has not been determined.

Reduction of both 3-methyl-2-cyclopentenone and 3-methyl-2-cyclohexenone proved slow and only partial conversion was obtained both with ENE-101 and ENE-102. However, enantioselectivity was excellent for both substrates. ENE-103 was apparently inactive against these substrates (data not shown). This appeared to be an isolated instance of inactivity, as ENE-103 was observed to have activity for structurally related forms, such as 2-methyl-2-cyclopentenone and 1-(cyclohexen-1-yl)ethanone (entries 16 and 17 in Table 3).

2-Methyl-2-cyclopentenone was rapidly reduced by the three enzymes. Unfortunately, the corresponding product, 2-methylcyclopentanone, racemised under the reaction conditions.

It has been reported that α-substituted enones are more readily reduced by old yellow enzymes than β-substituted ones. As examples, see the reports on reductions with *Shewanella* OYE (SYE-4) (Iqbal et al, 2012), enoate reductase from *Zymomonas mobilis* and OYEs from *Kluyveromyces lactis* (KYE1) and from *Yersinia bercovieri* (Yers-ER) (Yanto et al, 2011; Hall et al, 2008).

Figure 12:
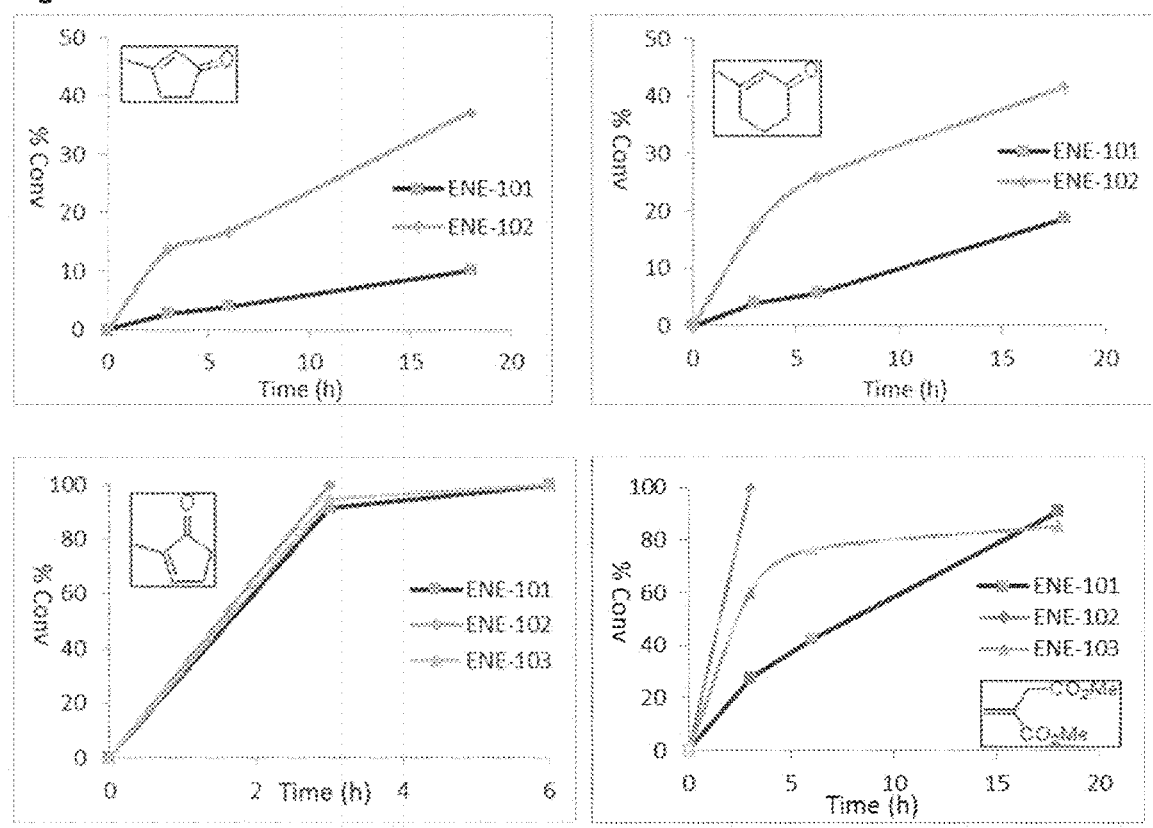
FIG. 12 shows conversion profiles of ENE-101 (squares), ENE-102 (diamonds) and ENE-103 (triangles) for different substrates.

FIG. 12 shows the data reported in Table 3.

Those substrates that proved easier to reduce were subsequently tested at three different concentrations: 50, 100 and 300 mM. Experimental procedure 2 was followed for these tests. The amount of glucose, ENE, GDH and NAD were increased according to substrate concentration so the number of equivalents remained constant. As described in the experimental procedure, a 250 mM phosphate buffer pH 7.0 was used for the reactions. No attempts were made to regulate pH as the reactions took place. This means that at high substrate concentrations the gluconic acid produced may not be fully neutralised, making the pH of the media too acidic for the ENEs to work.

Figure 13A:
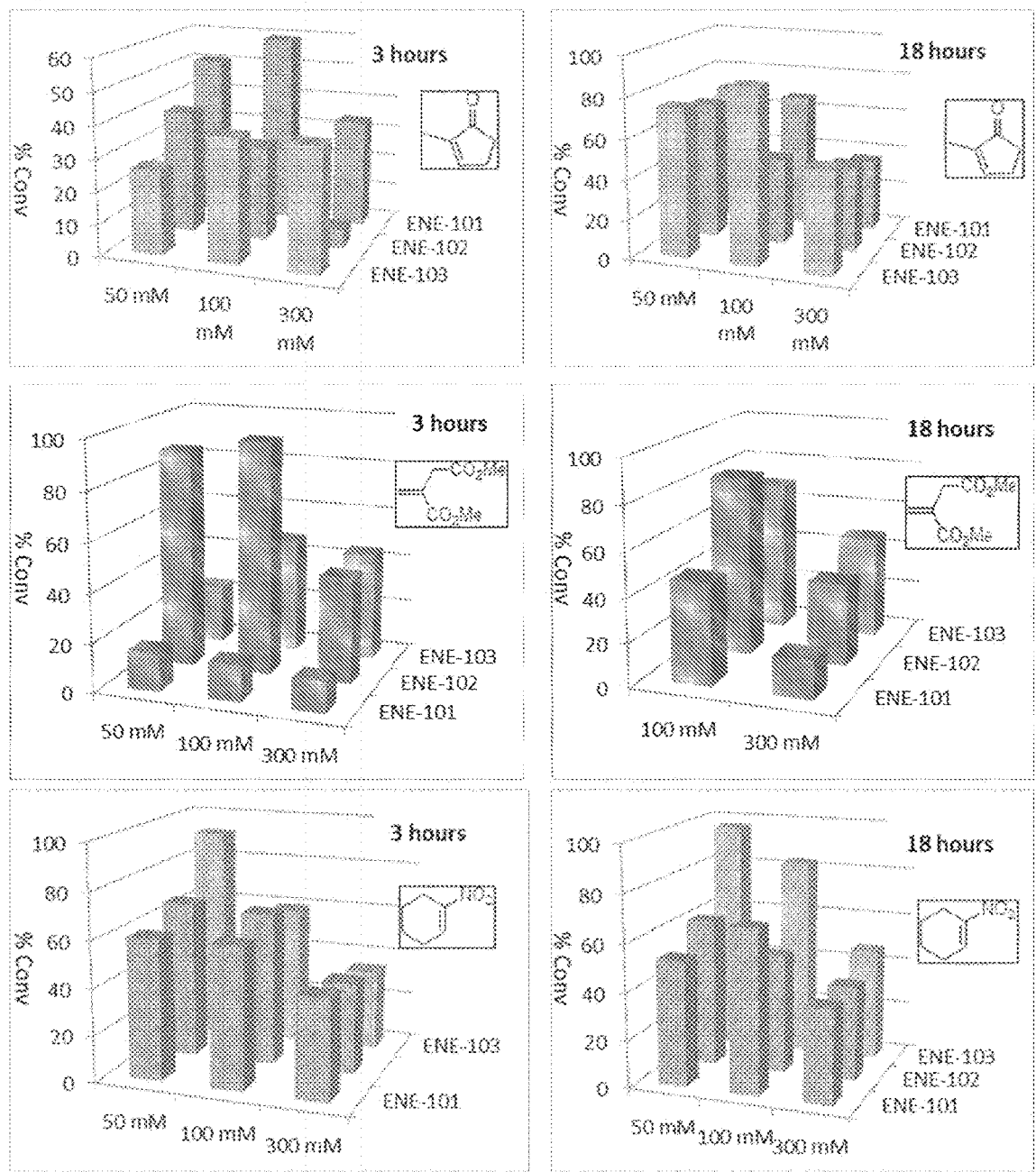
FIGS. 13A and 13B show conversion profiles of ENE-101, ENE-102 and ENE-103 for different substrates at different concentrations.
Figure 13B:
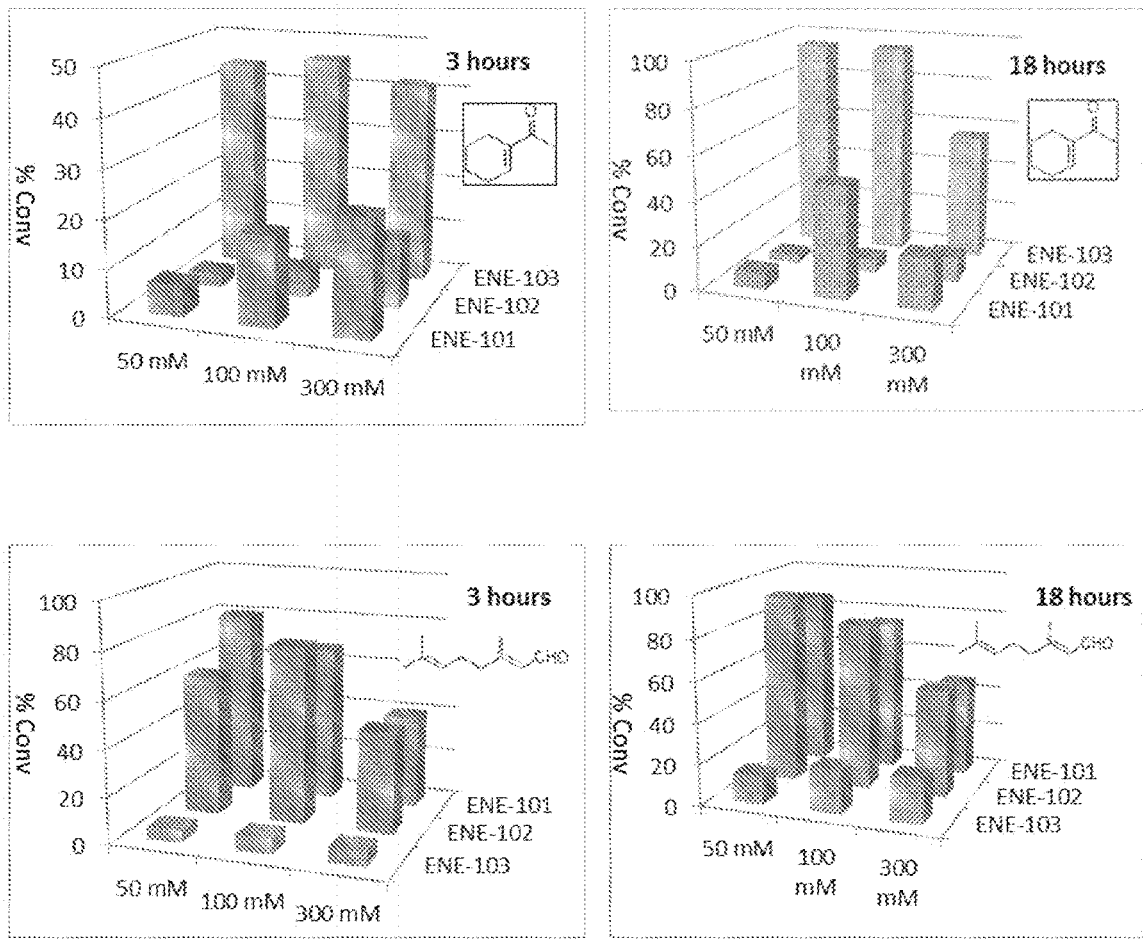

Results from these tests can be found in Table 4 and FIGS. 13A and 13B.

TABLE 4

| Entry | ENE- | Substrate | Time (h) | Cc (mM) | % Conv [a] | % ee |
|---|---|---|---|---|---|---|
| 1 | 101 | 2-methyl-2-cyclopentenone | 3 | 50 | 50.8 | 65.8 [b] |
| 2 | | | 3 | 100 | 59.2 | 68.1 [b] |
| 3 | | | 3 | 300 | 33.8 | 61.3 [b] |
| 4 | | | 18 | 50 | 70.1 | 14.9 [b] |
| 5 | | | 18 | 100 | 67.2 | 26.8 [b] |
| 6 | | | 18 | 300 | 36.4 | 16.0 [b] |
| 7 | 102 | 2-methyl-2-cyclopentenone | 3 | 50 | 38.5 | 66.7 [b] |
| 8 | | | 3 | 100 | 30.0 | 65.3 [b] |
| 9 | | | 3 | 300 | 6.8 | 57.5 [b] |
| 10 | | | 18 | 50 | 68.8 | 38.1 [b] |
| 11 | | | 18 | 100 | 44.1 | 31.8 [b] |
| 12 | | | 18 | 300 | 43.9 | 31.8 [b] |
| 13 | 103 | 2-methyl-2-cyclopentenone | 3 | 50 | 26.4 | 80.3 [b] |
| 14 | | | 3 | 100 | 38.4 | 80.7 [b] |
| 15 | | | 3 | 300 | 38.2 | 79.1 [b] |
| 16 | | | 18 | 50 | 74.5 | 55.2 [b] |
| 17 | | | 18 | 100 | 87.3 | 48.7 [b] |
| 18 | | | 18 | 300 | 51.5 | 67.8 [b] |
| 19 | 101 | CH₂=C(CO₂Me)CH₂CO₂Me | 3 | 50 | 15.8 | >99.9 |
| 20 | | | 3 | 100 | 14.9 | >99.9 |
| 21 | | | 3 | 300 | 12.7 | >99.9 |
| 22 | | | 18 | 100 | 46.3 | >99.9 |
| 23 | | | 18 | 300 | 17.6 | >99.9 |

TABLE 4-continued

| Entry | ENE- | Substrate | Time (h) | Cc (mM) | % Conv [a] | % ee |
|---|---|---|---|---|---|---|
| 24 | 102 | methyl 2-methylenemalonate (CH₂=C(CH₂CO₂Me)CO₂Me) | 3 | 50 | 89.3 | >99.9 |
| 25 | | | 3 | 100 | 100 | >99.9 |
| 26 | | | 3 | 300 | 43.4 | >99.9 |
| 27 | | | 18 | 300 | 37.3 | >99.9 |
| 28 | 103 | dimethyl itaconate | 3 | 50 | 24.1 | >99.9 |
| 29 | | | 3 | 100 | 47.5 | >99.9 |
| 30 | | | 3 | 300 | 44.4 | >99.9 |
| 31 | | | 18 | 100 | 69.7 | >99.9 |
| 32 | | | 18 | 300 | 47.1 | >99.9 |
| 33 | 101 | 1-nitrocyclohexene | 3 | 50 | 60.3 | n.a. |
| 34 | | | 3 | 100 | 60.4 | n.a. |
| 35 | | | 3 | 300 | 43.1 | n.a. |
| 36 | | | 18 | 50 | 52.8 | n.a. |
| 37 | | | 18 | 100 | 68.5 | n.a. |
| 38 | | | 18 | 300 | 39.4 | n.a. |
| 39 | 102 | 1-nitrocyclohexene | 3 | 50 | 67.3 | n.a. |
| 40 | | | 3 | 100 | 65.4 | n.a. |
| 41 | | | 3 | 300 | 39 | n.a. |
| 42 | | | 18 | 50 | 61.9 | n.a. |
| 43 | | | 18 | 100 | 49.8 | n.a. |
| 44 | | | 18 | 300 | 39.5 | n.a. |
| 45 | 103 | 1-nitrocyclohexene | 3 | 50 | 92 | n.a. |
| 46 | | | 3 | 100 | 59.4 | n.a. |
| 47 | | | 3 | 300 | 34.5 | n.a. |
| 48 | | | 18 | 50 | 96.8 | n.a. |
| 49 | | | 18 | 100 | 83.1 | n.a. |
| 50 | | | 18 | 300 | 47 | n.a. |
| 51 | 101 | 1-acetylcyclohexene | 3 | 50 | 6.5 | n.a. |
| 52 | | | 3 | 100 | 18.5 | n.a. |
| 53 | | | 3 | 300 | 24.1 | n.a. |
| 54 | | | 18 | 50 | 7.3 | n.a. |
| 55 | | | 18 | 100 | 49.9 | n.a. |
| 56 | | | 18 | 300 | 23.0 | n.a. |
| 57 | 102 | 1-acetylcyclohexene | 3 | 50 | 2.7 | n.a. |
| 58 | | | 3 | 100 | 5.5 | n.a. |
| 59 | | | 3 | 300 | 14.1 | n.a. |
| 60 | | | 18 | 50 | 3.4 | n.a. |
| 61 | | | 18 | 100 | 5.9 | n.a. |
| 62 | | | 18 | 300 | 11.3 | n.a. |
| 63 | 103 | 1-acetylcyclohexene | 3 | 50 | 44.0 | n.a. |
| 64 | | | 3 | 100 | 46.0 | n.a. |
| 65 | | | 3 | 300 | 41.9 | n.a. |
| 66 | | | 18 | 50 | 94.9 | n.a. |
| 67 | | | 18 | 100 | 95.0 | n.a. |
| 68 | | | 18 | 300 | 56.2 | n.a. |
| 69 | 101 | citral | 3 | 50 | 60.8 | n.d. [c] |
| 70 | | | 3 | 100 | 76.6 | n.d. [c] |
| 71 | | | 3 | 300 | 43.6 | n.d. [c] |
| 72 | | | 18 | 50 | 92.4 | n.d. [c] |
| 73 | | | 18 | 100 | 81.2 | n.d. [c] |
| 74 | | | 18 | 300 | 52.3 | n.d. [c] |
| 75 | 102 | citral | 3 | 50 | 80.3 | n.d. [c] |
| 76 | | | 3 | 100 | 67.6 | n.d. [c] |
| 77 | | | 3 | 300 | 40.2 | n.d. [c] |
| 78 | | | 18 | 50 | 85.9 | n.d. [c] |
| 79 | | | 18 | 100 | 75.0 | n.d. [c] |
| 80 | | | 18 | 300 | 46.8 | n.d. [c] |

TABLE 4-continued

| Entry | ENE- | Substrate | Time (h) | Cc (mM) | % Conv [a] | % ee |
|---|---|---|---|---|---|---|
| 81 | 103 | 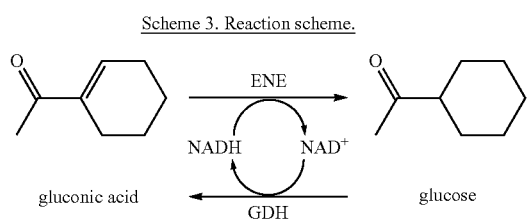 | 3 | 50 | 5.3 | n.d. [c] |
| 82 | | | 3 | 100 | 6.8 | n.d. [c] |
| 83 | | | 3 | 300 | 6.5 | n.d. [c] |
| 84 | | | 18 | 50 | 14.2 | n.d. [c] |
| 85 | | | 18 | 100 | 21.6 | n.d. [c] |
| 86 | | | 18 | 300 | 21.8 | n.d. [c] |

[a] Integration of the product peak in the GC (uncorrected GC area).
[b] Erosion of the product ee in the reaction media has been observed; this erosion is not enzymatically-catalysed.
[c] ee has not been determined.

For most of the substrates tested conversion did not improve significantly when going from 3 to 18 hours reaction time. This was particularly remarkable at high substrate concentrations and indicates that the pH of the reaction media turned too acidic for the enzyme to work, causing conversion to stop. This was proven by measuring the pH of the reaction vials after 3 and 18 hours.

No evidence of product or substrate inhibition was found in any of the experiments, even at concentrations as high as 300 mM. This shows that running these reductions at concentrations up to 300 mM, or higher than 300 mM, may be possible. Regulating the pH of the reaction media may further improve reactions that use high substrate concentrations.

Scale-Up Experiments
Reduction of 1-acetylcyclohexene

Scheme 3. Reaction scheme.

Procedure a.1 (0.75 M)

| | MW | Weight (g) | Mmol | Cc. (M) | Comment |
|---|---|---|---|---|---|
| D-glucose•H$_2$O | 198.17 | 8.2 | 41.4 | 0.826 | 10% excess |
| NaCl | 58.44 | 1.68 | 28.7 | 0.575 | |
| NAD$^+$ | 663.43 | 0.17 | 0.25 | 0.005 | |
| 1-Acetyl-cyclohexene | 124.18 | 4.67 | 37.6 | 0.752 | Substrate not fully dissolved |
| ENE | | 1.0 | | | 21% weight of substrate |
| GDH | | 0.1 | | | |
| KH$_2$PO$_4$ | 136.09 | 0.03 | 0.2 | 0.004 | |
| K$_2$HPO$_4$ | 174.18 | 0.6 | 3.4 | 0.0685 | |
| NaOH | 40 | | 37.6 | 0.752 | |

In a magnetically stirred (600 rpm, egg-shaped stirring bar) 50 mL round bottom flask, temperature controlled (40° C.) and equipped with a pH controlled dosing pump, were introduced de-ionised water (36.3 mL), K$_2$HPO$_4$ (597 mg) and KH$_2$PO$_4$ (27 mg). This resulted in a 0.1 M phosphate buffer solution pH 8.0. D-glucose monohydrate (8.2 g) was then added, causing the pH of the solution to drop to 7.1. After the temperature stabilised, NaCl (1.68 g) was added followed by the ENE (-101, -102 or -103, 1.0 g), GDH (103 mg; 4.88 U/mg; 500 U), NAD (166 mg) and 1-acetyl-cyclohexene (4.67 g; 37.6 mmol).

The reaction was stirred at 40° C. until full conversion was observed by GC analysis. In order to maintain a constant pH 7.0 the reaction was dosed with a 45% NaOH solution.

As for ENE-102 incomplete conversion was obtained at 750 mM, even after prolonged times, the reaction was repeated at 300 mM, resulting in full conversion over-night. For ENE-101 the reaction was repeated at double concentration, 1500 mM.

Procedure a.2 (1.5 M)

| | MW | Weight (g) | Mmol | Cc. (M) | Comment |
|---|---|---|---|---|---|
| D-glucose•H$_2$O | 198.17 | 15.4 | 77.7 | 1.554 | |
| NaCl | 58.44 | 1.68 | 28.7 | 0.575 | |
| NAD$^+$ | 663.43 | 0.3 | 0.47 | 0.0095 | |
| 1-Acetyl-cyclohexene | 124.18 | 9.34 | 75.2 | 1.504 | Substrate not fully dissolved |
| ENE-101 | | 1.0 | | | 21% weight of substrate |
| GDH | | 0.1 | | | |
| KH$_2$PO$_4$ | 136.09 | 0.02 | 0.14 | 0.0028 | |
| K$_2$HPO$_4$ | 174.18 | 0.4 | 2.3 | 0.047 | |
| NaOH | 40 | | 75.2 | 1.504 | |

The reaction was repeated at double substrate concentration following an identical procedure as described before. On this occasion a solution of D-glucose monohydrate (15.4 g; 77.7 mmol), sodium chloride (1.68 g), NAD (316 mg; 0.47 mmol), GDH (103 mg; 4.88 U/mg; 500 U) and ENE-101 (1.0 g) in phosphate buffer 0.1 M pH 8.0 (24.8 mL) was placed in a magnetically stirred round bottom flask at 40° C. before being treated with 1-acetylcyclohexene (9.34 g; 75.2 mmol). The reaction was stirred at 40° C. for 96 hours. In order to maintain a constant pH 7.0 the reaction was dosed with a 45% NaOH solution.

Figure 14:
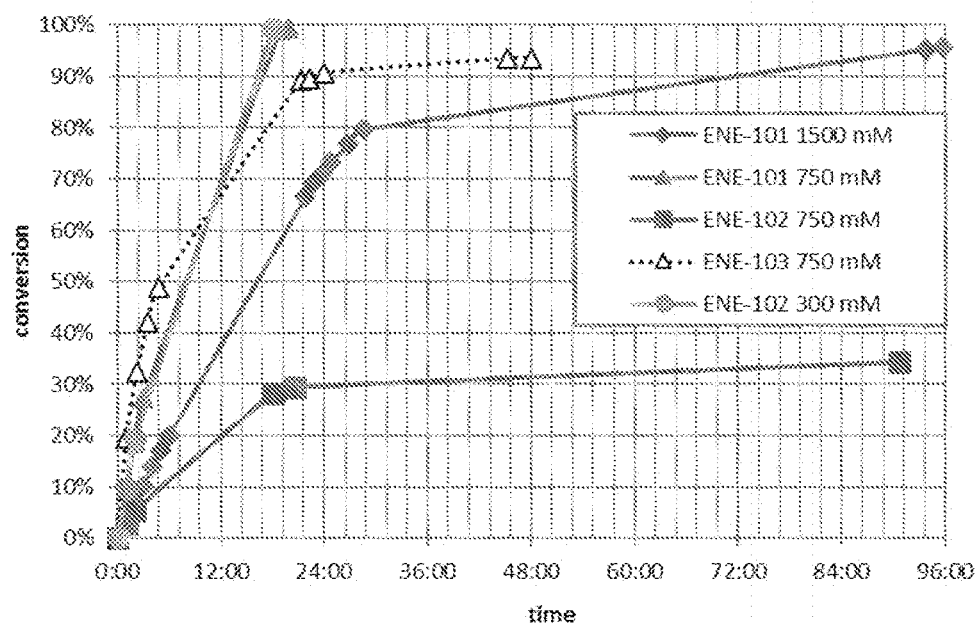
FIG. 14 shows the change in percentage conversion of a substrate over time (hours) for ENE-101, ENE-102 and ENE-103. The substrate was used at 300 mM for ENE-102 (circles), 750 mM for ENE-101 (closed triangles), ENE-102 (squares) and ENE-103 (open triangles) and 1.5M for ENE-101 (diamonds).
Figure 15:
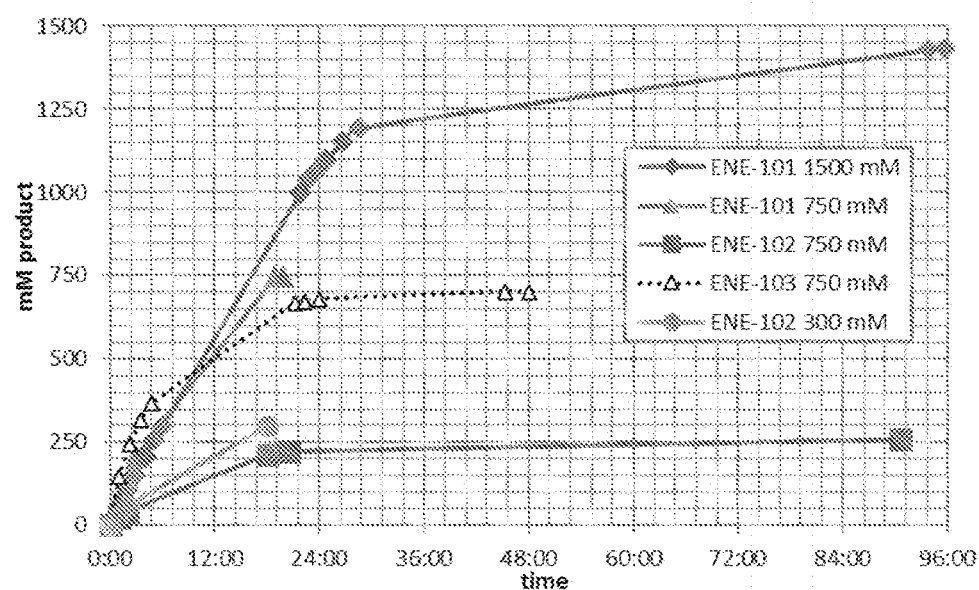
FIG. 15 shows the change in product concentration (mM) over time (hours) for ENE-101, ENE-102 and ENE-103. The substrate was used at 300 mM for ENE-102 (circles), 750 mM for ENE-101 (closed triangles), ENE-102 (squares) and ENE-103 (open triangles) and 1.5M for ENE-101 (diamonds).

To monitor conversion samples (50 μL) were taken from the different reactions at regular intervals. They were treated with DCM (1.5 mL), vortexed, centrifuged to eliminate insoluble materials and analysed by GC to measure conversion. The profiles of the different reactions can be seen in FIGS. 14 and 15.

Reduction of Dimethyl Itaconate

Scheme 4. Reaction scheme.

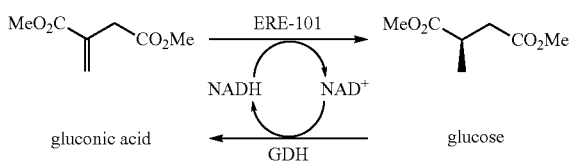

Procedure b.1 (0.73 M)

| | MW | Weight (g) | Mmol | Cc. (M) | Comment |
|---|---|---|---|---|---|
| D-glucose•H$_2$O | 198.17 | 8.2 | 41.4 | 0.826 | 10% excess |
| NaCl | 58.44 | 1.68 | 28.7 | 0.575 | |
| NAD$^+$ | 663.43 | 0.17 | 0.25 | 0.005 | |
| Dimethyl Itaconate | 158.15 | 5.9 | 37.3 | 0.731 | Substrate not fully dissolved |
| ENE | | 1.0 | | | 21% weight of substrate |
| GDH | | 0.1 | | | |
| KH$_2$PO$_4$ | 136.09 | 0.03 | 0.2 | 0.004 | |
| K$_2$HPO$_4$ | 174.18 | 0.6 | 3.4 | 0.0685 | |
| NaOH | 40 | | 37.6 | 0.752 | |

In a magnetically stirred (600 rpm, egg-shaped stirring bar) 50 mL round bottom flask, temperature controlled (40° C.) and equipped with a pH controlled dosing pump, were introduced de-ionised water (36.8 mL), K$_2$HPO$_4$ (597 mg) and KH$_2$PO$_4$ (27 mg). This resulted in a 0.1 M phosphate buffer solution pH 8.0. D-glucose monohydrate (8.2 g) was then added, causing the pH of the solution to drop to 7.1. After the temperature stabilised, NaCl (1.68 g) was added followed by the ENE (−101, −102 or −103, 1.0 g), GDH (103 mg; 4.88 U/mg; 500 U), NAD (166 mg) and dimethyl itaconate (5.9 g; 37.3 mmol).

The reaction was stirred at 40° C. until full conversion was observed by GC analysis. In order to maintain a constant pH 7.0 the reaction was dosed with a 45% NaOH solution.

Figure 16:
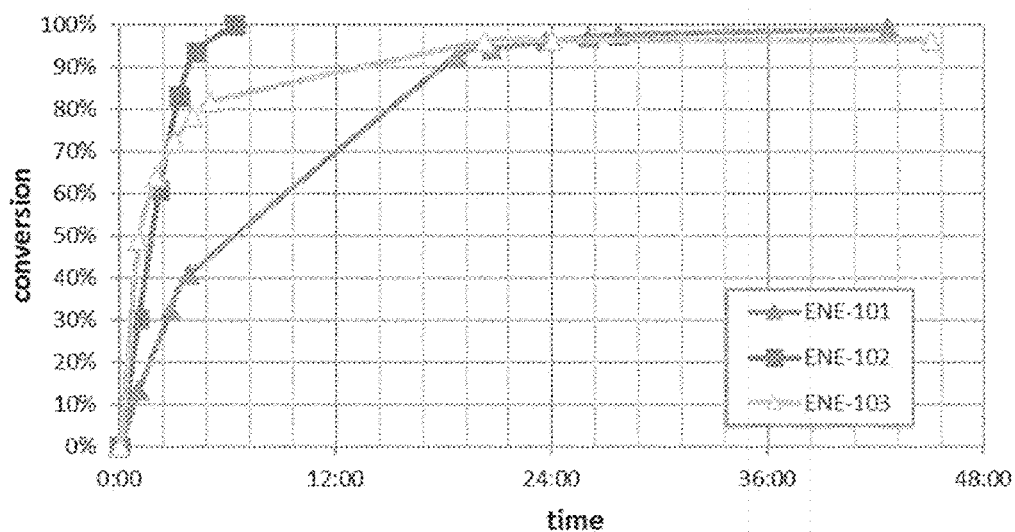
FIG. 16 shows the change in percentage conversion of a substrate over time (hours) for ENE-101 (closed triangles), ENE-102 (squares) and ENE-103 (open triangles). The substrate was used at 730 mM.
Figure 17:
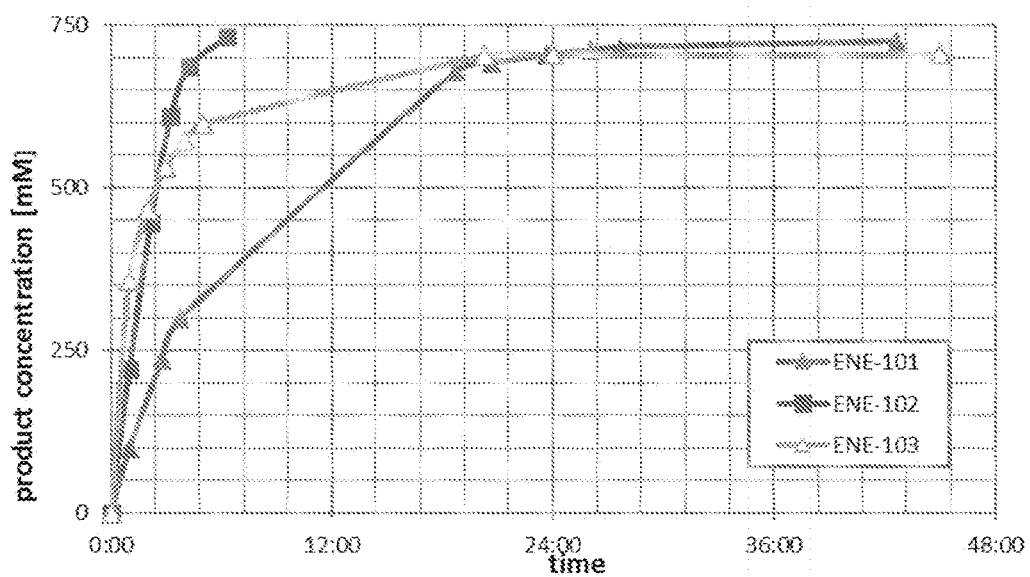
FIG. 17 shows the change in product concentration (mM) over time (hours) for ENE-101 (closed triangles), ENE-102 (squares) and ENE-103 (open triangles). The substrate was used at 730 mM.

To monitor conversion samples (50 μL) were taken from the reaction at regular intervals. They were treated with DCM (1.5 mL), vortexed, centrifuged to eliminate insoluble materials and analysed by GC to measure conversion. Over 95% conversion to product (>99.9% ee, R enantiomer) was observed by GC for the three enzymes. The reaction profile can be seen in FIGS. 16 and 17.

REFERENCES

A number of publications are cited above in order to more fully describe and disclose the invention and the state of the art to which the invention pertains. Full citations for these references are provided below. The entirety of each of these references is incorporated herein.

For standard molecular biology and protein expression and isolation techniques, see: Sambrook, J., Russel, D. W. *Molecular Cloning, A Laboratory Manual.* 3 ed. 2001, Cold Spring Harbor, N.Y.: Cold Spring Harbor Laboratory Press
Altschul et al. (1990) *J. Mol. Biol.* 215: 405-410)
Brenna et al. (2012) *Chem Cat Chem.* 4: 653-659
Hall et al. (2008) *Eur. J. Org. Chem.* 1511
Hirata et al. (2009) *Journal of Molecular Catalysis B: Enzymatic.* 59: 158-162.
Iqbal et al. (2012) *Tetrahedron.* 68: 7619-7623
Lalonde and Margolin (2002) "Immobilization of Enzmes" in Drauz K. and Waidmann H., Enzyme catalysis in Organic Synthesis, Vo. III, 991-1032, Wiley-VCH, Weinheim.
Lucas S et. al. Complete sequence of *Acidovorax avenae* subsp. *avenae* ATCC 19860. Submitted (February-2011) to the EMBL/GenBank/DDBJ databases. Strain: ATCC 19860/DSM 7227/JCM 20985/NCPPB 1011.
US 2010/0035315
Needleman and Wunsch *J. Mol. Biol.* 48: 444-453 (1970)
Mangan et al. (2012) *Adv Synth Catal.* 354: 2185-2190
Mansell et al. (2013) *Catalysis.* 3: 370-379
Pearson and Lipman (1988) *PNAS USA* 85: 2444-2448
Peitruszka J. and Scholzel M., (2012) *Adv. Synth. Catal.,* 354: 751-756
Smith and Waterman (1981) *J. Mol Biol.* 147: 195-197
Winkler et al. (2013) *The Journal of Organic Chemistry.* 78: 1525-1533
Yanto et al. (2011), *Org. Lett.* 13: 2540

The invention claimed is:

1. A method of reducing an ethylene group in an unsaturated substrate, the method comprising contacting a solution comprising the unsaturated substrate with a catalyst, optionally in the presence of a co-substrate, thereby forming a reduced substrate;
   wherein the ethylene group in the unsaturated substrate is conjugated to an aldehyde, a ketone carbonyl, a carboxy group, an alkoxy carbonyl group, an amido group, or a nitro group;
   wherein the catalyst is a polypeptide comprising an amino acid sequence having at least 95% identity to SEQ ID NO: 1; and
   wherein the unsaturated substrate is initially present in the solution in a concentration in a range of from 50 mM to 1500 mM.

2. The method of claim 1 wherein the substrate concentration in the solution is at least 100 mM.

3. The method of claim 2 wherein the substrate concentration in the solution is at least 300 mM.

4. The method of claim 1 wherein the catalyst is a polypeptide comprising an amino acid sequence having at least 98% identity to SEQ ID NO: 1.

5. The method of claim 4 wherein the catalyst is a polypeptide comprising or consisting of the amino acid sequence of SEQ ID NO: 1.

6. The method of claim 1, wherein the ethylene group is conjugated to an acyl, carboxy, acyloxy, acylamino, or nitro group.

7. The method of claim 1, wherein the substrate is a compound of formula (I):

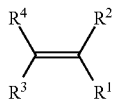

where:
   —$R^1$ is acyl, carboxy, acyloxy, nitro, acylamino, or nitrile;
   —$R^2$ is hydrogen, alkyl, alkenyl, alkynyl, cycloalkyl, heterocyclyl, aryl, amino, hydroxyl, or oxy;
   —$R^3$ is hydrogen, alkyl, alkenyl, alkynyl, cycloalkyl, heterocyclyl, aryl, amino, hydroxyl, oxy, carboxy, acyloxy, nitrile, or acylamino,
   or —$R^1$ and —$R^2$ or $R^1$ and $R^3$ form a ring containing an acyl, acyloxy or acylamino group, and
   —$R^4$ is hydrogen, alkyl, alkenyl, alkynyl, cycloalkyl, heterocyclyl, aryl, amino, hydroxyl, oxy, carboxy, acyloxy, nitrile, or acylamino,
   and each alkyl, alkenyl, alkynyl, cycloalkyl, heterocyclyl, and aryl group is optionally substituted;
   or —$R^2$ and —$R^4$ together form an unsubstituted or substituted ring.

8. The method of claim 1 wherein a co-substrate is present and is a cofactor.

9. The method of claim 8, wherein the cofactor is NADH.

10. The method of claim 1 wherein the substrate concentration in the solution is at least 500 mM.

11. The method of claim 1, wherein the substrate concentration in the solution is at least 750 mM.

12. The method of claim 1, wherein the catalyst is a polypeptide characterized as having high tolerance to substrate concentration.

13. The method of claim 1, wherein the catalyst is a polypeptide having an ability to catalytically reduce at least 70% of 2-methylcyclopent-2-en-1-one when contacted with the 2-methylcyclopent-2-en-1-one for 18 hours at 35° C., when the 2-methylcyclopent-2-en-1-one is initially present in the solution at a concentration of 50 mM.

* * * * *

SEQUENCE LISTING

```
<160> NUMBER OF SEQ ID NOS: 10

<210> SEQ ID NO 1
<211> LENGTH: 376
<212> TYPE: PRT
<213> ORGANISM: Acidovorax avenae

<400> SEQUENCE: 1

Met Ser His Thr Leu Phe Asp Pro Val Gln Ala Gly Asp Leu Gln Leu
1               5                   10                  15

Ala Asn Arg Ile Ala Met Ala Pro Leu Thr Arg Asn Arg Ser Pro Asn
            20                  25                  30

Ala Val Pro Lys Asp Ile Thr Ala Thr Tyr Tyr Ala Gln Arg Ala Thr
        35                  40                  45

Ala Gly Leu Leu Ile Thr Glu Ala Thr Ala Ile Ser His Gln Gly Gln
    50                  55                  60

Gly Tyr Ala Asp Val Pro Gly Leu Tyr Ser Thr Glu Gln Leu Asp Gly
```

```
         65                   70                  75                  80
Trp Lys Lys Val Thr Ala Ala Val His Glu Arg Gly Arg Ile Val
                 85                  90                  95
Thr Gln Leu Trp His Val Gly Arg Ile Ser His Asn Asp Leu Gln Pro
                100                 105                 110
Asp Gly Gly Ala Pro Val Ala Pro Ser Ala Ile Ala Ala Lys Ser Lys
            115                 120                 125
Thr Tyr Leu Ile Asp Lys Ala Thr Gly Gln Gly His Phe Ala Ala Thr
        130                 135                 140
Ser Glu Pro Arg Ala Leu Asp Ala Glu Leu Pro Gly Ile Val His
145                 150                 155                 160
Asp Tyr Ala Ala Ala Arg Asn Ala Val Glu Thr Ala Gly Phe Asp
                165                 170                 175
Gly Val Glu Ile His Gly Ala Asn Gly Tyr Leu Leu Asp Gln Phe Leu
            180                 185                 190
Lys Thr Gly Ala Asn Arg Arg Thr Asp Asp Tyr Gly Gly Ser Ile Glu
        195                 200                 205
Asn Arg Ala Arg Leu Leu Leu Glu Ala Thr Arg Ala Val Val Asp Ala
210                 215                 220
Ile Gly Gly Gly Lys Val Gly Ile Arg Leu Ser Pro Val Thr Pro Ala
225                 230                 235                 240
Asn Asp Ile Val Asp Ala Asp Pro Gln Pro Leu Phe Asp Tyr Val Ile
                245                 250                 255
Arg Gln Leu Ala Pro Leu Gly Leu Ala Tyr Val His Val Ile Glu Gly
            260                 265                 270
Ser Thr Gly Gly Pro Arg Glu Leu Glu Asp Arg Pro Phe Asp Tyr Glu
        275                 280                 285
Ala Leu Lys Thr Ala Tyr Arg Glu Ala Gly Gly Lys Gly Ala Trp Met
        290                 295                 300
Val Asn Asn Ala Tyr Asp Arg Ala Leu Ala Met Glu Ala Val Ala Ser
305                 310                 315                 320
Gly Arg Ala Asp Ile Val Ala Phe Gly Lys Ala Phe Ile Ser Asn Pro
                325                 330                 335
Asp Leu Val Glu Arg Leu Arg Gln Asp Ala Pro Leu Asn Pro Trp Asp
            340                 345                 350
Ser Lys Thr Phe Tyr Gly Gly Gly Glu Lys Gly Tyr Thr Asp Tyr Pro
        355                 360                 365
Thr Leu Gly Glu Ser Ala Lys Gly
    370                 375

<210> SEQ ID NO 2
<211> LENGTH: 1131
<212> TYPE: DNA
<213> ORGANISM: Acidovorax avenae

<400> SEQUENCE: 2
ttgtcccata cgcttttcga tcccgtccag gccggcgacc tgcagctcgc caaccgcatc    60
gccatggcgc cgctcacgcg caaccgctcg ccgaatgcgg tgcccaagga cattaccgcc   120
acctactacg cccagcgcgc caccgccggc ctgctgatca ccgaggccac ggccatcagc   180
caccagggcc agggctatgc ggacgtgccg ggcctgtaca gcaccgaaca gctcgatgga   240
tggaaaaagg tcaccgcagc ggtccatgag cgcggcggca ggatcgtgac ccagctctgg   300
cacgtgggcc gcatttccca caatgacctg cagcccgacg gcggcgcccc cgtggccccc   360
```

| | |
|---|---|
| tccgccatcg ccgccaagtc caagacctac ctgatcgaca aggccaccgg ccagggccat | 420 |
| ttcgcggcca cgtccgaacc ccgtgcgctg gatgccgaag agctgcccgg catcgtgcac | 480 |
| gactacgccg ccgccgcgcg caacgcggtg gagacggccg gattcgacgg cgtcgagatc | 540 |
| cacggcgcca acggctacct gctggaccag ttcctcaaga ccggcgccaa ccggcgcacc | 600 |
| gacgactacg gcggcagcat cgagaaccgc gcgcgcctgc tgctcgaagc cacgcgcgcc | 660 |
| gtggtggacg cgatcggcgg cggcaaggtg ggcatccgac tctcgcccgt cacgccggcc | 720 |
| aacgacatcg tcgatgccga tccgcagccg ctgttcgact acgtgatccg ccagctcgca | 780 |
| ccgctgggcc tggcctacgt gcacgtgatc gaaggctcca ccggcggccc gcgcgagctg | 840 |
| gaagaccgtc cgttcgacta cgaagccctg aagaccgcct accgcgaggc cggcggcaaa | 900 |
| ggcgcctgga tggtcaacaa cgcctatgac cgtgcgttgg cgatggaagc ggtgccagt | 960 |
| ggccgcgccg acatcgtcgc cttcggcaag gccttcatct ccaaccccga cctggtcgag | 1020 |
| cggctgcgcc aggacgcacc gctcaacccc tgggactcca agaccttcta cggcggcggc | 1080 |
| gagaagggct acaccgacta cccgacgctc ggcgaatcgg cgaaaggctg a | 1131 |

<210> SEQ ID NO 3
<211> LENGTH: 1134
<212> TYPE: DNA
<213> ORGANISM: Artificial sequence
<220> FEATURE:
<223> OTHER INFORMATION: Synthetic sequence: Nucleic acid sequence,
      codon-optimised, encoding catalyst (encoding SEQ ID NO:1)

<400> SEQUENCE: 3

| | |
|---|---|
| atgagccata ccctgtttga tccggttcag gcaggcgatc tgcagctggc aaatcgtatt | 60 |
| gcaatggcac cgctgacccg taatcgtagc ccgaatgcag ttccgaaaga tattaccgca | 120 |
| acctattatg cacagcgtgc aaccgcaggt ctgctgatta ccgaagcaac cgcaattagc | 180 |
| catcagggtc agggttatgc agatgttccg ggtctgtata gcaccgaaca gctggatggt | 240 |
| tggaaaaaag ttaccgcagc agtgcatgaa cgtggtggtc gtattgttac ccagctgtgg | 300 |
| catgtgggtc gtattagcca taatgatctg caaccggatg gtggtgctcc ggtggcaccg | 360 |
| agcgcaattg cagcaaaaag caaaacctat ctgattgata agcaaccggt caggtcat | 420 |
| tttgcagcaa ccagcgaacc gcgtgcactg gatgcagaag aactgcctgg tattgttcat | 480 |
| gattatgcag cagcagcacg taatgcagtt gaaaccgcag gctttgatgg tgttgaaatt | 540 |
| catggtgcaa atggctatct gctggatcag tttctgaaaa ccggtgcaaa tcgtcgtacc | 600 |
| gatgattatg gtggtagcat tgaaaatcgt gcccgtctgc tgctggaagc aacccgtgca | 660 |
| gttgttgatg caattggtgg tggtaaagtt ggtattcgtc tgagtccggt tacaccggca | 720 |
| aatgatattg tggatgccga tccgcagccg ctgtttgatt atgttattcg tcagctggct | 780 |
| ccgctgggtc tggcctatgt tcatgttatt gaaggtagca ccggtggtcc tcgtgaactg | 840 |
| gaagatcgtc cgttcgatta tgaagcactg aaaacagcat atcgtgaagc aggcggtaaa | 900 |
| ggtgcatgga tggttaataa tgcctatgat cgtgccctgg caatggaagc agttgcaagc | 960 |
| ggtcgtgcag atattgttgc atttggtaaa gcctttatta gcaatccgga tctggttgaa | 1020 |
| cgtctgcgtc aggatgctcc gctgaatccg tgggatagta aaaccttttta tggtggcggt | 1080 |
| gaaaaaggct ataccgatta tccgaccctg ggtgaaagcg caaaaggtta ataa | 1134 |

<210> SEQ ID NO 4
<211> LENGTH: 392
<212> TYPE: PRT

<213> ORGANISM: Artificial sequence
<220> FEATURE:
<223> OTHER INFORMATION: Synthetic sequence: Catalyst amino acid sequence, including T7 tag

<400> SEQUENCE: 4

```
Met Ala Ser Met Thr Gly Gly Gln Gln Met Gly Arg Gly Ser Glu Phe
1               5                   10                  15

Met Ser His Thr Leu Phe Asp Pro Val Gln Ala Gly Asp Leu Gln Leu
            20                  25                  30

Ala Asn Arg Ile Ala Met Ala Pro Leu Thr Arg Asn Arg Ser Pro Asn
        35                  40                  45

Ala Val Pro Lys Asp Ile Thr Ala Thr Tyr Tyr Ala Gln Arg Ala Thr
50                  55                  60

Ala Gly Leu Leu Ile Thr Glu Ala Thr Ala Ile Ser His Gln Gly Gln
65                  70                  75                  80

Gly Tyr Ala Asp Val Pro Gly Leu Tyr Ser Thr Glu Gln Leu Asp Gly
                85                  90                  95

Trp Lys Lys Val Thr Ala Ala Val His Glu Arg Gly Arg Ile Val
            100                 105                 110

Thr Gln Leu Trp His Val Gly Arg Ile Ser His Asn Asp Leu Gln Pro
        115                 120                 125

Asp Gly Gly Ala Pro Val Ala Pro Ser Ala Ile Ala Ala Lys Ser Lys
130                 135                 140

Thr Tyr Leu Ile Asp Lys Ala Thr Gly Gln Gly His Phe Ala Ala Thr
145                 150                 155                 160

Ser Glu Pro Arg Ala Leu Asp Ala Glu Glu Leu Pro Gly Ile Val His
                165                 170                 175

Asp Tyr Ala Ala Ala Arg Asn Ala Val Glu Thr Ala Gly Phe Asp
            180                 185                 190

Gly Val Glu Ile His Gly Ala Asn Gly Tyr Leu Leu Asp Gln Phe Leu
        195                 200                 205

Lys Thr Gly Ala Asn Arg Arg Thr Asp Asp Tyr Gly Gly Ser Ile Glu
210                 215                 220

Asn Arg Ala Arg Leu Leu Leu Glu Ala Thr Arg Ala Val Val Asp Ala
225                 230                 235                 240

Ile Gly Gly Gly Lys Val Gly Ile Arg Leu Ser Pro Val Thr Pro Ala
                245                 250                 255

Asn Asp Ile Val Asp Ala Asp Pro Gln Pro Leu Phe Asp Tyr Val Ile
            260                 265                 270

Arg Gln Leu Ala Pro Leu Gly Leu Ala Tyr Val His Val Ile Glu Gly
        275                 280                 285

Ser Thr Gly Gly Pro Arg Glu Leu Glu Asp Arg Pro Phe Asp Tyr Glu
290                 295                 300

Ala Leu Lys Thr Ala Tyr Arg Glu Ala Gly Lys Gly Ala Trp Met
305                 310                 315                 320

Val Asn Asn Ala Tyr Asp Arg Ala Leu Ala Met Glu Ala Val Ala Ser
                325                 330                 335

Gly Arg Ala Asp Ile Val Ala Phe Gly Lys Ala Phe Ile Ser Asn Pro
            340                 345                 350

Asp Leu Val Glu Arg Leu Arg Gln Asp Ala Pro Leu Asn Pro Trp Asp
        355                 360                 365

Ser Lys Thr Phe Tyr Gly Gly Gly Glu Lys Gly Tyr Thr Asp Tyr Pro
370                 375                 380
```

Thr Leu Gly Glu Ser Ala Lys Gly
385                 390

<210> SEQ ID NO 5
<211> LENGTH: 412
<212> TYPE: PRT
<213> ORGANISM: Artificial sequence
<220> FEATURE:
<223> OTHER INFORMATION: Synthetic sequence: Catalyst amino acid
      sequence, including His tag and T7 tag

<400> SEQUENCE: 5

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Glu Phe Met Ser His Thr Leu Phe Asp Pro Val Gln Ala Gly
        35                  40                  45

Asp Leu Gln Leu Ala Asn Arg Ile Ala Met Ala Pro Leu Thr Arg Asn
    50                  55                  60

Arg Ser Pro Asn Ala Val Pro Lys Asp Ile Thr Ala Thr Tyr Tyr Ala
65                  70                  75                  80

Gln Arg Ala Thr Ala Gly Leu Leu Ile Thr Glu Ala Thr Ala Ile Ser
                85                  90                  95

His Gln Gly Gln Gly Tyr Ala Asp Val Pro Gly Leu Tyr Ser Thr Glu
            100                 105                 110

Gln Leu Asp Gly Trp Lys Lys Val Thr Ala Ala Val His Glu Arg Gly
        115                 120                 125

Gly Arg Ile Val Thr Gln Leu Trp His Val Gly Arg Ile Ser His Asn
    130                 135                 140

Asp Leu Gln Pro Asp Gly Gly Ala Pro Val Ala Pro Ser Ala Ile Ala
145                 150                 155                 160

Ala Lys Ser Lys Thr Tyr Leu Ile Asp Lys Ala Thr Gly Gln Gly His
                165                 170                 175

Phe Ala Ala Thr Ser Glu Pro Arg Ala Leu Asp Ala Glu Glu Leu Pro
            180                 185                 190

Gly Ile Val His Asp Tyr Ala Ala Ala Arg Asn Ala Val Glu Thr
        195                 200                 205

Ala Gly Phe Asp Gly Val Glu Ile His Gly Ala Asn Gly Tyr Leu Leu
    210                 215                 220

Asp Gln Phe Leu Lys Thr Gly Ala Asn Arg Arg Thr Asp Asp Tyr Gly
225                 230                 235                 240

Gly Ser Ile Glu Asn Arg Ala Arg Leu Leu Leu Glu Ala Thr Arg Ala
                245                 250                 255

Val Val Asp Ala Ile Gly Gly Lys Val Gly Ile Arg Leu Ser Pro
            260                 265                 270

Val Thr Pro Ala Asn Asp Ile Val Asp Ala Asp Pro Gln Pro Leu Phe
        275                 280                 285

Asp Tyr Val Ile Arg Gln Leu Ala Pro Leu Gly Leu Ala Tyr Val His
    290                 295                 300

Val Ile Glu Gly Ser Thr Gly Gly Pro Arg Glu Leu Glu Asp Arg Pro
305                 310                 315                 320

Phe Asp Tyr Glu Ala Leu Lys Thr Ala Tyr Arg Glu Ala Gly Gly Lys
                325                 330                 335

Gly Ala Trp Met Val Asn Asn Ala Tyr Asp Arg Ala Leu Ala Met Glu
            340                 345                 350

Ala Val Ala Ser Gly Arg Ala Asp Ile Val Ala Phe Gly Lys Ala Phe
           355                 360                 365

Ile Ser Asn Pro Asp Leu Val Glu Arg Leu Arg Gln Asp Ala Pro Leu
    370                 375                 380

Asn Pro Trp Asp Ser Lys Thr Phe Tyr Gly Gly Glu Lys Gly Tyr
385                 390                 395                 400

Thr Asp Tyr Pro Thr Leu Gly Glu Ser Ala Lys Gly
                405                 410

<210> SEQ ID NO 6
<211> LENGTH: 1239
<212> TYPE: DNA
<213> ORGANISM: Artificial sequence
<220> FEATURE:
<223> OTHER INFORMATION: Synthetic sequence: Nucleic acid sequence
      encoding catalyst including His tag and T7 tag (encoding SEQ ID
      NO:5)

<400> SEQUENCE: 6
atgggcagca gccatcatca tcatcatcac agcagcggcc tggtgccgcg cggcagccat      60
atggctagca tgactggtgg acagcaaatg ggtcgcggat ccgaattcat gtcccatacg     120
cttttcgatc ccgtccaggc cggcgacctg cagctcgcca accgcatcgc catggcgccg     180
ctcacgcgca accgctcgcc gaatgcggtg cccaaggaca ttaccgccac ctactacgcc     240
cagcgcgcca ccgccggcct gctgatcacc gaggccacgg ccatcagcca ccagggccag     300
ggctatgcgg acgtgccggg cctgtacagc accgaacagc tcgatggatg gaaaaaggtc     360
accgcagcgg tccatgagcg cggcggcagg atcgtgaccc agctctggca cgtgggccgc     420
atttcccaca tgaccctgca gcccgacggc ggcgccccg tggccccctc cgccatcgcc     480
gccaagtcca agacctacct gatcgacaag gccaccggcg agggccattt cgcggccacg     540
tccgaacccc gtgcgctgga tgccgaagag ctgcccggca tcgtgcacga ctacgccgcc     600
gccgcgcgca acgcggtgga cacggccgga ttcgacgggc tcgagatcca cggcgccaac     660
ggctacctgc tggaccagtt cctcaagacc ggcgccaacc ggcgcaccga cgactacggc     720
ggcagcatcg agaaccgcgc gcgcctgctg ctcgaagcca cgcgcgccgt ggtggacgcg     780
atcggcggcg gcaaggtggg catccgactc tcgcccgtca cgccggccaa cgacatcgtc     840
gatgccgatc cgcagccgct gttcgactac gtgatccgcc agctcgcacc gctgggcctg     900
gcctacgtgc acgtgatcga aggctccacc ggcggcccgc gcgagctgga agaccgtccg     960
ttcgactaca agcccctgaa gaccgcctac cgcgaggccg gcggcaaagg cgcctggatg    1020
gtcaacaacg cctatgaccg tgcgttggcg atggaagcgg tggccagtgg ccgcgccgac    1080
atcgtcgcct tcggcaaggc cttcatctcc aaccccgacc tggtcgagcg gctgcgccag    1140
gacgcaccgc tcaaccccctg ggactccaag accttctacg gcggcggcga agggctac    1200 accgactacc cgacgctcgg cgaatcggcg aaaggctga                            1239

<210> SEQ ID NO 7
<211> LENGTH: 364
<212> TYPE: PRT
<213> ORGANISM: Chromobacterium violaceum

<400> SEQUENCE: 7

Met Asn Ala Asp Lys Leu Leu Thr Pro Leu Thr Met Gly Ala Val Ala
1               5                   10                  15

Leu Ser Asn Arg Val Val Met Ala Pro Leu Thr Arg Leu Arg Asn Ile

```
                20                  25                  30
Glu Pro Gly Asp Val Pro Gly Leu Ala Lys Glu Tyr Tyr Arg Gln
            35                  40                  45

Arg Ala Ser Ala Gly Leu Ile Val Ala Glu Gly Thr His Ile Ser Pro
50                  55                  60

Thr Ala Lys Gly Tyr Ala Gly Ala Pro Gly Ile Tyr Ser Glu Glu Gln
65                  70                  75                  80

Val Arg Ala Trp Ser Glu Val Thr Gly Ala Val His Gln Asp Gly Gly
                85                  90                  95

Lys Ile Ala Leu Gln Leu Trp His Thr Gly Arg Ile Ser His Arg Ser
            100                 105                 110

Leu Gln Pro Asn Gly Asp Ala Pro Val Gly Pro Ser Ala Ile Gln Ala
            115                 120                 125

Asp Ser Arg Thr Asn Ile Arg Ala Ala Asp Gly Ser Leu Val Arg Glu
            130                 135                 140

Gln Cys Asp Thr Pro Arg Ala Leu Glu Ile Glu Glu Ile Glu Asp Ile
145                 150                 155                 160

Ile Glu Asp Tyr Arg Arg Ala Ala Asp Asn Ala Arg Arg Ala Gly Phe
                165                 170                 175

Asp Met Val Glu Ile His Gly Ala His Gly Tyr Leu Ile Asp Gln Phe
            180                 185                 190

Leu Ser Pro Ala Ala Asn Val Arg Thr Asp Gln Tyr Gly Gly Ser Val
            195                 200                 205

Glu Asn Arg Ala Arg Phe Leu Leu Glu Val Val Asp Ala Val Val Ala
            210                 215                 220

Glu Trp Asp Ala Asp His Val Gly Ile Arg Ile Ser Pro Leu Gly Ile
225                 230                 235                 240

Phe Asn Gly Val Ser Asn Thr Asp Gln Leu Asp Met Ala Leu Tyr Leu
                245                 250                 255

Ala Glu Gln Leu Ala Lys Arg Lys Leu Ala Phe Leu His Ile Ser Glu
            260                 265                 270

Pro Asp Trp Ala Gly Gly Pro Thr Leu Asp Asp Gly Phe Arg Ala Glu
            275                 280                 285

Leu Arg Gln Arg Tyr Pro Gly Val Ile Ile Gly Ala Gly Gly Tyr Ser
            290                 295                 300

Ala Glu Lys Ala Glu Thr Leu Leu Lys Lys Gly Phe Ile Asp Ala Ala
305                 310                 315                 320

Ala Phe Gly Arg Ser Tyr Ile Ala Asn Pro Asp Leu Val Glu Arg Leu
                325                 330                 335

Lys Gln Asn Ala Pro Leu Asn Pro Pro Lys Pro Asp Thr Phe Tyr Gly
            340                 345                 350

Gly Gly Ala Glu Gly Tyr Thr Asp Tyr Pro Thr Leu
            355                 360

<210> SEQ ID NO 8
<211> LENGTH: 1095
<212> TYPE: DNA
<213> ORGANISM: Chromobacterium violaceum

<400> SEQUENCE: 8
atgaacgccg acaaactgct gacccgctg accatgggcg ccgtcgccct gagcaaccgc      60
gtcgtcatgg ccccgctgac cgcctgcgc aacatcgaac cgggcgacgt gcccggcccg     120
ctggccaagg aatactaccg ccagcgcgcc agcgccggcc tgatcgtggc cgaaggcacc     180
```

```
cacatttccc ccaccgccaa gggctatgcc ggcgcgcccg gcatctacag cgaggaacaa    240
gtgcgcgcct ggagcgaagt caccggcgcg gtgcatcaag acggcggcaa gatcgcgctg    300
caactgtggc acaccggccg catctcgcac cgctcgctgc agccgaacgg cgacgcgccg    360
gtcggcccgt ccgccatcca ggccgacagc cgcaccaaca tccgcgccgc cgacggcagc    420
ctggtgcgcg aacaatgcga caccccgcgc gcgctggaaa tcgaggaaat cgaggacatc    480
atcgaggact accgccgcgc cgccgacaac gcgcgccgcg ccggtttcga catggtggag    540
atccacggcg cccacggcta tctgatcgac cagttcctgt cgccggccgc caacgtccgc    600
accgaccagt acggcggcag cgtggaaaac cgcgcccgct tcctgctgga agtggtggac    660
gcggtggtgg cggaatggga cgccgatcac gtcggcatcc gcatctcgcc gctgggcatc    720
ttcaacggcg tcagcaacac cgaccagctg acatggcgc tgtacctggc cgagcagttg     780
gccaagcgca agctggcctt cctgcacatc tccgagccgg actgggccgg cggcccgacg    840
ctggacgacg gcttccgcgc cgaactgcgc cagcgctatc ccggcgtgat catcggcgcc    900
ggcggctact ccgcggagaa ggccgaaacg ctgctgaaga aaggctttat cgacgccgcc    960
gccttcggcc gcagctacat cgccaacccg gatctggtgg agcgtctgaa gcagaacgct   1020
ccgctgaacc gcccaagcc ggatactttc tatggcggcg cgcgcgaagg ctataccgac    1080
tacccgacgc tgtaa                                                   1095
```

<210> SEQ ID NO 9
<211> LENGTH: 338
<212> TYPE: PRT
<213> ORGANISM: Bacillus sp.

<400> SEQUENCE: 9

```
Met Asp Thr Lys Leu Phe Ser Ser Tyr Thr Val Lys Asp Val Thr Leu
1               5                   10                  15

Lys Asn Arg Ile Val Met Ala Pro Met Cys Met Tyr Ser Ser His Asn
            20                  25                  30

Glu Asp Gly Lys Val Glu Asn Trp His Leu Thr His Tyr Thr Ser Arg
        35                  40                  45

Ala Val Gly Gln Val Gly Leu Ile Ile Val Glu Ala Thr Ala Val Thr
    50                  55                  60

Ala Gln Gly Arg Ile Ser Pro Gln Asp Leu Gly Ile Trp Ser Asp Asp
65                  70                  75                  80

His Ile Glu Gly Leu Gln Gln Leu Thr Gly Met Met Lys Glu His Gly
                85                  90                  95

Thr Arg Ala Gly Ile Gln Leu Ala His Ala Gly Arg Lys Ala Val Ile
            100                 105                 110

Glu Gly Glu Ile Ile Ala Pro Ser Ala Val Ala Phe Asn Glu Lys Met
        115                 120                 125

Lys Lys Pro Lys Glu Met Thr Lys Glu Glu Ile Lys Glu Thr Ile Glu
    130                 135                 140

Ala Phe Lys Glu Gly Ala Val Arg Ala Lys Lys Ala Gly Phe Glu Val
145                 150                 155                 160

Ile Glu Ile His Ala Ala His Gly Tyr Leu Ile Asn Glu Phe Leu Ser
                165                 170                 175

Pro Leu Ser Asn Leu Arg Glu Asp Glu Tyr Gly Gly Ile Ala Glu Asn
            180                 185                 190

Arg Tyr Arg Phe Leu Arg Glu Val Ile Asp Ser Ile Gln Ser Val Trp
        195                 200                 205
```

```
Asp Gly Pro Leu Phe Val Arg Val Ser Ala Ser Asp Tyr Asn Glu Asn
    210                 215                 220

Gly Leu Asp Val Glu Asp Tyr Val Thr Phe Gly Arg Trp Met Lys Glu
225                 230                 235                 240

Gln Gly Ile Asp Leu Ile Asp Val Ser Ser Gly Ala Leu Val Pro Ala
                245                 250                 255

Arg Ile His Ala Tyr Pro Gly Tyr Gln Val Lys Phe Ala Glu Thr Ile
            260                 265                 270

Lys Asn Glu Ala Asp Ile Pro Thr Gly Ala Val Gly Leu Ile Thr Ser
        275                 280                 285

Gly Leu Gln Ala Glu Glu Ile Leu Gln Asn Asp Arg Ala Asp Leu Ile
    290                 295                 300

Phe Ile Ala Arg Glu Leu Leu Arg Asp Pro Tyr Phe Pro Lys Thr Ala
305                 310                 315                 320

Ala Lys Gln Leu Gly Thr Glu Ile Glu Pro Pro Lys Gln Tyr Asp Arg
                325                 330                 335

Gly Trp

<210> SEQ ID NO 10
<211> LENGTH: 1017
<212> TYPE: DNA
<213> ORGANISM: Bacillus sp.

<400> SEQUENCE: 10
atggacacaa agttattttc ttcatacaca gtgaaagacg tcacactaaa aaaccgcatc      60
gtcatggcgc cgatgtgcat gtattccagc cataatgaag atggaaaagt agaaaactgg     120
catttgaccc attatacaag cagagctgtt ggacaggttg gcctgatcat tgtggaagcg     180
accgctgtaa ctgcgcaggg ccgcatttca ccacaggatc tggggatctg gagcgatgat     240
catatcgagg gctgcagca gctgacaggc atgatgaagg agcatggcac ccgtgccggc     300
atccagcttg cgcatgcagg cagaaaagcg gttattgagg gcgaaatcat tgctccatct     360
gccgtggctt tcaatgaaaa aatgaaaaag cctaaagaga tgacaaaaga agagattaaa     420
gaaacgatcg aagcctttaa ggaaggcgct gtccgtgcta aaaaagcagg cttcgaggtt     480
atagaaatcc atgctgccca cggctatctg atcaatgagt ttctatcccc gctttccaat     540
ctgcgggagg atgaatacgg cgggatcgca gaaaaccgct accgcttcct gagggaagtc     600
atcgacagca tccagtctgt ttgggacgga cctctctttg taagggtatc agcgagcgat     660
tataacgaaa acggacttga tgttgaggat tatgtcacgt tcgggcgctg gatgaaagag     720
cagggcatcg acctgatcga tgtaagctcc ggagcactgg tgccggcccg cattcacgct     780
tatccaggct accaggtcaa attcgctgaa accatcaaga tgaggcaga catcccgaca     840 ggcgccgtcg gcctgattac atccggactg caggctgaag agatcctgca aaacgacaga     900
gcagacctta tcttcatcgc acgtgagctg ctccgcgatc catacttccc aaaaaccgca     960
gccaaacagc tcggcaccga aatcgaaccc ccgaaacaat atgatagagg gtggtaa     1017
```